United States Patent
Fassler et al.

(10) Patent No.: US 12,351,629 B2
(45) Date of Patent: Jul. 8, 2025

(54) TREM2 ANTIBODIES AND USES THEREOF

(71) Applicant: MOR RESEARCH APPLICATIONS LTD., Ramat Gan (IL)

(72) Inventors: Michael Fassler, Ness Ziona (IL); Jacob George, Tel Aviv (IL)

(73) Assignee: MOR RESEARCH APPLICATIONS LTD., Ramat Gan (IL)

( * ) Notice: Subject to any disclaimer, the term of this patent is extended or adjusted under 35 U.S.C. 154(b) by 1036 days.

(21) Appl. No.: 17/312,747

(22) PCT Filed: Dec. 10, 2019

(86) PCT No.: PCT/IB2019/060620
§ 371 (c)(1),
(2) Date: Jun. 10, 2021

(87) PCT Pub. No.: WO2020/121195
PCT Pub. Date: Jun. 18, 2020

(65) Prior Publication Data
US 2022/0127356 A1 Apr. 28, 2022

Related U.S. Application Data

(60) Provisional application No. 62/789,272, filed on Jan. 7, 2019, provisional application No. 62/777,613, filed on Dec. 10, 2018.

(51) Int. Cl.
*A61P 25/28* (2006.01)
*A61P 29/00* (2006.01)
*C07K 16/28* (2006.01)
*A61K 39/00* (2006.01)

(52) U.S. Cl.
CPC .......... *C07K 16/2803* (2013.01); *A61P 25/28* (2018.01); *A61P 29/00* (2018.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| | | |
|---|---|---|
| WO | WO-2016023019 A2 | 2/2016 |
| WO | WO-2017062672 A2 | 4/2017 |
| WO | WO-2018015573 A2 | 1/2018 |
| WO | WO-2018195506 A1 | 10/2018 |
| WO | WO-2020121195 A1 | 6/2020 |

OTHER PUBLICATIONS

Koenig et al., Mutational landscape of antibody variable domains reveals a switch modulating the interdomain conformational dynamics and antigen binding; 2017, PNAS, 114(4): E486-495. (Year: 2017).*
MacCallum et al., Antibody-antigen interactions: contact analysis and binding site topography; 1996, J. Mol. Biol., 262: 732-745. (Year: 1996).*
Mantzavinos et al., Biomarkers for alzheimer's disease diagnosis; 2017, Current Alzheimer Research, 14(11): 1149-1154. (Year: 2017).*
Deming, Y., et al., "Triggering receptor expressed on myeloid cells 2 (TREM2): a potential therapeutic target for Alzheimer disease?" Expert Opinion on Therapeutic Targets 22(7):587-598, Informa, United Kingdom (Jun. 2018).
Guerreiro, R. J., et al., "Using exome sequencing to reveal mutations in TREM2 presenting as a frontotemporal dementia-like syndrome without bone involvement," *JAMA Neurology* 70(1):78-84, American Medical Association, United States (Jan. 2013).
Guerreiro, R., et al., "TREM2 variants in Alzheimer's disease," *New England Journal of Medicine* 368(2):117-127, Massachusetts Medical Society, United States (published online Nov. 2012, published in print Jan. 2013).
Hsieh, C. L., et al., "A role for TREM2 ligands in the phagocytosis of apoptotic neuronal cells by microglia," *Journal of Neurochemistry* 109(4):1144-1156, Wiley on behalf of the International Society for Neurochemistry, United Kingdom (published online Mar. 2009, published in print May 2009).
International Search Report and Written Opinion for International Application No. PCT/IB2019/060620, Israel Patent Office, Israel, mailed on Jan. 15, 2020, 10 pages.
Jay, T. R., et al., "TREM2 deficiency eliminates TREM2+ inflammatory macrophages and ameliorates pathology in Alzheimer's disease mouse models," *Journal of Experimental Medicine* 212(3):287-295, Rockefeller University Press, United States (Mar. 2015).
Jay, T. R., et al., "Disease Progression-Dependent Effects of TREM2 Deficiency in a Mouse Model of Alzheimer's Disease," *Journal of Neuroscience* 37(3):637-647, Society for Neuroscience, United States (Jan. 2017).
Jonsson, T., et al., "Variant of TREM2 associated with the risk of Alzheimer's disease," *New England Journal of Medicine* 368(2):107-116, Massachusetts Medical Society, United States (published online Nov. 2012, published in print Jan. 2013).
Kawabori, M., et al., "Triggering receptor expressed on myeloid cells 2 (TREM2) deficiency attenuates phagocytic activities of microglia and exacerbates ischemic damage in experimental stroke," *Journal of the Society for Neuroscience* 35(8):3384-3396, Society for Neuroscience, United States (Feb. 2015).
Kleinberger, G., et al., "TREM2 mutations implicated in neurodegeneration impair cell surface transport and phagocytosis," *Science Translational Medicine* 6(243):243ra86, American Association for the Advancement of Science, United States (Jul. 2014), 13 pages.

(Continued)

*Primary Examiner* — Daniel E Kolker
*Assistant Examiner* — James Ryland Melchior
(74) *Attorney, Agent, or Firm* — Sterne, Kessler, Goldstein & Fox P.L.L.C.

(57) ABSTRACT

The present disclosure provides antibodies and antigen-binding fragments thereof that specifically bind to human Triggering Receptor Expressed on Myeloid Cells 2 (TREM2). The anti-TREM2 antibodies or antigen-binding fragments thereof are useful, for example, in detecting TREM2 and in treating neurodegenerative diseases.

22 Claims, 21 Drawing Sheets
Specification includes a Sequence Listing.

(56) References Cited

OTHER PUBLICATIONS

Matarin, M., et al., "A genome-wide gene-expression analysis and database in transgenic mice during development of amyloid or tau pathology," *Cell Reports* 10(4):633-644, Cell Press, United States (published online Jan. 2015, published in print Feb. 2015).

Paloneva, J., et al., "Mutations in two genes encoding different subunits of a receptor signaling complex result in an identical disease phenotype," *American Journal of Human Genetics* 71(3):656-662, American Society of Human Genetics, United States (published online Jun. 2002, published in print Sep. 2002).

Sieber, M. W., et al., "Attenuated inflammatory response in triggering receptor expressed on myeloid cells 2 (TREM2) knock-out mice following stroke," *PLoS One* 8(1): e52982, Public Library of Science, United States (Jan. 2013), 10 pages.

Smith, A. M., and Dragunow, M., "The human side of microglia," *Trends in Neurosciences* 37(3):125-135, Cell Press, United States (published online Jan. 2014, published in print Mar. 2014).

Takahashi, K., et al., "Clearance of apoptotic neurons without inflammation by microglial triggering receptor expressed on myeloid cells-2," *Journal of Experimental Medicine* 201(4):647-657, Rockefeller University Press, United States (Feb. 2005).

Turnbull, I. R., et al., "Cutting edge: TREM-2 attenuates macrophage activation," *Journal of Immunology* 177(6):3520-3524, American Association of Immunologists, United States (Sep. 2006).

Ulland, T. K., et al., "TREM2 Maintains Microglial Metabolic Fitness in Alzheimer's Disease," *Cell* 170(4):649-663.e13, Cell Press, United States (Aug. 2017).

Wang, Y., et al., "TREM2 lipid sensing sustains the microglial response in an Alzheimer's disease model," *Cell* 160(6):1061-1071, Cell Press, United States (published online Feb. 2015, published in print Mar. 2015).

Xiang, X., et al., "TREM2 deficiency reduces the efficacy of immunotherapeutic amyloid clearance," *EMBO Molecular Medicine* 8(9):992-1004, Wiley-Blackwell, United Kingdom (Sep. 2016).

Zhang, B., et al., "Integrated systems approach identifies genetic nodes and networks in late-onset Alzheimer's disease," *Cell* 153(3):707-720, Cell Press, United States (Apr. 2013).

Budapest Restricted Certificate of Deposit for ATCC Patent Deposit Designation PTA-125491 dated Jan. 2, 2019, Manassas, Virginia, USA, 2 pages.

\* cited by examiner

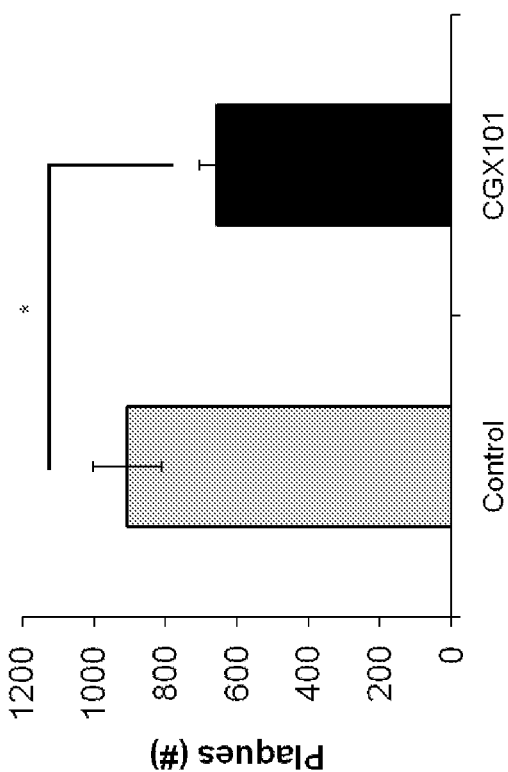
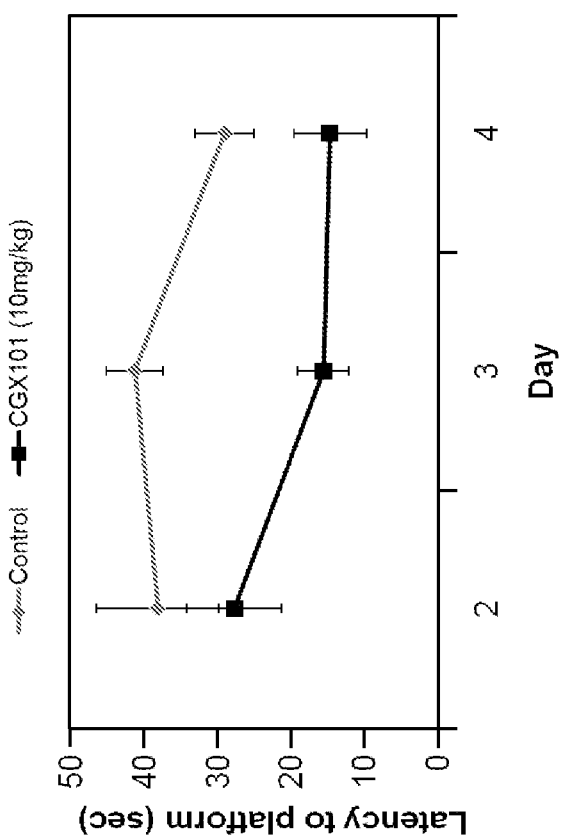
FIG. 12B
FIG. 12A

SEQUENCE LISTING

```
<160> NUMBER OF SEQ ID NOS: 14

<210> SEQ ID NO 1
<211> LENGTH: 8
<212> TYPE: PRT
<213> ORGANISM: Artificial Sequence
<220> FEATURE:
<223> OTHER INFORMATION: CGX101 CDR H1 IMGT

<400> SEQUENCE: 1

Gly Tyr Thr Phe Thr Asp Tyr Asn
1               5

<210> SEQ ID NO 2
<211> LENGTH: 8
<212> TYPE: PRT
<213> ORGANISM: Artificial Sequence
<220> FEATURE:
<223> OTHER INFORMATION: CGX101 CDR H2 IMGT

<400> SEQUENCE: 2

Ile Tyr Pro Lys Asn Gly Gly Thr
1               5

<210> SEQ ID NO 3
<211> LENGTH: 12
<212> TYPE: PRT
<213> ORGANISM: Artificial Sequence
<220> FEATURE:
<223> OTHER INFORMATION: CGX101 CDR H3 IMGT

<400> SEQUENCE: 3

Ala Arg Arg Thr Ala Arg Ala Ser Trp Phe Ala Phe
1               5                   10
```

<210> SEQ ID NO 4
<211> LENGTH: 12
<212> TYPE: PRT
<213> ORGANISM: Artificial Sequence
<220> FEATURE:
<223> OTHER INFORMATION: CGX101 CDR L1 IMGT

<400> SEQUENCE: 4

Gln Ser Leu Leu Tyr Ser Ser Asn Gln Lys Asn Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: CGX101 CDR L2 IMGT

<400> SEQUENCE: 5

Trp Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: CGX101 CDR L3

<400> SEQUENCE: 6

Gln Gln Tyr Tyr Asn Tyr Pro Phe Thr
1               5

<210> SEQ ID NO 7
<211> LENGTH: 119
<212> TYPE: PRT
<213> ORGANISM: Artificial Sequence
<220> FEATURE:
<223> OTHER INFORMATION: hCGX101 VH

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asp Tyr
            20                  25                  30

Asn Ile His Trp Val Arg Gln Met Pro Gly Lys Gly Leu Glu Trp Met
        35                  40                  45

Gly Tyr Ile Tyr Pro Lys Asn Gly Gly Thr Gly Tyr Thr Gln Lys Phe
    50                  55                  60

Lys Ser Gln Val Thr Ile Ser Val Asp Asn Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Thr Ala Arg Ala Ser Trp Phe Ala Phe Trp Gly Gln Gly
            100                 105                 110

Thr Leu Val Thr Val Ser Ser
        115

<210> SEQ ID NO 8
<211> LENGTH: 113
<212> TYPE: PRT
<213> ORGANISM: Artificial Sequence
<220> FEATURE:
<223> OTHER INFORMATION: hCGX101 VL

```
<400> SEQUENCE: 8

Asp Ile Val Met Thr Gln Ser Pro Ala Thr Leu Ser Val Ser Pro Gly
1               5                   10                  15

Glu Arg Ala Thr Leu Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ala Pro Arg Val Leu Ile Tyr Trp Ala Ser Thr Arg Glu Ser Gly Ile
    50                  55                  60

Pro Ala Arg Phe Ser Gly Ser Gly Ser Gly Thr Glu Phe Thr Leu Thr
65                  70                  75                  80

Ile Ser Ser Leu Gln Ser Glu Asp Phe Ala Val Tyr Tyr Cys Gln Gln
                85                  90                  95

Tyr Tyr Asn Tyr Pro Phe Thr Phe Gly Gln Gly Thr Lys Leu Glu Ile
                100                 105                 110

Lys

<210> SEQ ID NO 9
<211> LENGTH: 230
<212> TYPE: PRT
<213> ORGANISM: Homo sapiens

<400> SEQUENCE: 9

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
                20                  25                  30

Gln Val Ser Cys Pro Tyr Asp Ser Met Lys His Trp Gly Arg Arg Lys
            35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
                100                 105                 110

Leu His Gly Ser Glu Ala Asp Thr Leu Arg Lys Val Leu Val Glu Val
            115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
                180                 185                 190

Leu Trp Ala Ala Ala Trp His Gly Gln Lys Pro Gly Thr His Pro Pro
            195                 200                 205

Ser Glu Leu Asp Cys Gly His Asp Pro Gly Tyr Gln Leu Gln Thr Leu
    210                 215                 220

Pro Gly Leu Arg Asp Thr
225                 230
```

```
<210> SEQ ID NO 10
<211> LENGTH: 5
<212> TYPE: PRT
<213> ORGANISM: Artificial Sequence
<220> FEATURE:
<223> OTHER INFORMATION: CGX101 CDR H1 KABAT

<400> SEQUENCE: 10

Asp Tyr Asn Ile His
1               5

<210> SEQ ID NO 11
<211> LENGTH: 17
<212> TYPE: PRT
<213> ORGANISM: Artificial Sequence
<220> FEATURE:
<223> OTHER INFORMATION: CGX101 CDR H2 KABAT

<400> SEQUENCE: 11

Tyr Ile Tyr Pro Lys Asn Gly Gly Thr Gly Tyr Thr Gln Lys Phe Lys
1               5                   10                  15

Ser

<210> SEQ ID NO 12
<211> LENGTH: 10
<212> TYPE: PRT
<213> ORGANISM: Artificial Sequence
<220> FEATURE:
<223> OTHER INFORMATION: CGX101 CDR H3 KABAT

<400> SEQUENCE: 12

Arg Thr Ala Arg Ala Ser Trp Phe Ala Phe
1               5                   10

<210> SEQ ID NO 13
<211> LENGTH: 17
<212> TYPE: PRT
<213> ORGANISM: Artificial Sequence
<220> FEATURE:
<223> OTHER INFORMATION: CGX101 CDR L1 KABAT

<400> SEQUENCE: 13

Lys Ser Ser Gln Ser Leu Leu Tyr Ser Ser Asn Gln Lys Asn Tyr Leu
1               5                   10                  15

Ala

<210> SEQ ID NO 14
<211> LENGTH: 7
<212> TYPE: PRT
<213> ORGANISM: Artificial Sequence
<220> FEATURE:
<223> OTHER INFORMATION: CGX101 CDR L2 KABAT

<400> SEQUENCE: 14

Trp Ala Ser Thr Arg Glu Ser
1               5
```

TREM2 ANTIBODIES AND USES THEREOF

CROSS-REFERENCE TO RELATED APPLICATIONS

This application is a U.S. National Phase of International Appl. No. PCT/IB2019/060620, filed Dec. 10, 2019, which claims priority benefit of U.S. Provisional Appl. No. 62/777,613, filed Dec. 10, 2018, which claims priority benefit of U.S. Provisional Appl. No. 62/789,272, filed Jan. 7, 2019, each of which is hereby incorporated by reference herein in its entirety.

BACKGROUND OF THE INVENTION

Field of the Invention

The present disclosure provides antibodies and antigen-binding fragments thereof that bind to the extracellular domain of Triggering Receptor Expressed on Myeloid Cells 2 (TREM2) and methods of using the same.

Background

Alzheimer's disease (AD), the most common form of dementia, is evident pathologically by the abnormal accumulation of amyloid plaques, hyperphosphorylated tau aggregates, and microgliosis. The recent genetic implication of a microglial-expressed gene, Triggering Receptor Expressed on Myeloid Cells 2 (TREM2), in late-onset AD suggests a requisite role for microglia in AD pathogenesis. Although mutations in TREM2 are rare, this gene may be the most robust immune gene-specific risk factor for AD known yet. TREM2 encodes a transmembrane receptor that is expressed by microglia in the brain. TREM2 has been shown to be involved in neuroinflammation and in the metabolic fitness, proliferation, survival, and phagocytic capacity of microglia.

Gene network analyses of human AD brains and mouse models of AD have highlighted a central role for microglia in AD and, in particular, TREM2 and its binding partner TYRO protein tyrosine kinase-binding protein (TYROBP), also known as DNAX-activation protein 12 (DAP12) DAP12/TYROBP (Matarin, et al., Cell Rep.10:633-644 (2015), Zhang et al., Cell 153(3):707-720 (2013). Whereas heterozygous variants in TREM2 are associated with AD (Guerreiro, et al., N. Engl. J. Med. 368:117-127 (2013), Jonsson, et al., N. Engl. J. Med. 368:117-127 (2013)), homozygous variants in TREM2 or its binding partner DAP12/TYROBP cause polycystic lipomembranousosteodysplasia with sclerosing leukoencephalopathy (PLOSL), also known as Nasu-Hakola disease (NHD). NHD is a rare autosomal-recessive early-onset dementia characterized by behavioral changes and cognitive decline, with or without pathological bone fractures (Guerreiro, et al., JAMA Neurol. 70:78-84 (2013), Paloneva, et al., Am. J. Hum. Genet. 71:656-662 (2002)).

The mechanism by which TREM2 contributes to neurodegeneration remains obscure. Furthermore, studies investigating the impact of TREM2 signaling on the inflammatory response have produced contradictory results, demonstrating either an anti-inflammatory or a pro-inflammatory role for TREM2 (Jay, et al., J. Exp. Med. 212:287-295 (2015), Jay, et al., J. Neurosci. 37:637-647 (2017), Sieber, et al., PLos One 8:e52982 (2013), Turnbull, et al., J. Immunol 177:3520-3524 (2006)). Recent studies have identified a role for TREM2 in microglial survival (Wang, et al., Cell 160: 1061-1071 (2015)), as well as in regulating energy metabolism (Ulland, et al., Cell 170:649-663 (2017)). Several studies have pointed to a role for TREM2 in phagocytosis (Hsieh, et al., J. Neurochem. 109:1144-1156 (2009), Kawabori, et al., J. Neurosci. 35:3384-3396 (2015), Kleinberger, et al., Sci. Transl. Med. 6:243ra86 (2014), Takahashi, et al., J. Exp. Med. 201:647-657 (2005), Xiang, et al., EMBO Mol. Med. 8:992-1004 (2016)), while others have observed no effect (e.g., Wang, et al., Cell 160:1061-1071 (2015)). One possible explanation for some of these apparent inconsistencies could be related to the differential behavior of the immune system in rodents and humans (Smith and Dragunow, Trends Neurosci. 37:125-135 (2014) or differences in phagocytic materials.

Given the prevalence and lack of effective treatments for neurodegenerative disorders such as AD, superior detection and treatment reagents are necessary.

BRIEF SUMMARY OF THE INVENTION

Provided herein are agonistic and antagonistic monoclonal antibodies and antigen-binding fragments thereof capable of binding to the extracellular domain of TREM2. The antibodies and antigen-binding fragments thereof are capable of activating microglia expressing TREM2, thereby facilitating uptake of oligomeric beta amyloid and attenuating cognitive decline in tauopathy and amyloidopathy. Thus, the antibodies and antigen-binding fragments provided herein are useful for the detection and treatment of neurodegenerative diseases.

In one aspect, an antibody or antigen-binding fragment thereof capable of binding human Triggering Receptor Expressed on Myeloid Cells 2 (TREM2) comprises a complementary determining region (CDR) H1 comprising the amino acid sequence set forth in SEQ ID NO:1, a CDR H2 comprising the amino acid sequence set forth in SEQ ID NO:2, a CDR H3 comprising the amino acid sequence set forth in SEQ ID NO:3, a CDR L1 comprising the amino acid sequence set forth in SEQ ID NO:4, a CDR L2 comprising the amino acid sequence set forth in SEQ ID NO:5, and a CDR3 L3 comprising the amino acid sequence set forth in SEQ ID NO:6.

In one aspect, the antibody or antigen-binding fragment thereof comprises a VH comprising the amino acid sequence of SEQ ID NO:7. In one aspect, the antibody or antigen-binding fragment thereof comprises a VL comprising the amino acid sequence of SEQ ID NO:8. In one aspect, the antibody or antigen-binding fragment thereof comprises a VH comprising the amino acid sequence of SEQ ID NO:7 and a VL comprising the amino acid sequence of SEQ ID NO:8.

In one aspect, an antibody or antigen-binding fragment thereof capable of binding human TREM2 comprises a VH and a VL, wherein the VH comprises the amino acid sequence set forth in SEQ ID NO:7.

In one aspect, an antibody or antigen-binding fragment thereof capable of binding human TREM2 comprises a VH and a VL, wherein the VH comprises the same amino acid sequence as the VH of the antibody produced by the CGX-c1 hybridoma deposited at the ATCC® as deposit number PTA-125491 on Nov. 14, 2018.

In one aspect, an antibody or antigen-binding fragment thereof capable of binding human TREM2 comprises a VH and a VL, wherein the VL comprises the amino acid sequence set forth in SEQ ID NO:8.

In one aspect, an antibody or antigen-binding fragment thereof capable of binding human TREM2 comprises a VH and a VL, wherein the VL comprises the same amino acid sequence as the VL of the antibody produced by the CGX-c1 hybridoma deposited at the ATCC® as deposit number PTA-125491 on Nov. 14, 2018.

In one aspect, an antibody or antigen-binding fragment thereof capable of binding human TREM2, comprises a VH comprising an amino acid sequence at least 85% identical to the amino acid sequence SEQ ID NO:7 and a VL comprising an amino acid sequence at least 85% identical to the amino acid sequence of SEQ ID NO:8.

In one aspect, the antibody or antigen-binding fragment thereof comprises a VH comprising an amino acid sequence that is at least 85% identical to the amino acid sequence of SEQ ID NO:7. In one aspect, the antibody or antigen-binding fragment thereof comprises a VH comprising an amino acid sequence that is at least 90% identical to the amino acid sequence of SEQ ID NO:7. In one aspect, the antibody or antigen-binding fragment thereof comprises a VH comprising an amino acid sequence that is at least 95% identical to the amino acid sequence SEQ ID NO:7. In one aspect, the antibody or antigen-binding fragment thereof comprises a VH comprising an amino acid sequence that is at least 98% identical to the amino acid sequence of SEQ ID NO:7. In one aspect, the antibody or antigen-binding fragment thereof comprises a VH comprising an amino acid sequence that is at least 99% identical to the amino acid sequence of SEQ ID NO:7.

In one aspect, the antibody or antigen-binding fragment thereof comprises a VL comprising an amino acid sequence that is at least 85% identical to the amino acid sequence of SEQ ID NO:8. In one aspect, the antibody or antigen-binding fragment thereof comprises a VL comprising an amino acid sequence that is at least 90% identical to the amino acid sequence of SEQ ID NO:8. In one aspect, the antibody or antigen-binding fragment thereof comprises a VL comprising an amino acid sequence that is at least 95% identical to the amino acid sequence of SEQ ID NO:8. In one aspect, the antibody or antigen-binding fragment thereof comprises a VL comprising an amino acid sequence that is at least 98% identical to the amino acid sequence of SEQ ID NO:8. In one aspect, the antibody or antigen-binding fragment thereof comprises a VL comprising an amino acid sequence that is at least 99% identical to the amino acid sequence of SEQ ID NO:8.

In one aspect, the antibody or antigen-binding fragment comprises a VH comprising the same amino acid sequence as the VH of the antibody produced by the CGX-c1 hybridoma deposited at the ATCC® as deposit number PTA-125491 on Nov. 14, 2018. In one aspect, the antibody or antigen-binding fragment comprises a VL comprising the same amino acid sequence as the VL of the antibody produced by the CGX-c1 hybridoma deposited at the ATCC® as deposit number PTA-125491 on Nov. 14, 2018. In one aspect, the antibody comprises a VH comprising the same amino acid sequence as the VH of the antibody produced by the CGX-c1 hybridoma deposited at the ATCC® as deposit number PTA-125491 on Nov. 14, 2018, and a VL comprising the same amino acid sequence as the VL of the antibody produced by the CGX-c1 hybridoma deposited at the ATCC® as deposit number PTA-125491 on Nov. 14, 2018.

In one aspect, the antibody or antigen-binding fragment further comprises a heavy chain constant region. In one aspect, the heavy chain constant region is a human IgG heavy chain constant region. In one aspect, the heavy chain constant region is a human $IgG_1$ heavy chain constant region. In one aspect, the heavy chain constant region is a human $IgG_4$ heavy chain constant region.

In one aspect, the antibody or antigen-binding fragment further comprises a light chain constant region. In one aspect, the light chain constant region is a human IgGκ light chain constant region.

In one aspect, the antibody or antigen-binding fragment thereof comprises a heavy chain comprising the same amino acid sequence as the heavy chain of the antibody produced by the CGX-c1 hybridoma deposited at the ATCC® as deposit number PTA-125491 on Nov. 14, 2018. In one aspect, the antibody or antigen-binding fragment thereof comprises a light chain comprising the same amino acid sequence as the light chain of the antibody produced by the CGX-c1 hybridoma deposited at the ATCC® as deposit number PTA-125491 on Nov. 14, 2018. In one aspect, the antibody comprises a heavy chain comprising the same amino acid sequence as the heavy chain of the antibody produced by the CGX-c1 hybridoma deposited at the ATCC® as deposit number PTA-125491 on Nov. 14, 2018, and a light chain comprising the same amino acid sequence as the light chain of the antibody produced by the CGX-c1 hybridoma deposited at the ATCC® as deposit number PTA-125491 on Nov. 14, 2018.

In one aspect, an antibody or antigen-binding fragment thereof that specifically binds to human TREM2 comprises the CDRH1, CDR H2, CDR H3, CDR L1, CDRL2, and CDR L3 of an antibody comprising a VH comprising the amino acid sequence of SEQ ID NO:7 and a VL comprising the amino acid sequence of SEQ ID NO:8. In one aspect, the CDRs are the Kabat-defined CDRs, the Chothia-defined CDRs, or the AbM-defined CDRs.

In one aspect, the antibody or antigen-binding fragment thereof is capable of binding to the extracellular domain of TREM2. In one aspect, the affinity constant (KD) of the antibody or antigen-binding fragment thereof for binding to the extracellular domain of human TREM2 is about 5 nM to about 7 nM as measured by surface plasmon resonance. In one aspect, the affinity constant (KD) of the antibody or antigen-binding fragment thereof for binding to the extracellular domain of human TREM2 is about 5.5 nM to about 6 nM as measured by surface plasmon resonance.

In one aspect, the antibody or antigen-binding fragment thereof is capable of binding mouse TREM2. In one aspect, the affinity constant (KD) of the antibody or antigen-binding fragment thereof for binding to mouse TREM2 is about 15 nM to about 20 nM as measured by surface plasmon resonance. In one aspect, the affinity constant (KD) of the antibody or antigen-binding fragment thereof for binding to mouse TREM2 is no more than 4 times the affinity constant (KD) of the antibody or antigen-binding fragment thereof for binding to the extracelluar domain of human TREM2.

In one aspect, the antibody or antigen-binding fragment thereof is capable of binding soluble TREM2 in supernatants of TREM2-transfected HEK293T cells. In one aspect, the antibody or antigen-binding fragment thereof is capable of binding soluble TREM2 in the cerebral spinal fluid (CSF) of patients with Alzheimer's Disease (AD). In one aspect, the antibody or antigen-binding fragment thereof is capable of binding soluble TREM2 in the serum of patients with AD.

In one aspect, the antibody or antigen-binding fragment thereof does not increase tumor necrosis factor (TNF)-alpha expression in non-stimulated peripheral blood mononuclear cells (PBMCs). In one aspect, the antibody or antigen-binding fragment thereof increases TNF-alpha expression in microglia exposed to amyloid beta. In one aspect, the antibody or antigen-binding fragment thereof increases the uptake of beta amyloid by microglia. In one aspect, the antibody or antigen-binding fragment thereof is capable of inhibiting neuroinflammation. In one aspect, the antibody or antigen-binding fragment thereof is capable of inhibiting increased TNF-alpha expression induced by intracerebral injection of soluble TREM2. In one aspect, the antibody or antigen-binding fragment thereof is capable of inhibiting increased interleukin (IL)-6 expression induced by intracerebral injection of soluble TREM2. In one aspect, the antibody or antigen-binding fragment thereof is capable of inhibiting increased interferon (INF)-gamma expression induced by intracerebral injection of soluble TREM2. In one aspect, the antibody or antigen-binding fragment thereof is capable of decreasing TNF-alpha expression in 5×FAD mice. In one aspect, the antibody or antigen-binding fragment thereof is capable of decreasing IL-6 expression in 5×FAD mice. In one aspect, the antibody or antigen-binding fragment thereof is capable of decreasing IL-1b expression in 5×FAD mice. In one aspect, the antibody or antigen-binding fragment thereof is capable of decreasing the number of amyloid plaques in 5×FAD mice.

In one aspect, the antibody or antigen-binding fragment thereof is capable of improving cognition. In one aspect, the antibody or antigen-binding fragment thereof is capable of attenuating cognitive decline in 5×FAD mice. In one aspect, the antibody or antigen-binding fragment thereof is capable of attenuating cognitive decline in hTau.K257T/P301A mice. In one aspect, cognition is measured by a Morris Water Maze assay. In one aspect, cognition is measure by a Novel Object Recognition assay.

In one aspect, the antibody or antigen-binding fragment thereof is capable of reducing soluble TREM2 in CSF. In one aspect, the antibody or antigen-binding fragment thereof is capable of reducing soluble TREM2 in CSF of 5×FAD mice. In one aspect, the antibody or antigen-binding fragment thereof is capable of reducing soluble TREM2 in serum. In one aspect, the antibody or antigen-binding fragment thereof is capable of reducing soluble TREM2 in serum of 5×FAD mice.

In one aspect, an isolated antibody or antigen-binding fragment thereof binds to the same epitope of human TREM2 as an antibody or antigen-binding fragment thereof provided herein.

In one aspect, an isolated antibody or antigen-binding fragment thereof competitively inhibits binding of an antibody or antigen-binding fragment thereof provided herein to human TREM2.

In one aspect, the antibody or antigen-binding fragment thereof binds to at least one amino acid in amino acids 34-40 of SEQ ID NO:9 and at least one amino acid in amino acids 134-150 of SEQ ID NO:9. In one aspect, the binding of the antibody or antigen-binding fragment thereof to TREM2 is disrupted by the presence of a peptide comprising amino acids 34-40 of SEQ ID NO:9 and/or by the presence of a peptide comprising amino acids 134-150 of SEQ ID NO:9.

In one aspect, the antibody or antigen-binding fragment thereof is a full length antibody. In one aspect, the antibody or antigen-binding fragment thereof is an antigen-binding fragment. In one aspect, the antigen-binding fragment comprises a Fab, Fab', F(ab')$_2$, single chain Fv(scFv), disulfide linked Fv, V-NAR domain, IgNar, intrabody, IgGΔCH2, minibody, F(ab')$_3$, tetrabody, triabody, diabody, single domain antibody, DVD-Ig, Fcab, mAb$^2$, (scFv)$_2$, or scFv-Fc.

In one aspect, the antibody or antigen-binding fragment thereof is isolated. In one aspect, the antibody or antigen-binding fragment thereof is a monoclonal antibody.

In one aspect, the antibody or antigen-binding fragment thereof further comprises a detectable label.

In one aspect, an isolated polynucleotide comprises a nucleic acid molecule encoding the heavy chain variable region or heavy chain of an antibody or antigen-binding fragment thereof provided herein. In one aspect, the nucleic acid molecule encodes a VH comprising the amino acid sequence of SEQ ID NO:7. In one aspect, the nucleic acid molecule comprises (i) the same nucleotide sequence as the VH-encoding nucleotide sequence in the CGX-c1 hybridoma deposited at the ATCC® as deposit number PTA-125491 on Nov. 14, 2018, or (ii) the same nucleotide as the heavy chain-encoding nucleotide sequence in the CGX-c1 hybridoma deposited at the ATCC® as deposit number PTA-125491 on Nov. 14, 2018.

In one aspect, an isolated polynucleotide comprises a nucleic acid molecule encoding the light chain variable region or light chain of an antibody or antigen-binding fragment thereof provided herein. In one aspect, the nucleic acid molecule encodes a VL comprising the amino acid sequence of SEQ ID NO:8. In one aspect, the nucleic acid molecule comprises (i) the same nucleotide sequence as the VL-encoding nucleotide sequence in the CGX-c1 hybridoma deposited at the ATCC® as deposit number PTA-125491 on Nov. 14, 2018, or (ii) the same nucleotide sequence as the light chain-encoding nucleotide sequence in the CGX-c1 hybridoma deposited at the ATCC® as deposit number PTA-125491 on Nov. 14, 2018.

In one aspect, an isolated polynucleotide comprises a nucleic acid molecule encoding the heavy chain variable region or heavy chain of an antibody or antigen-binding fragment thereof provided herein and the light chain variable region or light chain of an antibody or antigen-binding fragment thereof provided herein.

In one aspect, an isolated vector comprises a polynucleotide provided herein.

In one aspect, a host cell comprises a polynucleotide provided herein, a vector provided herein, or a first vector comprising a first polynucleotide provided herein (e.g., encoding a heavy chain variable region or a heavy chain) and a second vector comprising a second polynucleotide provided herein (e.g., encoding a light chain variable region or a light chain). In one aspect, the host cell is selected from the group consisting of CHO, HEK-293T, HeLa and BHK cells, optionally wherein the CHO cell is a CHO-K1SP cell.

In one aspect, a method of producing an antibody or antigen-binding fragment thereof that binds to human TREM2 comprises culturing a host cell provided herein so that the nucleic acid molecule is expressed and the antibody or antigen-binding fragment thereof is produced. In one aspect, an isolated antibody or antigen-binding fragment thereof provided herein is produced by such a method.

In one aspect, a pharmaceutical composition comprises an antibody or antigen-binding fragment thereof provided herein and a pharmaceutically acceptable excipient.

In one aspect, a method for detecting TREM2 in a sample comprises contacting the sample with an antibody or antigen-binding fragment thereof provided herein. In one aspect, the TREM2 is soluble TREM2. In one aspect, the sample is obtained from a subject suspected of having a neurodegenerative disease or disorder. In one aspect, the sample is obtained from a subject who has been diagnosed with a neurodegenerative disease or disorder. In one aspect, the sample is a cerebral spinal fluid (CSF) sample, a serum sample, or a brain biopsy tissue.

In one aspect, a method for increasing the uptake of beta amyloid by an immune cell exposed to beta amyloid comprises contacting the immune cell with an antibody or antigen-binding fragment thereof provided herein or a pharmaceutical composition provided herein. In one aspect, the immune cell is a microglia. In one aspect, the contacting occurs in vitro. In one aspect, the contacting occurs in a subject.

In one aspect, a method of attenuating neuroinflammation in a subject comprises administering to the subject an antibody or antigen-binding fragment thereof provided herein or a pharmaceutical composition provided herein.

In one aspect, a method of reducing the number of amyloid plaques in a subject comprises administering to the subject an antibody or antigen-binding fragment thereof provided herein or a pharmaceutical composition provided herein.

In one aspect, a method of improving cognition in a subject comprises administering to the subject an antibody or antigen-binding fragment thereof provided herein or a pharmaceutical composition provided herein.

In one aspect, a method of attenuating cognitive dysfunction in a subject comprises administering to the subject an antibody or antigen-binding fragment thereof provided herein or a pharmaceutical composition provided herein.

In one aspect, a method of reducing soluble TREM2 in a subject comprises administering to the subject an antibody or antigen-binding fragment thereof provided herein or a pharmaceutical composition provided herein.

In one aspect, a method of treating or preventing a neurodegenerative disease or disorder in a subject comprises administering to the subject an antibody or antigen-binding fragment thereof provided herein or a pharmaceutical composition provided herein.

In one aspect, the neurodegenerative disease or disorder is AD. In one aspect, the neurodegenerative disease or disorder is an amyloidosis. In one aspect, the neurodegenerative disease or disorder is a tauopathy.

In one aspect, the administration is intraperitoneal (IP) administration.

In one aspect, the subject is a human.

In one aspect, a kit comprises an antibody or antigen-binding fragment thereof provided herein or a pharmaceutical composition provided herein and a) a detection reagent, b) TREM2 antigen, c) a notice that reflects approval for use or sale for human administration, or d) a combination thereof.

BRIEF DESCRIPTION OF THE DRAWINGS/FIGURES

FIG. 1 is a Western blot showing that murine IgG antibodies CGX101, Ab-T2, Ab-T3, Ab-T4, and Ab-T5 recognize TREM2 expressed on transfected HEK293T cells. "HEK-hTREM2-GFP" indicates lanes with HEK293T cells transfected with sequences encoding human TREM2. "HEK control" indicates lanes with HEK293T cells that were not transfected with TREM2-encoding sequences, and "HEK-GFP" indicates lanes with cells transfected with a reporter gene. (See Example 1.)

Figure 6:
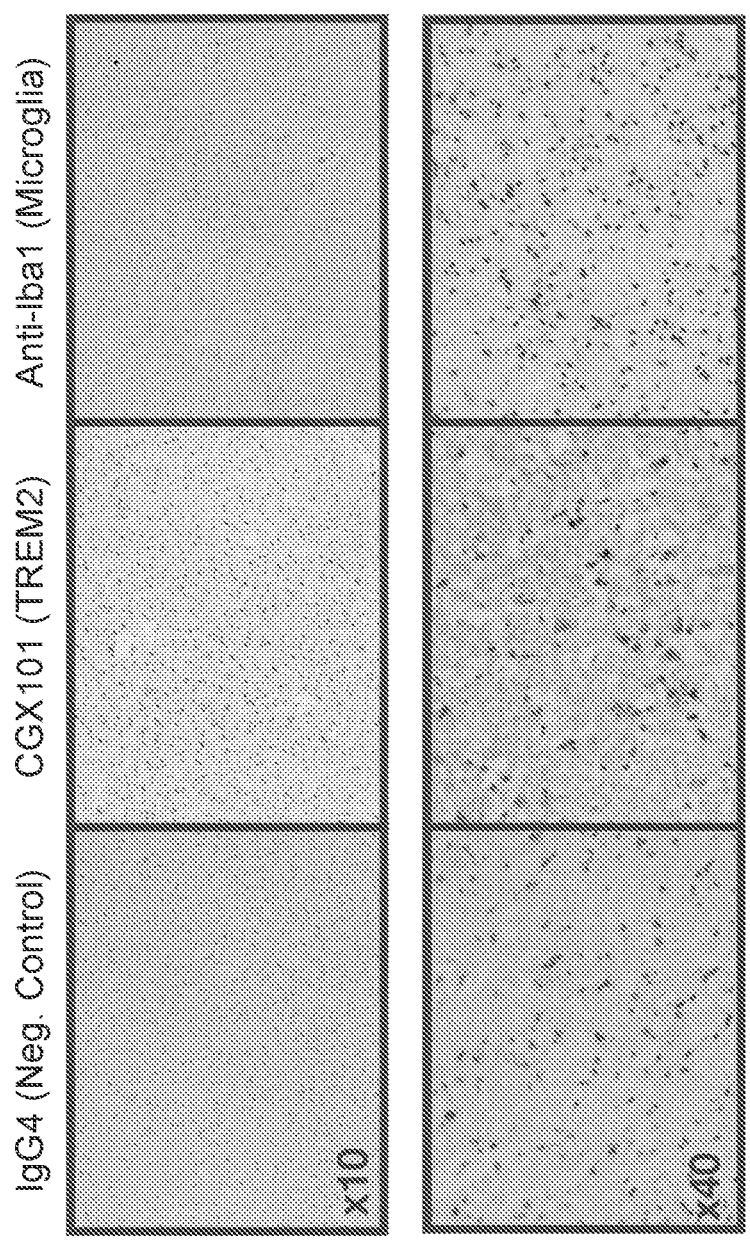

FIG. 6 shows immunohistochemical staining of CGX101, an IgG4 antibody (negative control), and an anti-Iba1 antibody to human brain tissue samples from AD patients. Iba1 indicates the presence of microglia. CGX101 robustly recognizes TREM2 in AD brains and co-localizes with resident microglia. (See Example 5.)

Figure 7:
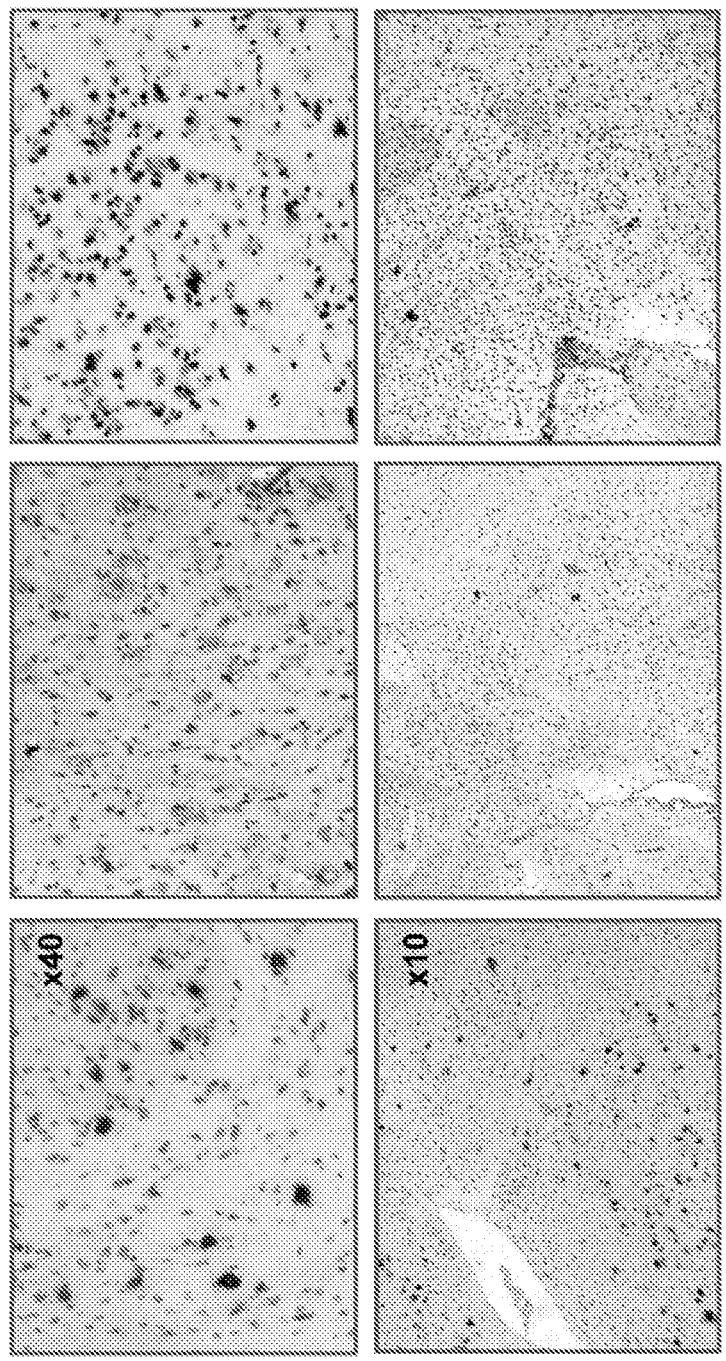

FIG. 7 shows immunohistochemical staining of CGX101, an anti-beta amyloid antibody, and an anti-Iba1 antibody to brain tissue samples from 5×FAD murine models of AD. CGX101 robustly recognizes TREM2 and co-localizes with resident microglia and beta amyloid plaques. (See Example 5.)

Figures 8A, 8B:
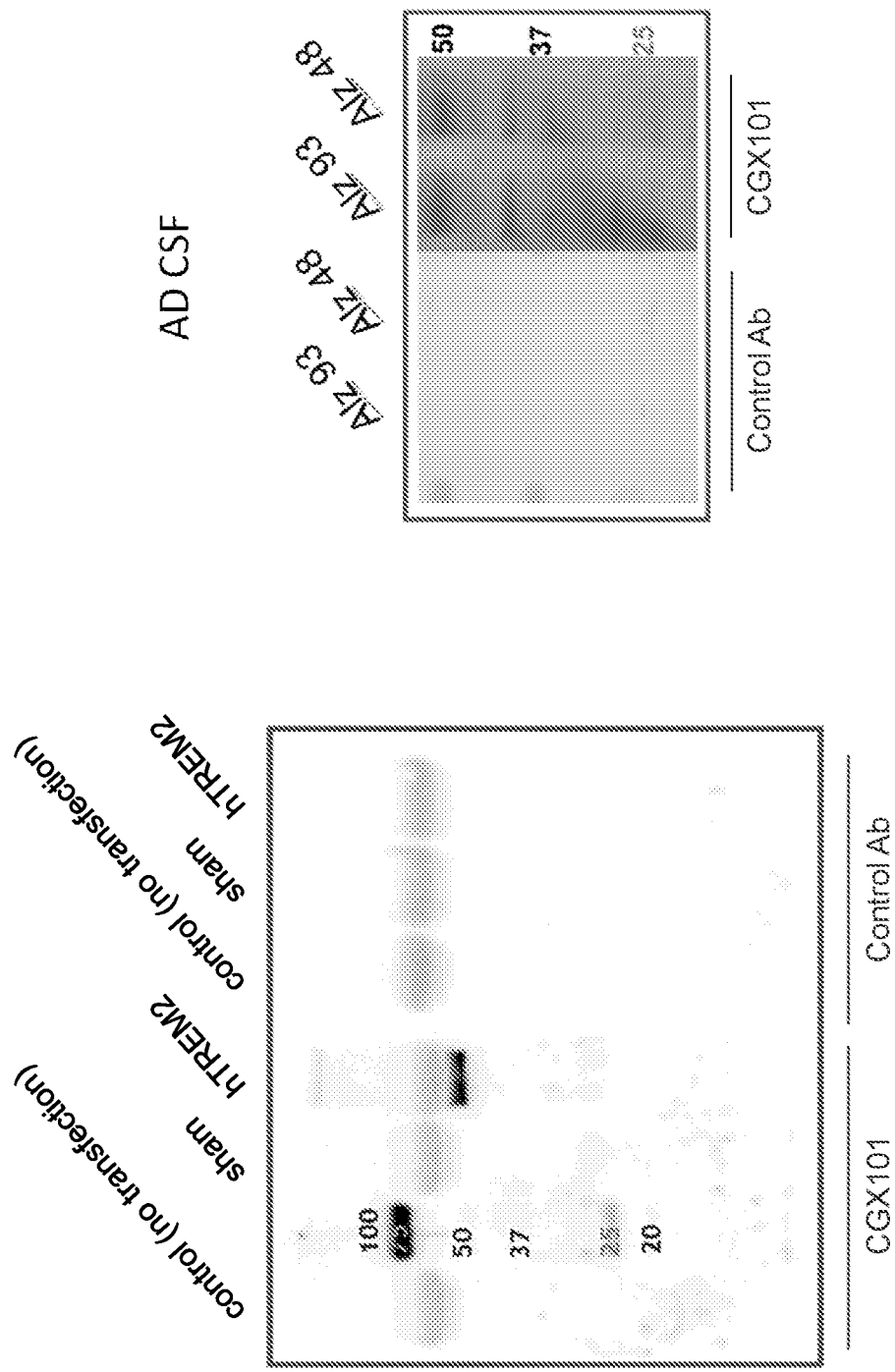

FIG. 8A is a Western blot showing CGX101 and a mouse IgG1 control antibody binding to soluble TREM2 in supernatants of human TREM2 transfected HEK293T cells. Transfected HEK293T cells with no DNA vector were used as "sham." (See Example 6.)

FIG. 8B is a Western blot showing CGX101 and a mouse IgG1 control antibody binding to soluble human TREM2 in the cerebral spinal fluid (CSF) of human AD patients. (See Example 6.)

Figure 9A:
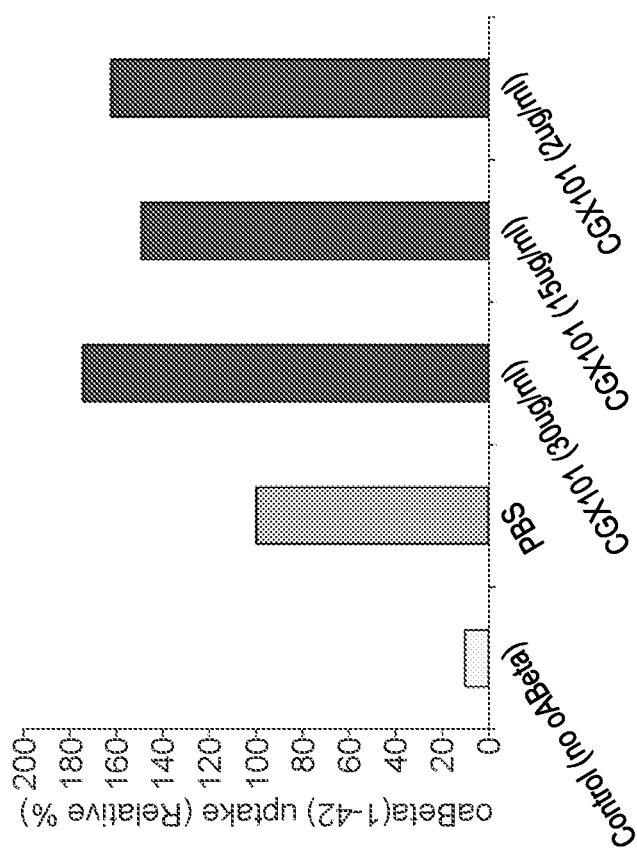

FIG. 9A is a graph showing that hCGX101 increases uptake of fluorescent oligomer beta amyloid in human microglia derived from differentiated human PBMCs. The y-axis reports the relative geometric mean (gMFI) as measured by flow cytometry. "Control" indicates no beta amyloid. (See Example 7.)

Figure 9B:
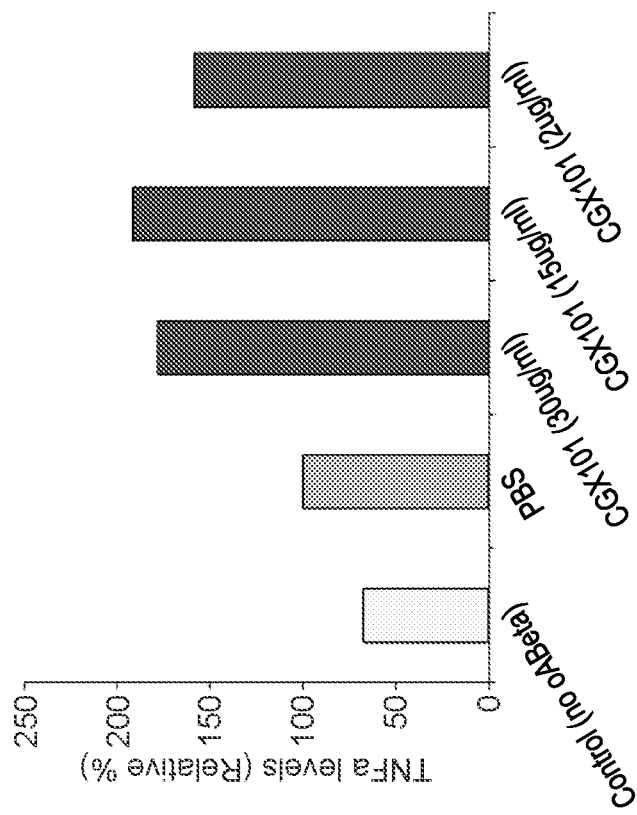

FIG. 9B is a graph showing that hCGX101 increases TNF-alpha protein levels, indicating acute microglial activation, in human microglia derived from differentiated human PBMCs. The y-axis reports the relative percent of TNF-alpha protein levels compared to cells treated with PBS as measured by ELISA assay. "Control" indicates no beta amyloid. (See Example 7.)

Figure 10:
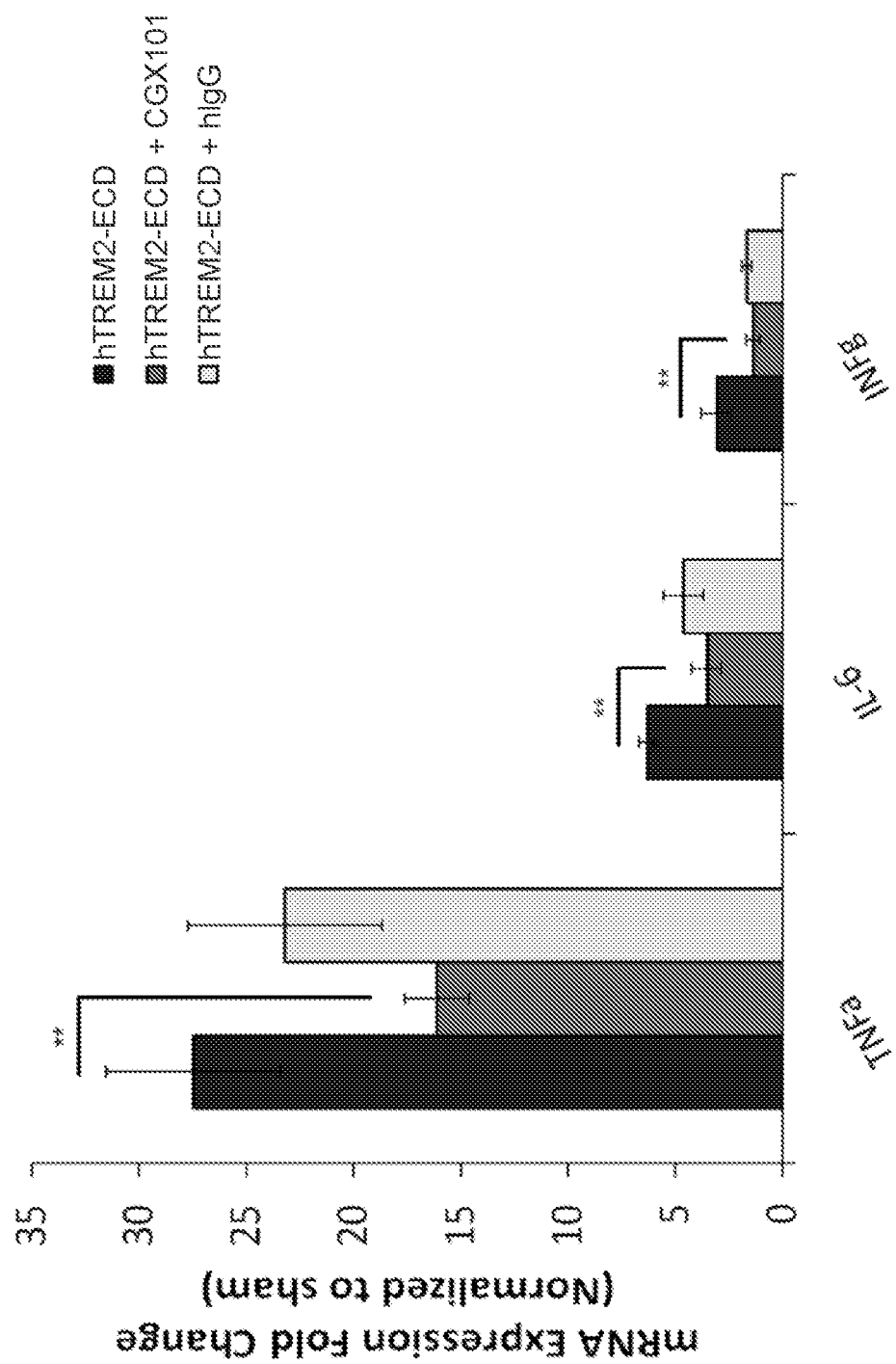

FIG. 10 is a graph showing that hCGX101 attenuates neuroinflammation induced by intra-cerebral injection of soluble TREM2 in vivo. (See Example 8.)

Figure 11:
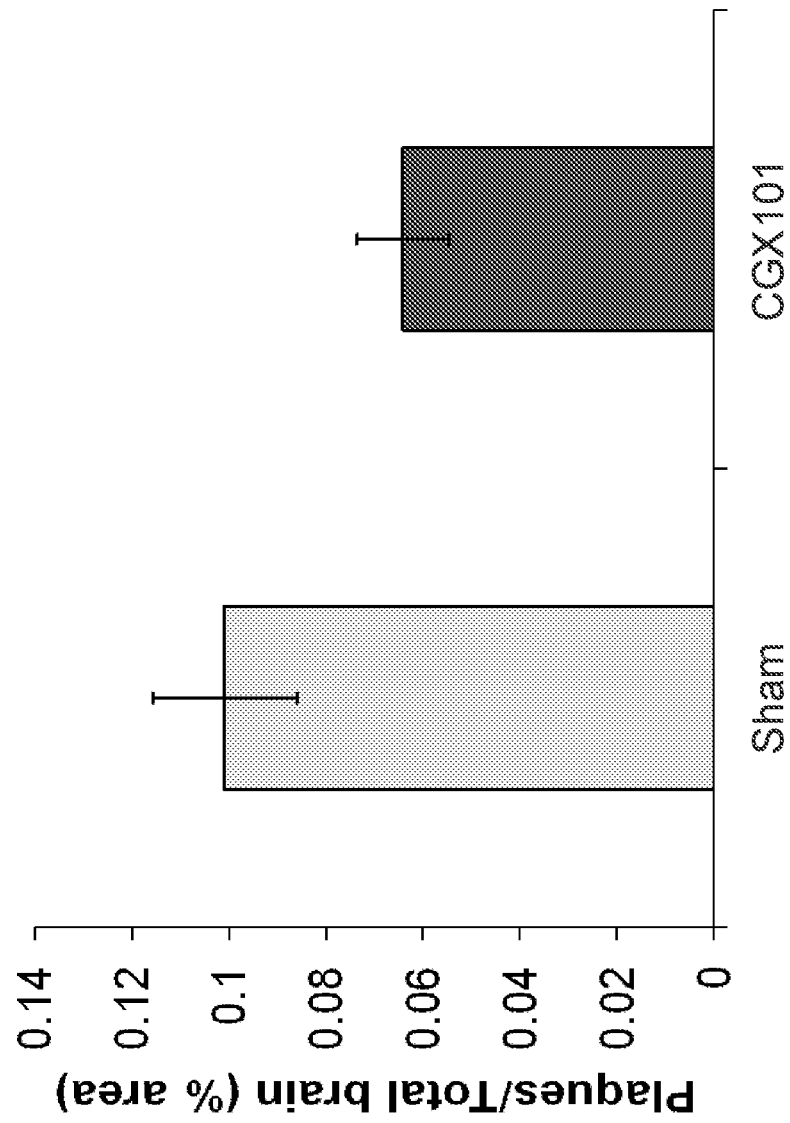

FIG. 11 is a graph showing the percentage of plaques in the total brain area of mice treated with hCGX101 or sham antibody. (See Example 9.)

FIG. 12A is a graph showing that two months of weekly intraperitoneal (IP) treatment with hCGX101 improves cognition in aged male 5×FAD mice as measured in the Morris Water Maze (MWM). "Control" refers to treatment with a vehicle solution. (See Example 10.)

FIG. 12B is a graph showing that two months of weekly IP treatment with hCGX101 reduces the number of amyloid plaques in aged male 5×FAD mice. "Control" refers to treatment with a vehicle solution. (See Example 10.)

Figure 13:
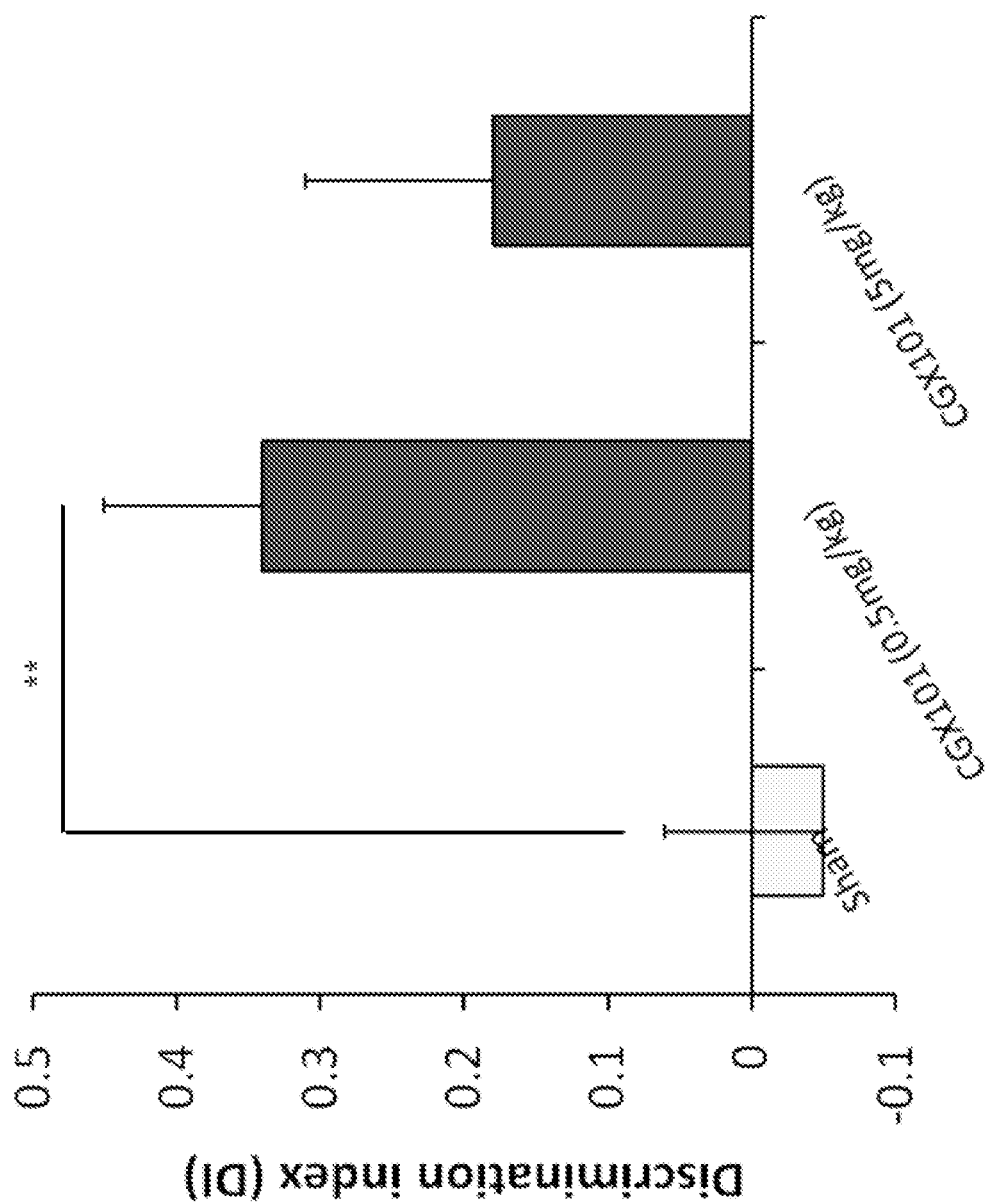

FIG. 13 is a graph showing that weekly IP treatment with hCGX101 effectively attenuates development of cognitive dysfunction in young 5×FAD mice. The y-axis reports the discrimination index (DI) for novel object recognition (NOR) testing after 8 weeks of treatment. The result can vary between +1 and −1, wherein a positive score indicates more time spent with the novel object. A negative score indicates more time spent with the familiar object, and a zero score indicates a null preference. ** indicates p<0.01. (See Example 11.)

Figure 14A:
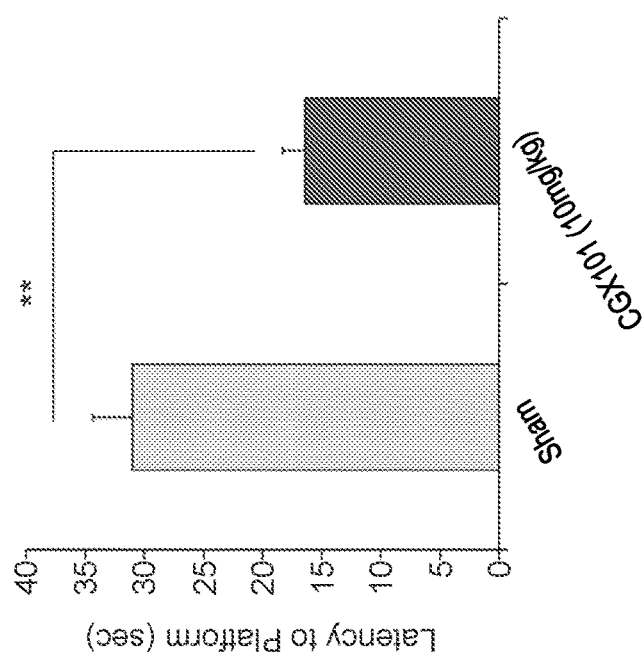

FIG. 14A is a graph showing that hCGX101 attenuates cognitive decline in hTau.K257T/P301A mice (a tauopathy AD model). Sham-treated mice showed more significant cognitive impairment as measured by an increase in the latency to platform in the MWM test as compared to hCGX101-treated mice. N=5 of each group. ** indicates p<0.02. (See Example 12.)

Figure 14B:

FIG. 14B shows a heat map average of group images showing the time mice treated with sham or hCGX101 spent in different areas of the MWM pool. (See Example 12.)

Figure 15A:
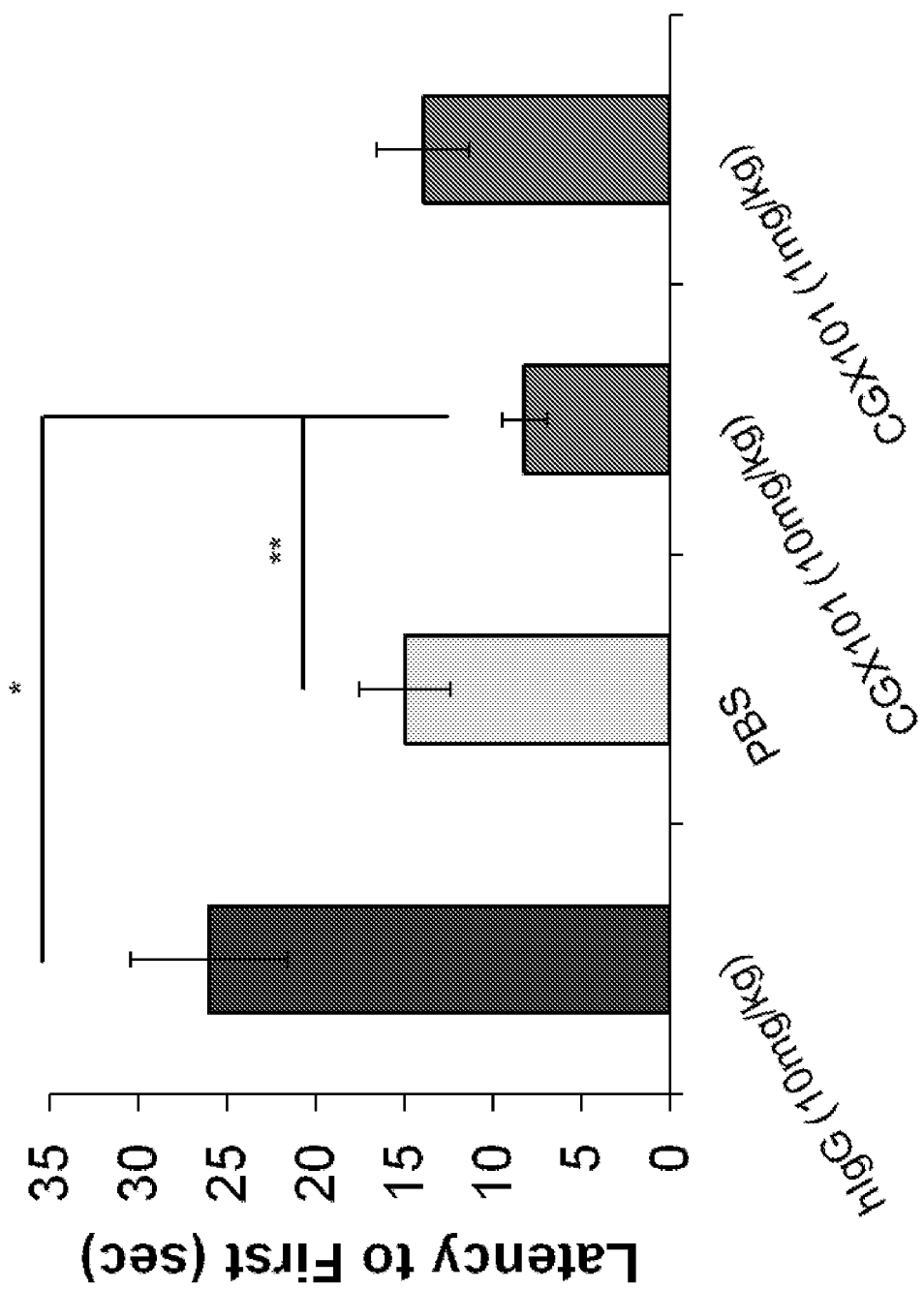

FIG. 15A is a graph showing that twice-monthly dosing of hCGX101 attenuates cognitive decline in five-month old female 5×FAD mice as compared to mice treated with sham (PBS) or human IgG (control) as measured by a latency to platform in the MWM test. * indicates p<0.02, and ** indicates p<0.05. (See Example 13.)

Figure 15B:
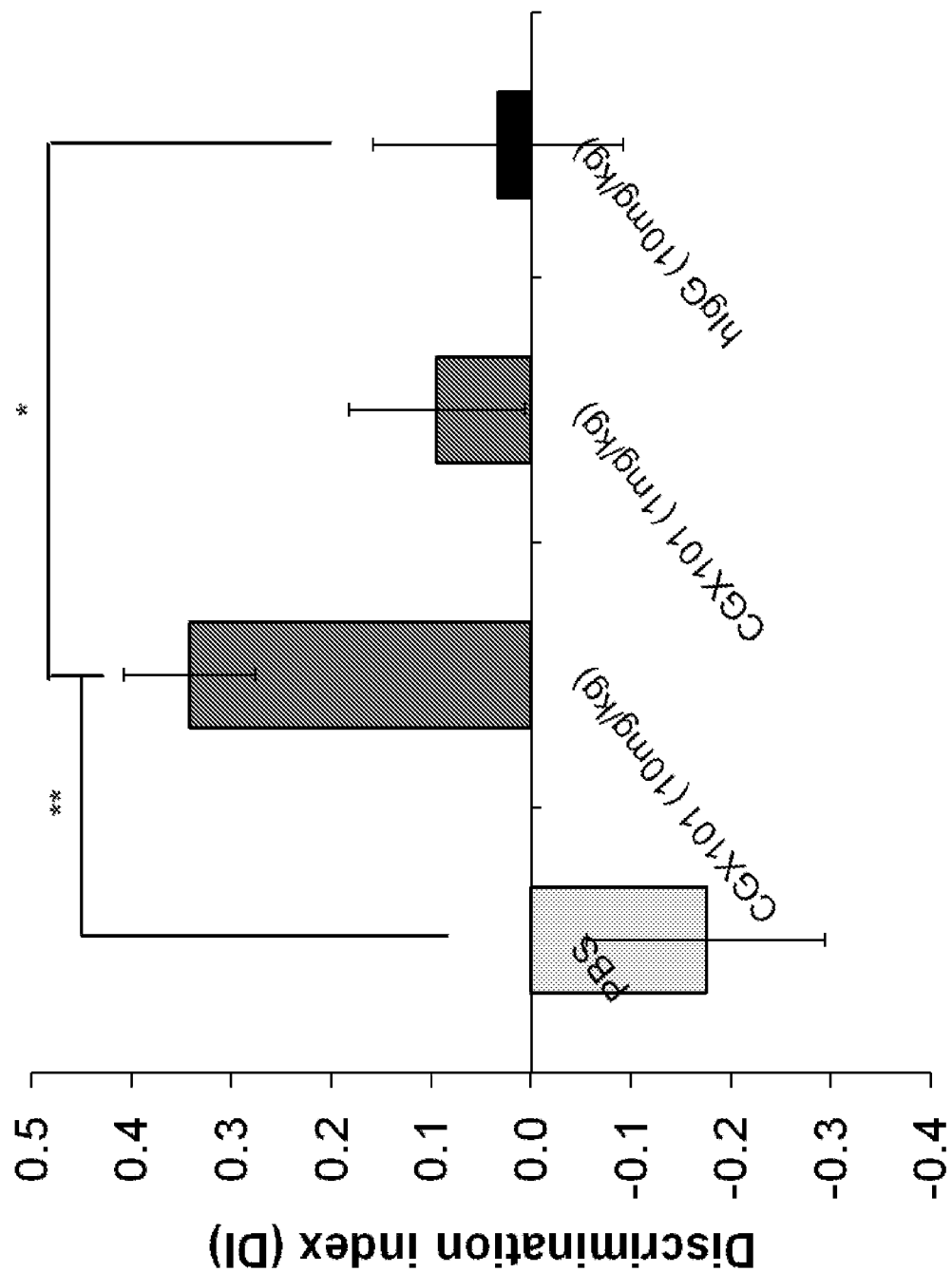

FIG. 15B is a graph showing that twice-monthly dosing of hCGX101 attenuates cognitive decline in five-month old female 5×FAD mice as compared to mice treated with sham (PBS) or human IgG (control) as measured by DI for the NOR testing session. * indicates p<0.01, and ** indicates p<0.005. (See Example 13.)

Figure 15C:
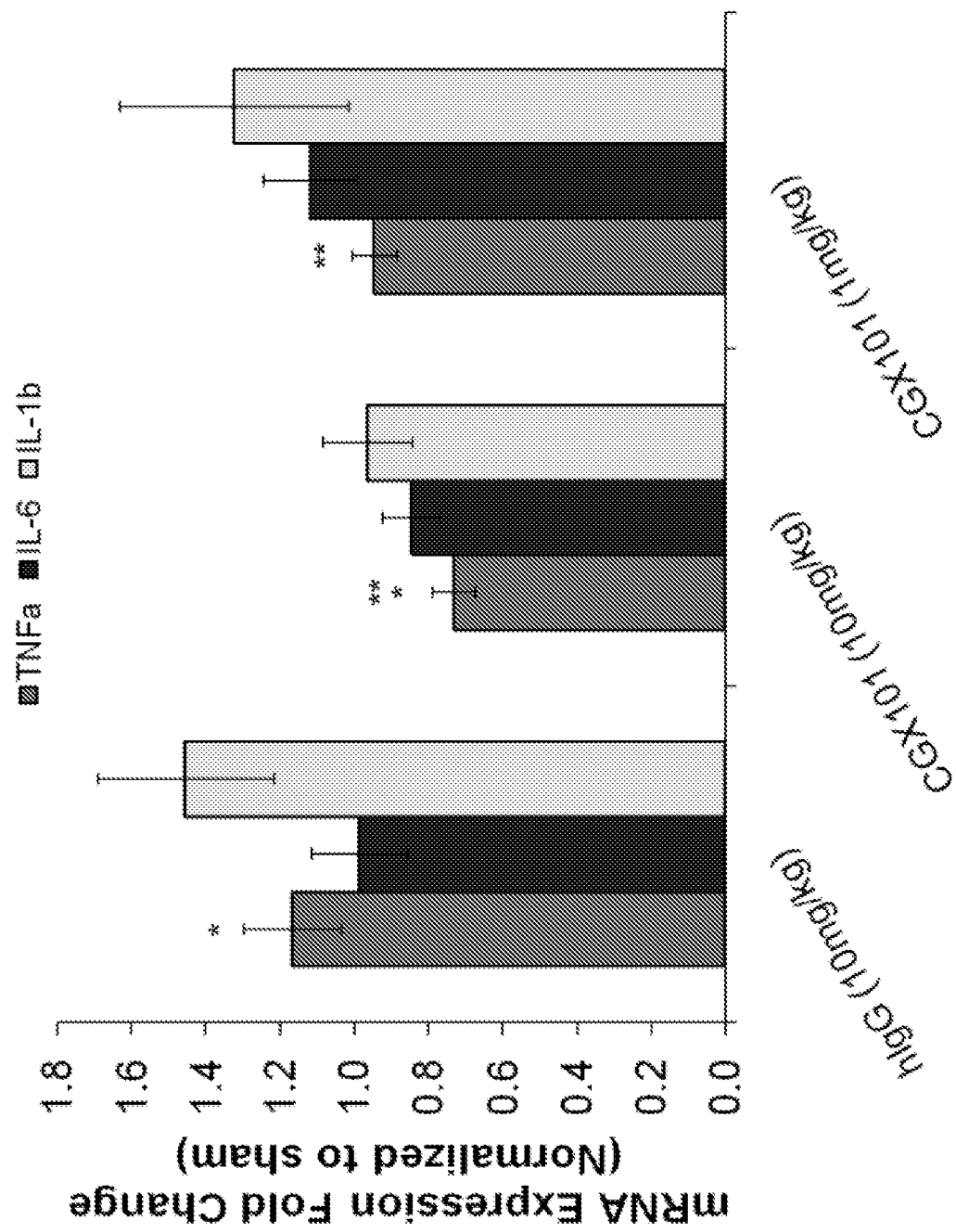

FIG. 15C is a graph showing that twice-monthly dosing of hCGX101 attenuates neuroinflammation in five-month old female 5×FAD mice as compared to mice treated with human IgG (control) as measured by change in mRNA expression levels of TNF-alpha, IL-1-beta, and IL-6 using TaqMan real-time PCR in purified brain homogenates. The y-axis reports the fold-change in expression compared to no treatment (sham). GAPDH was used as a housekeeping gene. N=9-10 animals per group. * indicates p<0.01, and ** indicates p<0.005. (See Example 13.)

Figure 16B:
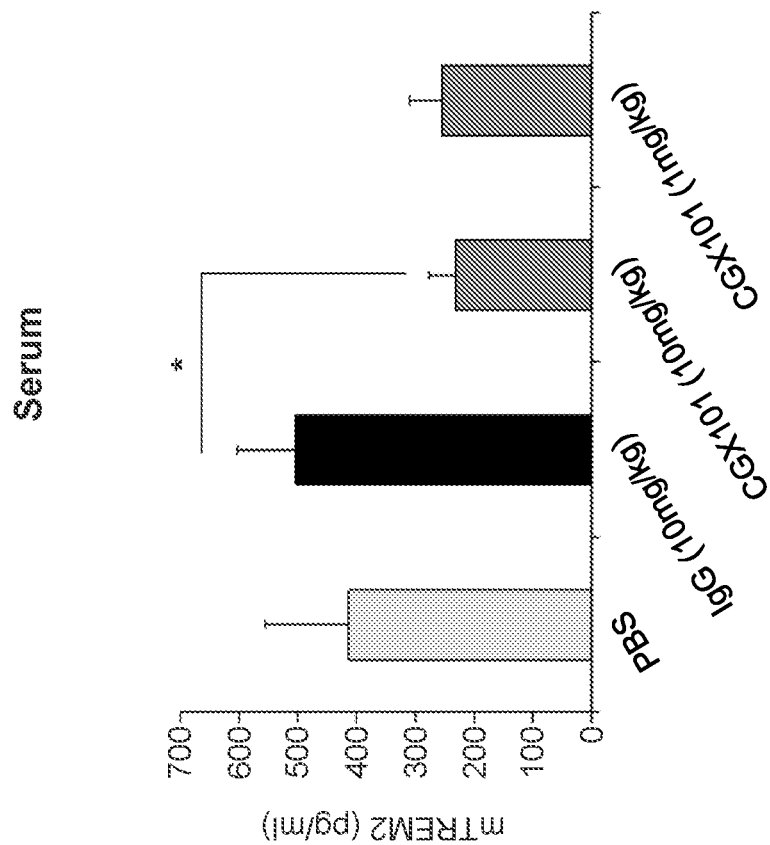
Figure 16A:
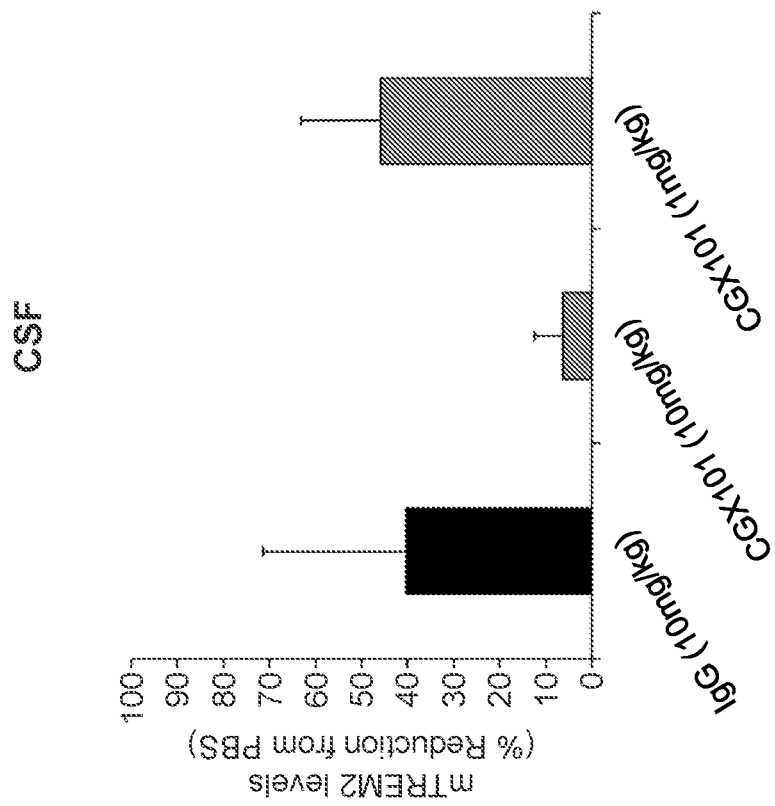

FIG. 16A is a graph showing that hCGX101 (1 and 10 mg/kg) results in a dose-dependent reduction of soluble TREM2 in the CSF of mice. An IgG antibody was used as a control. (See Example 14.)

FIG. 16B is a graph showing that hCGX101 (1 and 10 mg/kg) results in a dose-dependent reduction of soluble TREM2 in the serum of mice. An IgG antibody was used as a control, and PBS was injected into animals for a sham control. * indicates p<0.05. (See Example 14.)

Figure 17:
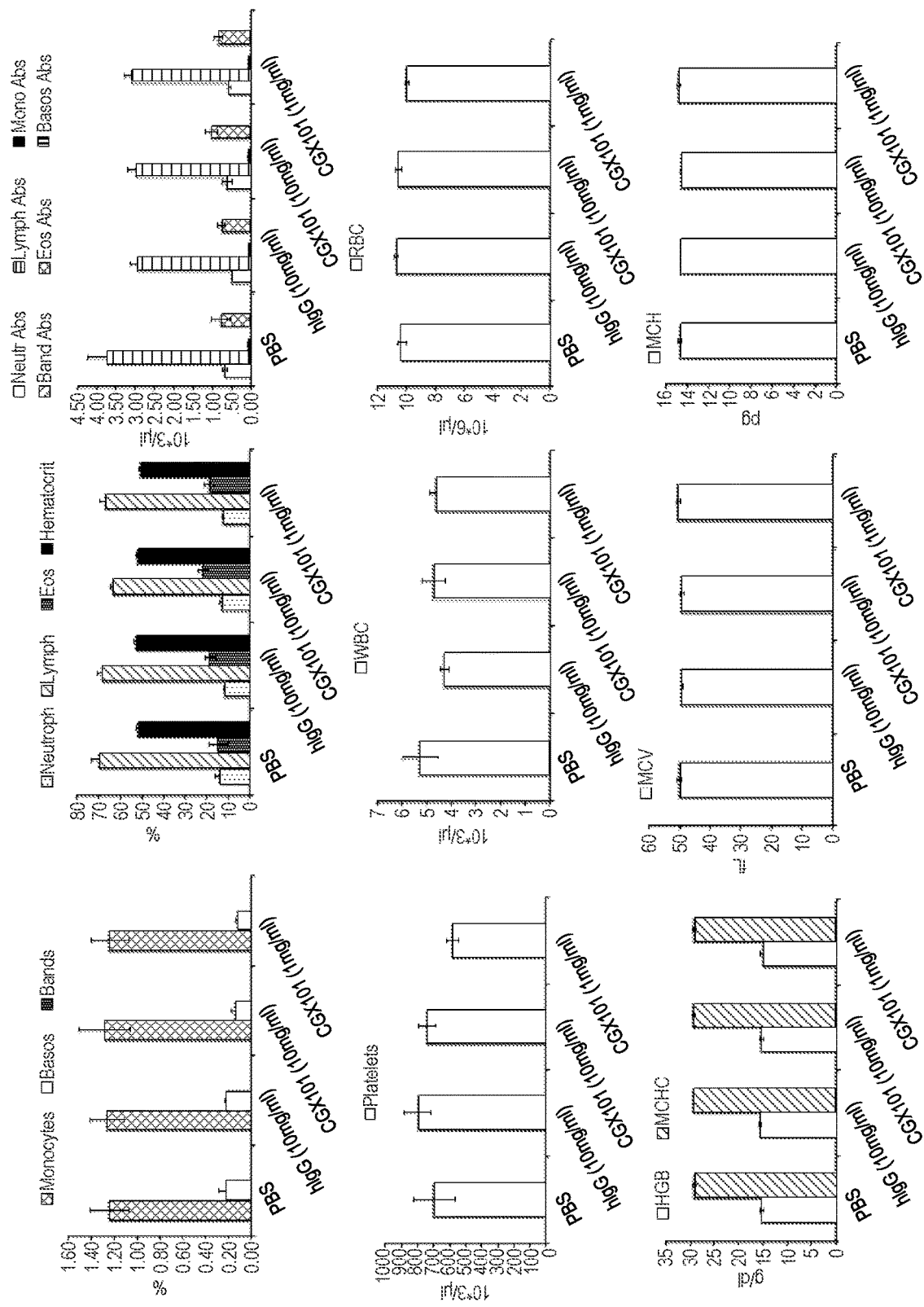

FIG. 17 is graphs showing that hCGX101 does not influence hematological or biochemical parameters in mice treated twice a month for 12 months. All of the data was within the accepted range and with no clinical significance. (See Example 15.)

Figure 18B:
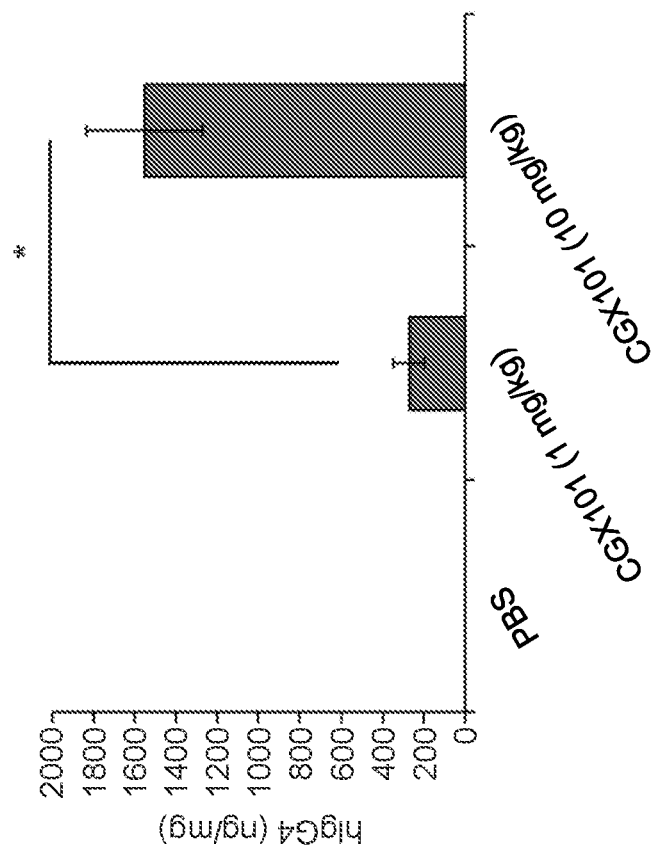
Figure 18A:
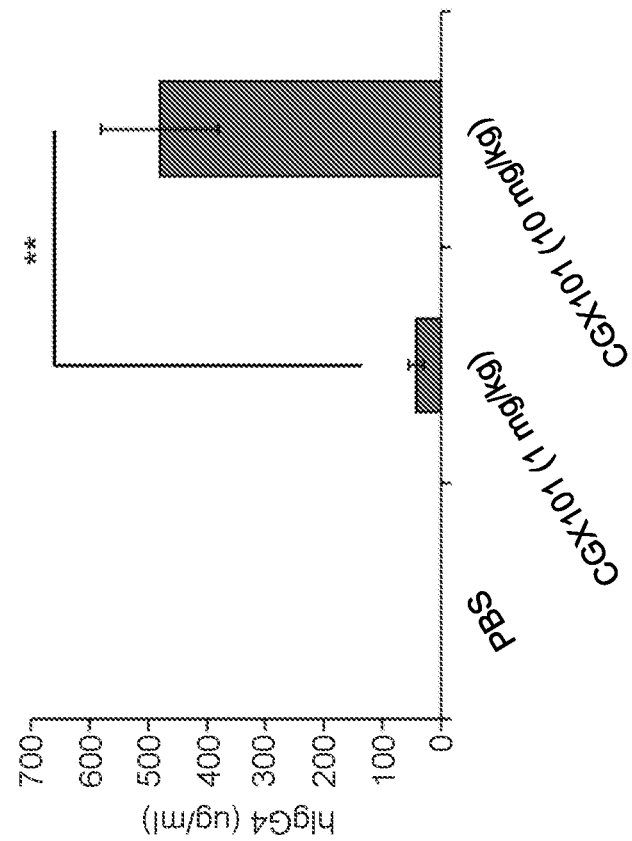

FIG. 18A is a graph showing the pharmacokinetics of hCGX101 ("hIgG4") in 5×FAD mice serum. ** indicates p<0.003. (See Example 16.)

FIG. 18B is a graph showing the pharmacokinetics of hCGX101 ("hIgG4") in 5×FAD mice brain tissue. * indicates p<0.002. (See Example 16.)

Figure 19:
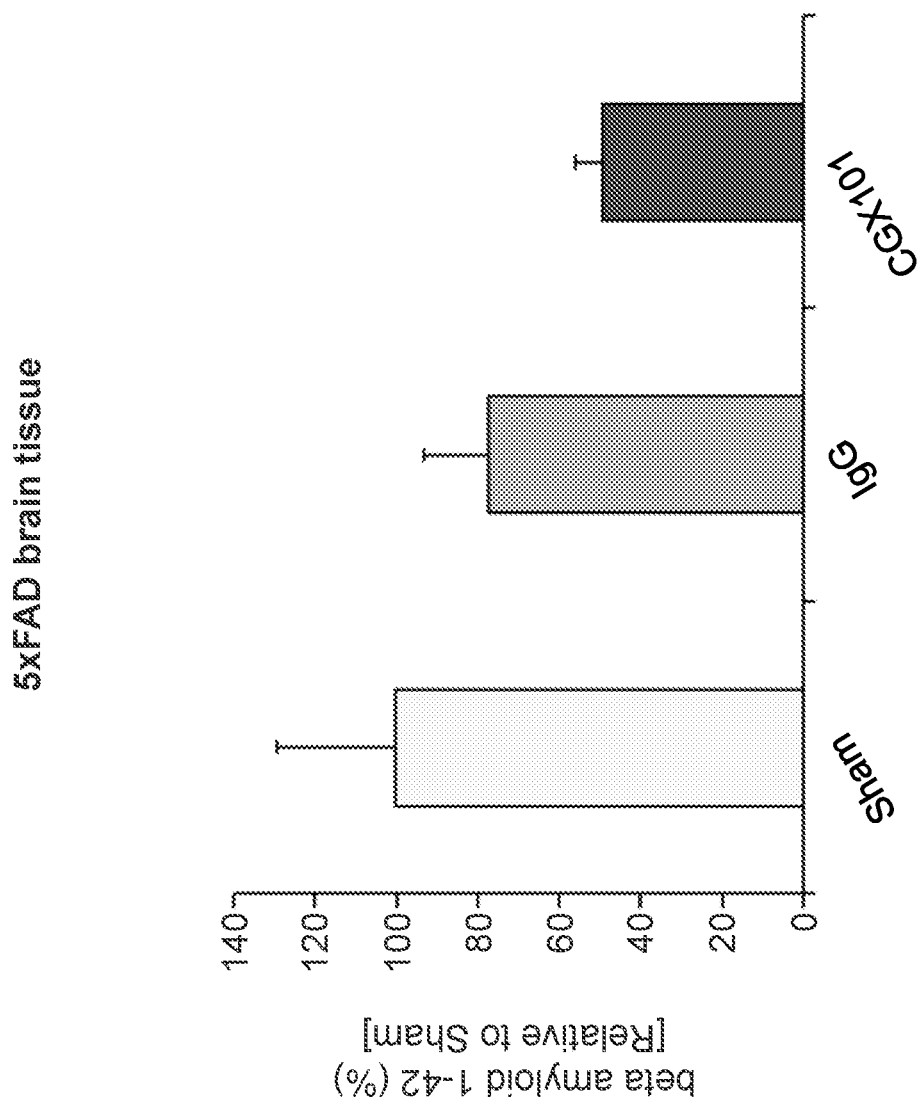

FIG. 19 is a graph showing the levels of human beta amyloid 1-42 in brain tissue from 5×FAD mice treated with a sham, an IgG antibody, or hCGX101. The levels are shown relative to the levels observed with the sham treatment.

DETAILED DESCRIPTION OF THE INVENTION

I. Definitions

As used herein, the terms "Triggering Receptor Expressed on Myeloid Cells 2" and "TREM2" are interchangeable and refer to mammalian TREM2 polypeptides including, but not limited to, wild-type and mutant TREM2 polypeptides. "TREM2" encompasses full-length, unprocessed TREM2 polypeptides as well as forms of TREM2 polypeptides that result from processing within the cell (e.g., soluble TREM2). As used herein, the term "human TREM2" refers to a polypeptide comprising amino acids 19-230 of SEQ ID NO:9. A "TREM2 polynucleotide," "TREM2 nucleotide," or "TREM2 nucleic acid" refer to a polynucleotide encoding TREM2.

Human TREM2:
MEPLRLLILLFV-TELSGAHNTTVFQGVAGQSLQVSCPYDSMKHWGR-RKAWCR QLGEKGPCQRVVSTHNLWLLSFLRRWNG-STAITDDTLGGTLTITLRNLQPHDAG LYQCQSLHG-SEADTLRKVLVEVLADPLDHRDAGDLWFPGESESFE-DAHVEHSIS RSLLEGEIPFPPTSILLLLACIFLIKILA-ASALWAAAWHGQKPGTHPPSELDCGHDP GYQLQTLPGLRDT (SEQ ID NO:9). The underlined amino acids (i.e., amino acids 19-174 of SEQ ID NO:9) are the extracellular domain of human TREM2, and the bold amino acids (i.e., amino acids 1-18 of SEQ ID NO:9) are the signal peptide of human TREM2).

A soluble form of TREM2 is derived from proteolytic cleavage of cell surface TREM2. As used herein "soluble TREM2" refers to these cleaved proteins, e.g., as found in or obtained from human plasma or cerebrospinal fluid, and also includes recombinantly produced versions of such proteins. One form of soluble TREM2 comprises, consists essentially of, or consists of amino acids 19-157 of SEQ ID NO:9.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment," "antigen-binding domain," or "antigen-binding region," refers to a portion of an intact antibody that binds to an antigen. An antigen-binding fragment can contain an antigen recognition site of an intact antibody (e.g., complementarity determining regions (CDRs) sufficient to bind antigen). Examples of antigen-binding fragments of antibodies include, but are not limited to Fab, Fab', F(ab')2, and Fv fragments, linear antibodies, and single chain antibodies. An antigen-binding fragment of an antibody can be derived from any animal species, such as rodents (e.g., mouse, rat, or hamster) and humans or can be artificially produced.

The terms "anti-TREM2 antibody," "TREM2 antibody," and "antibody that binds to TREM2" refer to an antibody that is capable of binding TREM2 with sufficient affinity such that the antibody is useful as a diagnostic and/or therapeutic agent in targeting TREM2. These terms indicate that the antibody or antigen-binding fragment thereof binds to TREM2 via its antigen-binding domain and that the binding entails some complementarity between the antigen-binding domain and TREM2. Accordingly, an antibody that binds to human TREM2 (amino acids 19-230 of SEQ ID NO:9) may also bind to TREM2 from other species (e.g., mouse TREM2) and/or TREM2 proteins produced from other human alleles, but the extent of binding to an unrelated, non-TREM2 protein is less than about 10% of the binding of the antibody to TREM2 as measured, e.g., by a radioimmunoassay (RIA).

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibodies or antigen-binding fragments thereof refers to such antibodies and antigen-binding fragments thereof made in any number of manners including but not limited to by hybridoma, phage selection, recombinant expression, and transgenic animals.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that CDRs of the light and heavy chains are primarily responsible for the interaction and specificity of the antibody with antigen. In certain aspects, the variable region is a human variable region. In certain aspects, the variable region comprises rodent or murine CDRs and human framework regions (FRs). In particular aspects, the variable region is a primate (e.g., non-human primate) variable region. In certain aspects, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR H1), amino acid positions 50 to 65 (CDR H2), and amino acid positions 95 to 102 (CDR H3). Using the Kabat numbering system, CDRs within an antibody light chain molecule are typically present at amino acid positions 24 to 34 (CDR L1), amino acid positions 50 to 56 (CDR L2), and amino acid positions 89 to 97 (CDR L3). In a specific aspect, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
| --- | --- | --- | --- |
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

As used herein, the terms "constant region" and "constant domain" are interchangeable and have their meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In certain aspects, an antibody or antigen-binding fragment comprises a constant region or portion thereof that is sufficient for antibody-dependent cell-mediated cytotoxicity (ADCC).

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$. Heavy chain amino acid sequences are well known in the art. In specific aspects, the heavy chain is a human heavy chain.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific aspects, the light chain is a human light chain.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the non-human CDR residues to refine and optimize the specificity, affinity, and/or capability of the antibody or antigen-binding fragment thereof. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In some aspects, a "humanized antibody" is a resurfaced antibody.

The term "human" antibody or antigen-binding fragment thereof means an antibody or antigen-binding fragment thereof having an amino acid sequence derived from a human immunoglobulin gene locus, where such antibody or antigen-binding fragment is made using any technique known in the art. This definition of a human antibody or antigen-binding fragment thereof includes intact or full-length antibodies and fragments thereof.

"Binding affinity" generally refers to the strength of the sum total of non-covalent interactions between a single binding site of a molecule (e.g., an antibody or antigen-binding fragment thereof) and its binding partner (e.g., an antigen). Unless indicated otherwise, as used herein, "binding affinity" refers to intrinsic binding affinity which reflects a 1:1 interaction between members of a binding pair (e.g., antibody or antigen-binding fragment thereof and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody or antigen-binding fragment thereof to an antigen, and $k_{off}$ refers to the dissociation of, e.g., an antibody or antigen-binding fragment thereof from an antigen. The $k_{on}$ and $k_{off}$ can be determined by techniques known to one of ordinary skill in the art, such as BIAcore® or KinExA.

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain aspects, the epitope to which an antibody or antigen-binding fragment thereof binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody/antigen-binding fragment thereof: antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies can be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

An TREM2 antibody that "binds to the same epitope" as a reference TREM2 antibody refers to an antibody that binds to the same TREM2 amino acid residues and TREM2 protein modifications (e.g., glycosylation) as the reference TREM2 antibody. The ability of a TREM2 antibody to bind to the same epitope as a reference TREM2 antibody is determined by a hydrogen/deuterium exchange assay (see Coales et al. Rapid Commun. Mass Spectrom. 2009; 23: 639-647).

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition can be determined by any method known in the art, for example, competition ELISA assays. An antibody may be said to competitively inhibit binding of the reference antibody to a given epitope by at least 90%, at least 80%, at least 70%, at least 60%, or at least 50%.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some aspects, an antibody, polynucleotide, vector, cell, or composition which is isolated is substantially pure. As used herein, "substantially pure" refers to material which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain aspects, the polypeptides can occur as single chains or associated chains.

"Percent identity" refers to the extent of identity between two sequences (e.g., amino acid sequences or nucleic acid sequences). Percent identity can be determined by aligning two sequences, introducing gaps to maximize identity between the sequences. Alignments can be generated using programs known in the art. For purposes herein, alignment of nucleotide sequences can be performed with the blastn program set at default parameters, and alignment of amino acid sequences can be performed with the blastp program set at default parameters (see National Center for Biotechnology Information (NCBI) on the worldwide web, ncbi.nlm.nih.gov).

As used herein, the term "host cell" can be any type of cell, e.g., a primary cell, a cell in culture, or a cell from a cell line. In specific aspects, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The terms "administer," "administering," "administration," and the like, as used herein, refer to methods that may be used to enable delivery of a drug, e.g., an anti-TREM2 antibody or antigen-binding fragment thereof to the desired site of biological action (e.g., intravenous administration). Administration techniques that can be employed with the agents and methods described herein are found in e.g., Goodman and Gilman, *The Pharmacological Basis of Therapeutics*, current edition, Pergamon; and Remington's, *Pharmaceutical Sciences*, current edition, Mack Publishing Co., Easton, Pa.

As used herein, the terms "subject" and "patient" are used interchangeably. The subject can be an animal. In some aspects, the subject is a mammal such as a non-human animal (e.g., cow, pig, horse, cat, dog, rat, mouse, monkey or other primate, etc.). In some aspects, the subject is a human.

The term "therapeutically effective amount" refers to an amount of a therapeutic, e.g., an anti-TREM2 antibody or antigen-binding fragment thereof, effective to treat a disease or disorder in a subject. In the case of neurodegenerative disorder, the therapeutically effective amount of the therapeutic can reduce neuroinflammation, decrease amyloid plaques, increase uptake of beta amyloid (e.g., by microglia), and/or improve symptoms in patients with a neurodegenerative disease or disorder. A "prophylactically effective amount" refers to an amount effective to achieve the desired prophylactic result.

Terms such as "treating," "treatment," "to treat," "alleviating," and "to alleviate" refer to therapeutic measures that cure, slow down, lessen symptoms of, and/or halt progression of a pathologic condition or disorder. Thus, those in need of treatment include those already diagnosed with or suspected of having the disorder. In certain aspects, a subject is successfully "treated" for a neurodegenerative disease or disorder according to the methods of the present invention if the patient shows one or more of the following: decreased neuroinflammation, reduced amyloid plaques, or improved cognitive ability.

Prophylactic or preventative measures refer to measures that prevent and/or slow the development of a targeted pathological condition or disorder, e.g., a neurodegenerative disease or disorder. Thus, those in need of prophylactic or preventative measures include those prone to have the pathological condition or disorder and those in whom the pathological condition or disorder is to be prevented.

As used in the present disclosure and claims, the singular forms "a," "an," and "the" include plural forms unless the context clearly dictates otherwise.

It is understood that wherever aspects are described herein with the language "comprising," otherwise analogous aspects described in terms of "consisting of" and/or "consisting essentially of" are also provided. In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited are not changed by the presence of more than that which is recited, but excludes prior art embodiments.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "about" and "approximately," when used to modify a numeric value or numeric range, indicate that deviations of 5% to 10% above and 5% to 10% below the value or range remain within the intended meaning of the recited value or range.

Any compositions or methods provided herein can be combined with one or more of any of the other compositions and methods provided herein.

II. Anti-TREM2 Antibody and Antigen-Binding Fragments Thereof

In a specific aspect, provided herein are antibodies (e.g., monoclonal antibodies) and antigen-binding fragments thereof which specifically bind to TREM2 (e.g., human TREM2). The amino acid sequences for human TREM2 are known in the art and are also provided herein as amino acids 19-230 of SEQ ID NO:9.

In certain aspects, an antibody or antigen-binding fragment thereof provided herein binds to human TREM2 and comprises the six CDRs of the CGX101 antibody as provided in Tables 1 and 2.

TABLE 1

| | VH CDR Amino Acid Sequences | | |
|---|---|---|---|
| Antibody | CDR H1 (SEQ ID NO) | CDR H2 (SEQ ID NO) | CDR H3 (SEQ ID NO) |
| CGX101 | IMGT: GYTFTDYN (SEQ ID NO: 1) | IMGT: IYPKNGGT (SEQ ID NO: 2) | IMGT: ARRTARAS WFAF (SEQ ID NO: 3) |
| | Kabat: DYNIH (SEQ ID NO: 10) | Kabat: YIYPKNGGTGYT QKFKS (SEQ ID NO: 11) | Kabat: RTARASWFAF (SEQ ID NO: 12) |

TABLE 2

| | VL CDR Amino Acid Sequences | | |
|---|---|---|---|
| Antibody | CDR L1 (SEQ ID NO) | CDR L2 (SEQ ID NO) | CDR L3 (SEQ ID NO) |
| CGX101 | IMGT: QSLLYSSNQKNY (SEQ ID NO: 4) | IMGT: WAS (SEQ ID NO: 5) | IMGT and Kabat: QQYYNYPFT (SEQ ID NO: 6) |
| | Kabat: KSSQSLLYSSNQK NYLA (SEQ ID NO: 13) | Kabat: WASTRES (SEQ ID NO: 14) | |

In certain aspects, an antibody or antigen-binding fragment thereof described herein binds to human TREM2 and comprises a VH listed in Table 3, e.g., in combination with a VL.

TABLE 3

| Variable Heavy Chain (VH) Amino Acid Sequences | |
|---|---|
| Description of VH | VH Amino Acid Sequence (SEQ ID NO) |
| hCGX101 | EVQLVQSGAEVKKPGESLKISCKGSGYTFTDYNIHWVRQM PGKGLEWMGYIYPKNGGTYTQKFKSQVTISVDNSISTAY LQWSSLKASDTAMYYCARRTARASWFAFWGQGTLVTVSS (SEQ ID NO: 7) |

In certain aspects, an antibody or antigen-binding fragment thereof described herein binds to human TREM2 and comprises a VH comprising the same amino acid sequence as the VH of the antibody produced by the CGX-c1 hybridoma cell line deposited at the American Type Culture Collection (ATCC®) at 10801 University Blvd. Manassas, Virginia, 20110 USA as deposit number PTA-125491 on Nov. 14, 2018, e.g., in combination with a VL.

In certain aspects, an antibody or antigen-binding fragment thereof described herein binds to human TREM2 and comprises a VL listed in Table 4, e.g., in combination with a VH.

TABLE 4

| Variable Light Chain (VL) Amino Acid Sequences | |
|---|---|
| Description of VL | VL Amino Acid Sequence (SEQ ID NO) |
| hCGX101 | DIVIVITQSPATLSVSPGERATLSCKSSQSLLYSSNQKN YLAWYQQKPGQAPRVLIYWASTRESGIPARFSGSGSGTE FTLTISSLQSEDFAVYYCQQYYNYPFTFGQGTKLEIK (SEQ ID NO: 8) |

In certain aspects, an antibody or antigen-binding fragment thereof described herein binds to human TREM2 and comprises a VL comprising the same amino acid sequence as the VL of the antibody produced by the CGX-c1 hybridoma deposited at the ATCC® as deposit number PTA-125491 on Nov. 14, 2018, e.g., in combination with a VH.

In certain aspects, an antibody or antigen-binding fragment thereof described herein binds to human TREM2 and comprises a VH listed in Table 3 and a VL of listed in Table 4.

In certain aspects, an antibody or antigen-binding fragment thereof described herein binds to human TREM2 and comprises a VH comprising the same amino acid sequence as the VH of the antibody produced by the CGX-c1 hybridoma deposited at the ATCC® as deposit number PTA-125491 on Nov. 14, 2018, and a VL comprising the same amino acid sequence as the VL of the antibody produced by the CGX-c1 hybridoma deposited at the ATCC® as deposit number PTA-125491 on Nov. 14, 2018.

In certain aspects, an antibody or antigen-binding fragment thereof described herein binds to human TREM2, comprises (i) a VH comprising a sequence at least 80% identical to the VH of the antibody produced by the CGX-c1 hybridoma deposited at the ATCC® as deposit number PTA-125491 on Nov. 14, 2018, and a VL comprising a sequence at least 80% identical to the VL of the antibody produced by the CGX-c1 hybridoma deposited at the ATCC® as deposit number PTA-125491 on Nov. 14, 2018, or (ii) a VH comprising a sequence at least 80% identical to a VH sequence in Table 3 and a VL comprising a sequence at least 80% identical to a VL sequence in Table 4. In certain aspects, an antibody or antigen-binding fragment thereof described herein binds to human TREM2, comprises (i) a VH comprising a sequence at least 85% identical to the VH of the antibody produced by the CGX-c1 hybridoma deposited at the ATCC® as deposit number PTA-125491 on Nov. 14, 2018, and a VL comprising a sequence at least 85% identical to the VL of the antibody produced by the CGX-c1 hybridoma deposited at the ATCC® as deposit number PTA-125491 on Nov. 14, 2018, or (ii) a VH comprising a sequence at least 85% identical to a VH sequence in Table 3 and a VL comprising a sequence at least 85% identical to a VL sequence in Table 4.

In certain aspects, an antibody or antigen-binding fragment thereof described herein binds to human TREM2, comprises (i) a VH comprising a sequence at least 90% identical to the VH of the antibody produced by the CGX-c1 hybridoma deposited at the ATCC® as deposit number PTA-125491 on Nov. 14, 2018, and a VL comprising a sequence at least 90% identical to the VL of the antibody produced by the CGX-c1 hybridoma deposited at the ATCC® as deposit number PTA-125491 on Nov. 14, 2018, or (ii) a VH comprising a sequence at least 90% identical to a VH sequence in Table 3 and a VL comprising a sequence at least 90% identical to a VL sequence in Table 4. In certain aspects, an antibody or antigen-binding fragment thereof described herein binds to human TREM2, comprises (i) a VH comprising a sequence at least 95% identical to the VH of the antibody produced by the CGX-c1 hybridoma deposited at the ATCC® as deposit number PTA-125491 on Nov. 14, 2018, and a VL comprising a sequence at least 95% identical to the VL of the antibody produced by the CGX-c1 hybridoma deposited at the ATCC® as deposit number PTA-125491 on Nov. 14, 2018, or (ii) a VH comprising a sequence at least 95% identical to a VH sequence in Table 3 and a VL comprising a sequence at least 95% identical to a VL sequence in Table 4.

In certain aspects, an antibody or antigen-binding fragment thereof described herein binds to human TREM2, comprises (i) a VH comprising a sequence at least 96% identical to the VH of the antibody produced by the CGX-c1 hybridoma deposited at the ATCC® as deposit number PTA-125491 on Nov. 14, 2018, and a VL comprising a sequence at least 96% identical to the VL of the antibody produced by the CGX-c1 hybridoma deposited at the ATCC® as deposit number PTA-125491 on Nov. 14, 2018, or (ii) a VH comprising a sequence at least 96% identical to a VH sequence in Table 3 and a VL comprising a sequence at least 96% identical to a VL sequence in Table 4. In certain aspects, an antibody or antigen-binding fragment thereof described herein binds to human TREM2, comprises (i) a VH comprising a sequence at least 97% identical to the VH of the antibody produced by the CGX-c1 hybridoma deposited at the ATCC® as deposit number PTA-125491 on Nov. 14, 2018, and a VL comprising a sequence at least 97% identical to the VL of the antibody produced by the CGX-c1 hybridoma deposited at the ATCC® as deposit number PTA-125491 on Nov. 14, 2018, or (ii) a VH comprising a sequence at least 97% identical to a VH sequence in Table 3 and a VL comprising a sequence at least 97% identical to a VL sequence in Table 4. In certain aspects, an antibody or antigen-binding fragment thereof described herein binds to human TREM2, comprises (i) a VH comprising a sequence at least 98% identical to the VH of the antibody produced by the CGX-c1 hybridoma deposited at the ATCC® as deposit number PTA-125491 on Nov. 14, 2018, and a VL comprising a sequence at least 98% identical to the VL of the antibody produced by the CGX-c1 hybridoma deposited at the ATCC® as deposit number PTA-125491 on Nov. 14, 2018, or (ii) a VH comprising a sequence at least 98% identical to a VH sequence in Table 3 and a VL comprising a sequence at least 98% identical to a VL sequence in Table 4. In certain aspects, an antibody or antigen-binding fragment thereof described herein binds to human TREM2, comprises (i) a VH comprising a sequence at least 99% identical to the VH of the antibody produced by the CGX-c1 hybridoma deposited at the ATCC® as deposit number PTA-125491 on Nov. 14, 2018, and a VL comprising a sequence at least 99% identical to the VL of the antibody produced by the CGX-c1 hybridoma deposited at the ATCC® as deposit number PTA-125491 on Nov. 14, 2018, or (ii) a VH comprising a sequence at least 99% identical to a VH sequence in Table 3 and a VL comprising a sequence at least 99% identical to a VL sequence in Table 4.

In certain aspects, an antibody or antigen-binding fragment thereof described herein binds to human TREM2, comprises (i) a VH comprising a sequence at least 80% identical to the VH of the antibody produced by the CGX-c1 hybridoma deposited at the ATCC® as deposit number PTA-125491 on Nov. 14, 2018, and a VL comprising a sequence at least 80% identical to the VL of the antibody produced by the CGX-c1 hybridoma deposited at the ATCC® as deposit number PTA-125491 on Nov. 14, 2018, or (ii) a VH comprising a sequence at least 80% identical to a VH sequence in Table 3 and a VL comprising a sequence at least 80% identical to a VL sequence in Table 4, wherein the antibody or antigen-binding fragment thereof inhibits neuroinflammation, decreases amyloid plaques, and/or increases uptake of beta amyloid (e.g., by microglia). In certain aspects, an antibody or antigen-binding fragment thereof described herein binds to human TREM2, comprises (i) a VH comprising a sequence at least 85% identical to the VH of the antibody produced by the CGX-c1 hybridoma deposited at the ATCC® as deposit number PTA-125491 on Nov. 14, 2018, and a VL comprising a sequence at least 85% identical to the VL of the antibody produced by the CGX-c1 hybridoma deposited at the ATCC® as deposit number PTA-125491 on Nov. 14, 2018, or (ii) a VH comprising a sequence at least 85% identical to a VH sequence in Table 3 and a VL comprising a sequence at least 85% identical to a VL sequence in Table 4, wherein the antibody or antigen-binding fragment thereof inhibits neuroinflammation, decreases amyloid plaques, and/or increases uptake of beta amyloid (e.g., by microglia).

In certain aspects, an antibody or antigen-binding fragment thereof described herein binds to human TREM2, comprises (i) a VH comprising a sequence at least 90% identical to the VH of the antibody produced by the CGX-c1 hybridoma deposited at the ATCC® as deposit number PTA-125491 on Nov. 14, 2018, and a VL comprising a sequence at least 90% identical to the VL of the antibody produced by the CGX-c1 hybridoma deposited at the ATCC® as deposit number PTA-125491 on Nov. 14, 2018, or (ii) a VH comprising a sequence at least 90% identical to a VH sequence in Table 3 and a VL comprising a sequence at least 90% identical to a VL sequence in Table 4, wherein the antibody or antigen-binding fragment thereof inhibits neuroinflammation, decreases amyloid plaques, and/or increases uptake of beta amyloid (e.g., by microglia). In certain aspects, an antibody or antigen-binding fragment thereof described herein binds to human TREM2, comprises (i) a VH comprising a sequence at least 95% identical to the VH of the antibody produced by the CGX-c1 hybridoma deposited at the ATCC® as deposit number PTA-125491 on Nov. 14, 2018, and a VL comprising a sequence at least 95% identical to the VL of the antibody produced by the CGX-c1 hybridoma deposited at the ATCC® as deposit number PTA-125491 on Nov. 14, 2018, or (ii) a VH comprising a sequence at least 95% identical to a VH sequence in Table 3 and a VL comprising a sequence at least 95% identical to a VL sequence in Table 4, wherein the antibody or antigen-binding fragment thereof inhibits neuroinflammation, decreases amyloid plaques, and/or increases uptake of beta amyloid (e.g., by microglia).

In certain aspects, an antibody or antigen-binding fragment thereof described herein binds to human TREM2, comprises (i) a VH comprising a sequence at least 96% identical to the VH of the antibody produced by the CGX-c1 hybridoma deposited at the ATCC® as deposit number PTA-125491 on Nov. 14, 2018, and a VL comprising a sequence at least 96% identical to the VL of the antibody produced by the CGX-c1 hybridoma deposited at the ATCC® as deposit number PTA-125491 on Nov. 14, 2018, or (ii) a VH comprising a sequence at least 96% identical to a VH sequence in Table 3 and a VL comprising a sequence at least 96% identical to a VL sequence in Table 4, wherein the antibody or antigen-binding fragment thereof inhibits neuroinflammation, decreases amyloid plaques, and/or increases uptake of beta amyloid (e.g., by microglia). In certain aspects, an antibody or antigen-binding fragment thereof described herein binds to human TREM2, comprises (i) a VH comprising a sequence at least 97% identical to the VH of the antibody produced by the CGX-c1 hybridoma deposited at the ATCC® as deposit number PTA-125491 on Nov. 14, 2018, and a VL comprising a sequence at least 97% identical to the VL of the antibody produced by the CGX-c1 hybridoma deposited at the ATCC® as deposit number PTA-125491 on Nov. 14, 2018, or (ii) a VH comprising a sequence at least 97% identical to a VH sequence in Table 3 and a VL comprising a sequence at least 97% identical to a VL sequence in Table 4, wherein the antibody or antigen-binding fragment thereof inhibits neuroinflammation, decreases amyloid plaques, and/or increases uptake of beta amyloid (e.g., by microglia). In certain aspects, an antibody or antigen-binding fragment thereof described herein binds to human TREM2, comprises (i) a VH comprising a sequence at least 98% identical to the VH of the antibody produced by the CGX-c1 hybridoma deposited at the ATCC® as deposit number PTA-125491 on Nov. 14, 2018, and a VL comprising a sequence at least 98% identical to the VL of the antibody produced by the CGX-c1 hybridoma deposited at the ATCC® as deposit number PTA-125491 on Nov. 14, 2018, or (ii) a VH comprising a sequence at least 98% identical to a VH sequence in Table 3 and a VL comprising a sequence at least 98% identical to a VL sequence in Table 4, wherein the antibody or antigen-binding fragment thereof inhibits neuroinflammation, decreases amyloid plaques, and/or increases uptake of beta amyloid (e.g., by microglia). In certain aspects, an antibody or antigen-binding fragment thereof described herein binds to human TREM2, comprises (i) a VH comprising a sequence at least 99% identical to the VH of the antibody produced by the CGX-c1 hybridoma deposited at the ATCC® as deposit number PTA-125491 on Nov. 14, 2018, and a VL comprising a sequence at least 99% identical to the VL of the antibody produced by the CGX-c1 hybridoma deposited at the ATCC® as deposit number PTA-125491 on Nov. 14, 2018, or (ii) a VH comprising a sequence at least 99% identical to a VH sequence in Table 3 and a VL comprising a sequence at least 99% identical to a VL sequence in Table 4, wherein the antibody or antigen-binding fragment thereof inhibits neuroinflammation, decreases amyloid plaques, and/or increases uptake of beta amyloid (e.g., by microglia).

In certain aspects, an antibody or antigen-binding fragment thereof described herein may be described by its VL domain alone or its VH domain alone. See, for example, Rader C et al., (1998) PNAS 95: 8910-8915, which is incorporated herein by reference in its entirety, describing the humanization of the mouse anti-αvβ3 antibody by identifying a complementing light chain or heavy chain, respectively, from a human light chain or heavy chain library, resulting in humanized antibody variants having affinities as high or higher than the affinity of the original antibody. See also Clackson T et al., (1991) Nature 352: 624-628, which is incorporated herein by reference in its entirety, describing methods of producing antibodies that bind a specific antigen by using a specific VL domain (or VH domain) and screening a library for the complementary variable domains. The screen produced 14 new partners for a specific VH domain and 13 new partners for a specific VL domain, which were strong binders, as determined by ELISA. See also Kim S J & Hong H J, (2007) J Microbiol 45: 572-577, which is incorporated herein by reference in its entirety, describing methods of producing antibodies that bind a specific antigen by using a specific VH domain and screening a library (e.g., human VL library) for complementary VL domains; the selected VL domains in turn could be used to guide selection of additional complementary (e.g., human) VH domains.

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are antibodies and antigen-binding fragments thereof that specifically bind to TREM2 (e.g., human TREM2) and comprise the Chothia VH and VL CDRs of an antibody. In certain aspects, antibodies or antigen-binding fragments thereof that specifically bind to TREM2 (e.g., human TREM2) comprise one or more CDRs, in which the Chothia and Kabat CDRs have the same amino acid sequence. In certain aspects, provided herein are antibodies and antigen-binding fragments thereof that specifically bind to TREM2 (e.g., human TREM2) and comprise combinations of Kabat CDRs and Chothia CDRs.

In certain aspects, the CDRs of an antibody or antigen-binding fragment thereof can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, CDR H1 is at positions 26 to 35, CDR H2 is at positions 51 to 57, CDR H3 is at positions 93 to 102, CDR L1 is at positions 27 to 32, CDR L2 is at positions 50 to 52, and CDR L3 is at positions 89 to 97. In a particular aspect, provided herein are antibodies and antigen-binding fragments thereof that specifically bind to TREM2 (e.g., human TREM2) and comprise the IMGT VH and VL CDRs of an antibody listed in Tables 3 and 4, for example, as described in Lefranc M-P (1999) supra and Lefranc M-P et al., (1999) supra.

In certain aspects, the CDRs of an antibody or antigen-binding fragment thereof can be determined according to MacCallum R M et al., (1996) J Mol Biol 262: 732-745. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In a particular aspect, provided herein are antibodies or antigen-binding fragments thereof that specifically bind to TREM2 (e.g., human TREM2) are determined by the method in MacCallum R M et al.

In certain aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In a particular aspect, provided herein are antibodies or antigen-binding fragments thereof that specifically bind to TREM2 (e.g., human TREM2) are determined by the AbM numbering scheme.

In certain aspects, an antibody or antigen-binding fragment thereof described herein binds to human TREM2 and comprises a heavy chain comprising the same amino acid sequence as the heavy chain of the antibody produced by the CGX-c1 hybridoma deposited at the ATCC® as deposit number PTA-125491 on Nov. 14, 2018, e.g., in combination with a light chain.

In certain aspects, an antibody or antigen-binding fragment thereof described herein binds to human TREM2 and comprises a light chain comprising the same amino acid sequence as the light chain of the antibody produced by the CGX-c1 hybridoma deposited at the ATCC® as deposit number PTA-125491 on Nov. 14, 2018, e.g., in combination with a heavy chain.

In certain aspects, an antibody or antigen-binding fragment thereof described herein binds to human TREM2 and comprises a heavy chain comprising the same amino acid sequence as the heavy chain of the antibody produced by the CGX-c1 hybridoma deposited at the ATCC® as deposit number PTA-125491 on Nov. 14, 2018, and a light chain comprising the same amino acid sequence as the light chain of the antibody produced by the CGX-c1 hybridoma deposited at the ATCC® as deposit number PTA-125491 on Nov. 14, 2018.

In specific aspects, provided herein are antibodies that comprise a heavy chain and a light chain.

In a specific aspect, the heavy chain of an antibody described herein is a gamma heavy chain (e.g., a human gamma heavy chain, e.g., human $IgG_1$ or human $IgG_4$ heavy chain). In a particular aspect, an antibody which immunospecifically binds to TREM2 (e.g., human TREM2) provided herein comprises a heavy chain wherein the amino acid sequence of the VH domain comprises the VH sequence of the antibody produced by the CGX-c1 hybridoma deposited at the ATCC® as deposit number PTA-125491 on Nov. 14, 2018 or a VH sequence in Table 3, and wherein the constant region of the heavy chain comprises the amino acid sequence of a human gamma heavy chain (e.g., human $IgG_1$ or human $IgG_4$ heavy chain) constant region.

In a specific aspect, the light chain of an antibody described herein is a kappa light chain (e.g., a human kappa light chain). In a particular aspect, an antibody which immunospecifically binds to TREM2 (e.g., human TREM2) provided herein comprises a light chain wherein the amino acid sequence of the VL domain comprises the VL sequence of the antibody produced by the CGX-c1 hybridoma deposited at the ATCC® as deposit number PTA-125491 on Nov. 14, 2018, or a VL sequence in Table 4, and wherein the constant region of the light chain comprises the amino acid sequence of a human kappa light chain constant region.

In a particular aspect, an antibody which immunospecifically binds to TREM2 (e.g., human TREM2) provided herein comprises (i) a heavy chain wherein the amino acid sequence of the VH domain comprises the VH sequence of the antibody produced by the CGX-c1 hybridoma deposited at the ATCC® as deposit number PTA-125491 on Nov. 14, 2018, or a VH sequence in Table 3, and wherein the constant region of the heavy chain comprises the amino acid sequence of a human gamma heavy chain (e.g., human $IgG_1$ or human $IgG_4$ heavy chain) constant region and (ii) comprises a light chain wherein the amino acid sequence of the VL domain comprises the VL sequence of the antibody produced by CGX-c1 hybridoma deposited at the ATCC® as deposit number PTA-125491 on Nov. 14, 2018, or a VL sequence in Table 4, and wherein the constant region of the light chain comprises the amino acid sequence of a human kappa light chain constant region.

In another particular aspect, an antibody or antigen-binding fragment thereof described herein, which immunospecifically binds to TREM2 (e.g., human TREM2), comprises a heavy chain and a light chain, wherein (i) the heavy chain comprises a VH domain comprising the CDR H1, CDR H2, and CDR H3 amino acid sequences of the CGX101 antibody listed in Table 1; (ii) the light chain comprises a VL domain comprising the CDR L1, CDR L2, and CDR L3 amino acid sequences of the CGX101 antibody listed in Table 2; (iii) the heavy chain further comprises a constant heavy chain domain comprising the amino acid sequence of the constant domain of a human $IgG_1$ or human $IgG_4$ heavy chain; and (iv) the light chain further comprises a constant light chain domain comprising the amino acid sequence of the constant domain of a human kappa light chain.

In another aspect, provided herein are antibodies or antigen-binding fragments thereof that bind the same epitope of TREM2 (e.g., an epitope of human TREM2) as CGX101.

Competition binding assays can be used to determine whether two antibodies bind to overlapping epitopes. Competitive binding can be determined in an assay in which the immunoglobulin under test inhibits specific binding of a reference antibody to a common antigen, such as TREM2. Numerous types of competitive binding assays are known, for example: solid phase direct or indirect radioimmunoassay (MA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label MA using I-125 label (see Morel G A et al., (1988) Mol Immunol 25(1): 7-15); solid phase direct biotin-avidin EIA (Cheung R C et al., (1990) Virology 176: 546-52); and direct labeled RIA. (Moldenhauer G et al., (1990) Scand J Immunol 32: 77-82). Typically, such an assay involves the use of purified antigen (e.g., TREM2 such as human TREM2) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389.

In one aspect, a competition assay is performed using surface plasmon resonance (BIAcore®), e.g., by an 'in tandem approach' such as that described by Abdiche Y N et al., (2009) Analytical Biochem 386: 172-180, whereby TREM2 antigen is immobilized on the chip surface, for example, a CM5 sensor chip and the anti-TREM2 antibodies are then run over the chip. To determine if an antibody or antigen-binding fragment thereof competes with an anti-TREM2 antibody described herein, the anti-TREM2 antibody is first run over the chip surface to achieve saturation and then the potential, competing antibody is added. Binding of the competing antibody or antigen-binding fragment thereof can then be determined and quantified relative to a non-competing control.

In one aspect, provided herein are antibodies that competitively inhibit (e.g., in a dose dependent manner) CGX101 from binding to TREM2 (e.g., human TREM2), as determined using assays known to one of skill in the art or described herein (e.g., ELISA competitive assays, or suspension array or surface plasmon resonance assay).

In specific aspects, provided herein is an antibody or antigen-binding fragment which competitively inhibits (e.g., in a dose dependent manner) binding to TREM2 (e.g., human TREM2), of an antibody comprising the VH sequence of the antibody produced by the CGX-c1 hybridoma deposited at the ATCC® as deposit number PTA-125491 on Nov. 14, 2018, and the VL sequence of the antibody produced by the CGX-c1 hybridoma deposited at the ATCC® as deposit number PTA-125491 on Nov. 14, 2018, or of an antibody comprising a VH sequence in Table 3 and a VL sequence in Table 4.

In specific aspects, provided herein is an anti-TREM2 antibody or antigen-binding fragment thereof that does not trigger inflammation by peripheral blood mononuclear cells (PBMCs). In specific aspects, provided herein is an anti-TREM2 antibody or antigen-binding fragment thereof that does not increase tumor necrosis factor (TNF)-alpha expression in non-stimulated PBMCs. For example, in specific aspects, exposure (e.g., for about 15 hours to about 20 hours, or for about 18 hours) of non-stimulated PBMCs to an anti-TREM2 antibody or antigen-binding fragment provided herein (e.g., at a concentration of 1 μg/ml, 5 μg/ml, or 10 μg/ml) produces TNF-alpha levels of no more than 25 pg/ml or no more than 15 pg/ml (e.g., under circumstances were exposure of the non-stimulated PBMCs to 100 ng/ml of LPS produces TNF-alpha levels of at least 500 pg/ml, at least 600 pg/ml, or at least 700 pg/ml). Non-stimulated PBMCs can express very low levels of TREM2.

In specific aspects, provided herein is an anti-TREM2 antibody or antigen-binding fragment thereof that enhances acute microglial activation. In specific aspects, provided herein is an anti-TREM2 antibody or antigen-binding fragment thereof that increases TNF-alpha expression in microglia exposed to amyloid beta. For example, in specific aspects, exposure of microglia to amyloid beta and an anti-TREM2 antibody or antigen-binding fragment provided herein (e.g., at a concentration of 2 μg/ml, 15 μg/ml, or 30 μg/ml) produces TNF-alpha levels that are at least 1.5 times or at least 1.75 times the TNF-alpha levels produced by exposure to amyloid beta in the absence of the anti-TREM2 antibody or antigen-binding fragment thereof.

In specific aspects, provided herein is an anti-TREM2 antibody or antigen-binding fragment thereof that is capable of inhibiting neuroinflammation. For instance, in specific aspects, the antibody or antigen-binding fragment thereof is capable of inhibiting increased TNF-alpha, increased interleukin (IL)-6, and/or interferon (INF)-gamma expression (e.g., mRNA levels) induced by intracerebral injection of soluble TREM2.

In specific aspects, provided herein is an anti-TREM2 antibody or antigen-binding fragment thereof that is capable of decreasing amyloid plaques, e.g., in the brain.

In certain aspects, an anti-TREM2 antibody or antigen-binding fragment thereof described herein can immunospecifically binds to soluble TREM2. In certain aspects, an anti-TREM2 antibody or antigen-binding fragment thereof can reduce soluble TREM2, e.g., in the CSF, serum, or brain of a subject. For instance, a subject may have a particular level of soluble TREM2 in their CSF, serum, or brain, and that amount can be reduced as a result of administration of an anti-TREM2 antibody or antigen-binding fragment thereof described herein to the subject.

In certain aspects, an anti-TREM2 antibody or antigen-binding fragment thereof provided herein binds to at least one amino acid in amino acids 34-40 of SEQ ID NO:9 and/or at least one amino acid in amino acids 134-150 of SEQ ID NO:9. In certain aspects, the binding of an anti-TREM2 antibody or antigen-binding fragment thereof provided herein to TREM2 is disrupted by the presence of a peptide comprising amino acids 34-40 of SEQ ID NO:9 (including, e.g., a peptide consisting of amino acids 34-40 of SEQ ID NO:9 and an acetyl cap at N terminal). In certain aspects, the binding of an anti-TREM2 antibody or antigen-binding fragment thereof provided herein to TREM2 is disrupted by the presence of a peptide comprising amino acids 134-150 of SEQ ID NO:9 (including, e.g., a peptide consisting of amino acids 134-150 of SEQ ID NO:9 and an acetyl cap at N terminal). In certain aspects, the binding of an anti-TREM2 antibody or antigen-binding fragment thereof provided herein to TREM2 is disrupted by the presence of a peptide comprising amino acids 34-40 of SEQ ID NO:9 (including, e.g., a peptide consisting of amino acids 34-40 of SEQ ID NO:9 and an acetyl cap at N terminal) or by the presence of a peptide comprising amino acids 134-150 of SEQ ID NO:9 (including, e.g., a peptide consisting of amino acids 134-150 of SEQ ID NO:9 and an acetyl cap at N terminal).

In certain aspects, an antibody or antigen-binding fragment thereof described herein is an isolated antibody or antigen-binding fragment thereof. In certain aspects, an antibody or antigen-binding fragment thereof described herein is a monoclonal antibody or antigen-binding fragment thereof. In certain aspects, an antibody or antigen-binding fragment thereof described herein is not a polyclonal antibody or antigen-binding fragment thereof.

In a specific aspect, an antigen-binding fragment as described herein, which immunospecifically binds to TREM2 (e.g., human TREM2), is selected from the group consisting of a Fab, Fab', F(ab')$_2$, and scFv, wherein the Fab, Fab', F(ab')$_2$, or scFv comprises a heavy chain variable region sequence and a light chain variable region sequence of an anti-TREM2 antibody or antigen-binding fragment thereof as described herein. A Fab, Fab', F(ab')$_2$, or scFv can be produced by any technique known to those of skill in the art. In certain aspects, the Fab, Fab', F(ab')$_2$, or scFv further comprises a moiety that extends the half-life of the antibody in vivo. The moiety is also termed a "half-life extending moiety." Any moiety known to those of skill in the art for extending the half-life of a Fab, Fab', F(ab')$_2$, or scFv in vivo can be used. For example, the half-life extending moiety can include a Fc region, a polymer, an albumin, or an albumin binding protein or compound. The polymer can include a natural or synthetic, optionally substituted straight or branched chain polyalkylene, polyalkenylene, polyoxylalkylene, polysaccharide, polyethylene glycol, polypropylene glycol, polyvinyl alcohol, methoxypolyethylene glycol, lactose, amylose, dextran, glycogen, or derivative thereof. Substituents can include one or more hydroxy, methyl, or methoxy groups. In certain aspects, the Fab, Fab', F(ab')$_2$, or scFv can be modified by the addition of one or more C-terminal amino acids for attachment of the half-life extending moiety. In certain aspects the half-life extending moiety is polyethylene glycol or human serum albumin. In certain aspects, the Fab, Fab', F(ab')$_2$, or scFv is fused to an Fc region.

In certain aspects, an anti-TREM2 antibody or antigen-binding fragment thereof described herein is a bispecific antibody or antigen-binding fragment thereof.

An anti-TREM2 antibody or antigen-binding fragment thereof can be fused or conjugated (e.g., covalently or noncovalently linked) to a detectable label or substance. Examples of detectable labels or substances include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labeled antibodies or antigen-binding fragments thereof can be used to detect TREM2 (e.g., human TREM2) protein.

III. Antibody Production

Antibodies and antigen-binding fragments thereof that immunospecifically bind to TREM2 (e.g., human TREM2) can be produced by any method known in the art for the synthesis of antibodies and antigen-binding fragments thereof, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a certain aspect, provided herein is a method of making an antibody or antigen-binding fragment which immunospecifically binds to TREM2 (e.g., human TREM2) comprising culturing a cell or host cell described herein. In a certain aspect, provided herein is a method of making an antibody or antigen-binding fragment thereof which immunospecifically binds to TREM2 (e.g., human TREM2) comprising expressing (e.g., recombinantly expressing) the antibody or antigen-binding fragment thereof using a cell or host cell described herein (e.g., a cell or a host cell comprising polynucleotides encoding an antibody or antigen-binding fragment thereof described herein). In a particular aspect, the cell is an isolated cell. In a particular aspect, the exogenous polynucleotides have been introduced into the cell. In a particular aspect, the method further comprises the step of purifying the antibody or antigen-binding fragment obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies or antigen-binding fragments thereof can be prepared using a wide variety of techniques known in the art including the use of hybridoma, recombinant, and phage display technologies, yeast-based presentation technologies, or a combination thereof. For example, monoclonal antibodies or antigen-binding fragments thereof can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), or as described in Kohler G & Milstein C (1975) Nature 256: 495. Examples of yeast-based presentation methods that can be employed to select and generate the antibodies described herein include those disclosed in, for example, WO2009/036379A2; WO2010/105256; and WO2012/009568, each of which is herein incorporated by reference in its entirety.

In specific aspects, a monoclonal antibody or antigen-binding fragment thereof may be produced using the hybridoma method first described by Kohler et al., Nature, 256:495 (1975), as mentioned above. In the hybridoma method, a mouse or another appropriate host animal is immunized as above described to elicit lymphocytes that produce or are capable of producing antibodies that will specifically bind to the protein used for immunization, for example, variant mixtures of TREM2. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986).

In specific aspects, a monoclonal antibody or antigen-binding fragment thereof is an antibody or antigen-binding fragment produced by a clonal cell (e.g., hybridoma or host cell producing a recombinant antibody or antigen-binding fragment), wherein the antibody or antigen-binding fragment immunospecifically binds to TREM2 (e.g., human TREM2) as determined, e.g., by ELISA or other antigen-binding assays known in the art or in the Examples provided herein. In particular aspects, a monoclonal antibody or antigen-binding fragment thereof can be a rodent or murine antibody or antigen-binding fragment thereof. In particular aspects, a monoclonal antibody or antigen-binding fragment thereof can be a chimeric or a humanized antibody or antigen-binding fragment thereof. In certain aspects, a monoclonal antibody or antigen-binding fragment thereof can be a Fab fragment or an F(ab')$_2$ fragment. Monoclonal antibodies or antigen-binding fragments thereof described herein can, for example, be made by the hybridoma method as described in Kohler G & Milstein C (1975) Nature 256: 495 or can, e.g., be isolated from phage libraries using the techniques as described herein, for example. Other methods for the preparation of clonal cell lines and of monoclonal antibodies and antigen-binding fragments thereof expressed thereby are well known in the art (see, for example, Chapter 11 in: Short Protocols in Molecular Biology, (2002) 5th Ed., Ausubel F M et al., supra).

Antigen-binding fragments of antibodies described herein can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of a tetrameric antibody molecule and contains the complete light chain paired with the VH and CH1 domains of the heavy chain. An F(ab')$_2$ fragment contains the two antigen-binding arms of a tetrameric antibody molecule linked by disulfide bonds in the hinge region.

Further, the antibodies or antigen-binding fragments thereof described herein can also be generated using various phage display and/or yeast-based presentation methods known in the art. In phage display methods, proteins are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antibody or antigen-binding fragment thereof that binds to a particular antigen can be selected or identified with antigen, e.g., using labeled antigen or antigen bound or captured to a solid surface or bead. Examples of phage display methods that can be used to make the antibodies or fragments described herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/11236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, and 5,969,108.

An antibody or antigen-binding fragment thereof can be selected from any class of immunoglobulins, including IgM, IgG, IgD, IgA, and IgE, and any isotype, including IgG$_1$, IgG$_2$, IgG$_3$ and IgG$_4$.

IIIa. Polynucleotides

In certain aspects, provided herein are polynucleotides comprising a nucleotide sequence encoding an antibody or antigen-binding fragment thereof described herein or a domain thereof (e.g., a variable light chain region and/or variable heavy chain region) that immunospecifically binds to a TREM2 (e.g., human TREM2) antigen, and vectors, e.g., vectors comprising such polynucleotides for recombinant expression in host cells (e.g., E. coli and mammalian cells).

In particular aspects, provided herein are polynucleotides comprising nucleotide sequences encoding antibodies or antigen-binding fragments thereof, which immunospecifically bind to a TREM2 polypeptide (e.g., human TREM2) and comprise an amino acid sequence as described herein, as well as antibodies or antigen-binding fragments that compete with such antibodies or antigen-binding fragments for binding to a TREM2 polypeptide (e.g., in a dose-dependent manner), or which bind to the same epitope as that of such antibodies or antigen-binding fragments.

Also provided herein is a polynucleotide comprising a nucleotide sequence encoding a VH polypeptide comprising the amino acid sequence of SEQ ID NO:7 or comprising the same amino acid sequence as the VH of the antibody produced by the CGX-c1 hybridoma deposited at the ATCC® as deposit number PTA-125491 on Nov. 14, 2018. In some aspects, an antibody or antigen-binding fragment thereof comprising the polypeptide immunospecifically binds to TREM2.

Also provided herein is a polynucleotide comprising a nucleotide sequence encoding a VL polypeptide comprising the amino acid sequence of SEQ ID NO:8 or comprising the same amino acid sequence as the VL of the antibody produced by the CGX-c1 hybridoma deposited at the ATCC® as deposit number PTA-125491 on Nov. 14, 2018. In some aspects, an antibody or antigen-binding fragment thereof comprising the polypeptide immunospecifically binds to TREM2.

Also provided herein is a polynucleotide comprising a nucleotide sequence encoding a polypeptide comprising a sequence selected from the group consisting of SEQ ID NOs:1-3 or comprising the amino acids of all of SEQ ID NOs:1-3. In some aspects, an antibody or antigen-binding fragment thereof comprising the polypeptide immunospecifically binds to TREM2. Also provided herein is a polynucleotide comprising a nucleotide sequence encoding a polypeptide comprising a sequence selected from the group consisting of SEQ ID NOs:4-6 or comprising all of SEQ ID NOs:4-6. In some aspects, an antibody or antigen-binding fragment thereof comprising the polypeptide immunospecifically binds to TREM2.

Also provided herein is a polynucleotide comprising a nucleotide sequence encoding a heavy chain polypeptide comprising the same amino acid sequence as the heavy chain of the antibody produced by the CGX-c1 hybridoma deposited at the ATCC® as deposit number PTA-125491 on Nov. 14, 2018. In some aspects, an antibody or antigen-binding fragment thereof comprising the polypeptide immunospecifically binds to TREM2.

Also provided herein is a polynucleotide comprising a nucleotide sequence encoding a light chain polypeptide comprising the same amino acid sequence as the light chain of the antibody produced by the CGX-c1 hybridoma deposited at the ATCC® as deposit number PTA-125491 on Nov. 14, 2018. In some aspects, an antibody or antigen-binding fragment thereof comprising the polypeptide immunospecifically binds to TREM2.

A nucleic acid encoding a heavy chain variable domain or heavy chain and a nucleic acid encoding a light chain variable domain or light chain may be in the same polynucleotide or in different polynucleotides. A nucleic acid encoding a heavy chain variable domain or heavy chain and a nucleic acid encoding a light chain variable domain or light chain may be in the same vector or in different vectors.

Also provided herein is a composition comprising (i) a polynucleotide comprising nucleic acid comprising the heavy chain variable domain-encoding sequence in the CGX-c1 hybridoma deposited at the ATCC® as deposit number PTA-125491 on Nov. 14, 2018, and (ii) a polynucleotide comprising a nucleic acid comprising the light chain variable domain-encoding sequence in the CGX-c1 hybridoma deposited at the ATCC® as deposit number PTA-125491 on Nov. 14, 2018. The nucleic acid encoding the heavy chain variable domain and the nucleic acid encoding the light chain variable domain may be in the same polynucleotide or in different polynucleotides. The nucleic acid encoding the heavy chain variable domain and the nucleic acid encoding the light chain variable domain may be in the same vector or in different vectors.

Also provided herein are polynucleotides comprising a nucleotide sequence that encodes SEQ ID NOs:1-3 and/or 4-6; SEQ ID NO:7 and/or 8; or the heavy chain variable domain in the CGX-c1 hybridoma deposited at the ATCC® as deposit number PTA-125491 on Nov. 14, 2018, and/or the light chain variable domain in the h CGX-c1 hybridoma deposited at the ATCC® as deposit number PTA-125491 on Nov. 14, 2018.

Also provided herein are polynucleotides that are at least about 80%, 85%, or 90% identical to a nucleotide sequence that encodes SEQ ID NOs:1-3 and/or 4-6; SEQ ID NO:7 and/or 8; or the heavy chain variable domain in the CGX-c1 hybridoma deposited at the ATCC® as deposit number PTA-125491 on Nov. 14, 2018, and/or the light chain variable domain in the CGX-c1 hybridoma deposited at the ATCC® as deposit number PTA-125491 on Nov. 14, 2018.

Also provided herein are polynucleotides comprising a nucleotide sequence that is at least about 95% identical to a nucleotide sequence that encodes SEQ ID NOs:1-3 and/or 4-6; SEQ ID NO:7 and/or 8; or the heavy chain variable domain in the CGX-c1 hybridoma deposited at the ATCC® as deposit number PTA-125491 on Nov. 14, 2018, and/or the light chain variable domain in the CGX-c1 hybridoma deposited at the ATCC® as deposit number PTA-125491 on Nov. 14, 2018. Also provided herein are polynucleotides comprising a nucleotide sequence that is at least about 96% identical to a nucleotide sequence that encodes SEQ ID NOs:1-3 and/or 4-6; SEQ ID NO:7 and/or 8; or the heavy chain variable domain in the CGX-c1 hybridoma deposited at the ATCC® as deposit number PTA-125491 on Nov. 14, 2018, and/or the light chain variable domain in the CGX-c1 hybridoma deposited at the ATCC® as deposit number PTA-125491 on Nov. 14, 2018. Also provided herein are polynucleotides comprising a nucleotide sequence that is at least about 97% identical to a nucleotide sequence that encodes SEQ ID NOs:1-3 and/or 4-6; SEQ ID NO:7 and/or 8; or the heavy chain variable domain in the CGX-c1 hybridoma deposited at the ATCC® as deposit number PTA-125491 on Nov. 14, 2018, and/or the light chain variable domain in the CGX-c1 hybridoma deposited at the ATCC® as deposit number PTA-125491 on Nov. 14, 2018. Also provided herein are polynucleotides comprising a nucleotide sequence that is at least about 98% identical to a nucleotide sequence that encodes SEQ ID NOs:1-3 and/or 4-6; SEQ ID NO:7 and/or 8; or the heavy chain variable domain in CGX-c1 hybridoma deposited at the ATCC® as deposit number PTA-125491 on Nov. 14, 2018, and/or the light chain variable domain in the CGX-c1 hybridoma deposited at the ATCC® as deposit number PTA-125491 on Nov. 14, 2018. Also provided herein are polynucleotides comprising a nucleotide sequence that is at least about 99% identical to a nucleotide sequence that encodes SEQ ID NOs:1-3 and/or 4-6; SEQ ID NO:7 and/or 8; or the heavy chain variable domain in the CGX-c1 hybridoma deposited at the ATCC® as deposit number PTA-125491 on Nov. 14, 2018, and/or the light chain variable domain in the CGX-c1 hybridoma deposited at the ATCC® as deposit number PTA-125491 on Nov. 14, 2018.

In a particular aspect, a polynucleotide or combination of polynucleotides provided herein comprises a nucleotide sequence or combination of nucleotide sequences encoding an antibody or antigen-binding fragment thereof that immunospecifically binds to TREM2 (e.g., human TREM2), wherein the antibody or antigen-binding fragment thereof comprises a heavy chain, wherein the heavy chain comprises a heavy chain variable domain comprising the amino acid sequence of SEQ ID NO:7 or comprises the same amino acid sequence as the VH of the antibody produced by the CGX-c1 hybridoma deposited at the ATCC® as deposit number PTA-125491 on Nov. 14, 2018, and a constant region comprising the amino acid sequence of a human gamma (γ) heavy chain constant region (e.g., IgG4).

In a particular aspect, a polynucleotide or combination of polynucleotides provided herein comprises a nucleotide sequence or combination of nucleotide sequences encoding an antibody or antigen-binding fragment thereof that immunospecifically binds to TREM2 (e.g., human TREM2), wherein the antibody or antigen-binding fragment thereof comprises a light chain, wherein the light chain comprises a light chain variable domain comprising the amino acid sequence of SEQ ID NO:8 or comprises the same amino acid sequence as the VL of the antibody produced by the CGX-c1 hybridoma deposited at the ATCC® as deposit number PTA-125491 on Nov. 14, 2018, and a constant region comprising the amino acid sequence of a human kappa light chain constant region.

Also provided herein are polynucleotides encoding an anti-TREM2 antibody or antigen-binding fragment thereof described herein or a domain thereof that are optimized, e.g., by codon/RNA optimization, replacement with heterologous signal sequences, and elimination of mRNA instability elements. Methods to generate optimized nucleic acids encoding an anti-TREM2 antibody or antigen-binding fragment thereof or a domain thereof (e.g., heavy chain, light chain, VH domain, or VL domain) for recombinant expression by introducing codon changes (e.g., a codon change that encodes the same amino acid due to the degeneracy of the genetic code) and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly.

A polynucleotide encoding an antibody or antigen-binding fragment thereof described herein or a domain thereof can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody or antigen-binding fragment thereof. Such PCR amplification methods can be used to obtain nucleic acids comprising the sequence encoding the variable light chain region and/or the variable heavy chain region of an antibody or antigen-binding fragment thereof. The amplified nucleic acids can be cloned into vectors for expression in host cells and for further cloning, for example, to generate chimeric and humanized antibodies or antigen-binding fragments thereof.

Polynucleotides provided herein can be, e.g., in the form of RNA or in the form of DNA. DNA includes cDNA, genomic DNA, and synthetic DNA, and DNA can be double-stranded or single-stranded. If single stranded, DNA can be the coding strand or non-coding (anti-sense) strand. In certain aspects, the polynucleotide is a cDNA or a DNA lacking one more endogenous introns. In certain aspects, a polynucleotide is a non-naturally occurring polynucleotide. In certain aspects, a polynucleotide is recombinantly produced. In certain aspects, the polynucleotides are isolated. In certain aspects, the polynucleotides are substantially pure. In certain aspects, a polynucleotide is purified from natural components.

IIIb. Cells and Vectors

In certain aspects, provided herein are vectors (e.g., expression vectors) comprising polynucleotides comprising nucleotide sequences encoding anti-TREM2 antibodies and antigen-binding fragments thereof or a domain thereof for recombinant expression in host cells, preferably in mammalian cells. Also provided herein are cells, e.g., host cells, comprising such vectors for recombinantly expressing anti-TREM2 antibodies or antigen-binding fragments thereof described herein. In a particular aspect, provided herein are methods for producing an antibody or antigen-binding fragments thereof described herein, comprising expressing such antibody or antigen-binding fragment thereof in a host cell.

In certain aspects, recombinant expression of an antibody or antigen-binding fragment thereof or domain thereof described herein (e.g., a heavy or light chain described herein) that specifically binds to TREM2 (e.g., human TREM2) involves construction of an expression vector containing a polynucleotide that encodes the antibody or antigen-binding fragment thereof or domain thereof. Once a polynucleotide encoding an antibody or antigen-binding fragment thereof or domain thereof (e.g., heavy or light chain variable domain) described herein has been obtained, the vector for the production of the antibody or antigen-binding fragment thereof can be produced by recombinant DNA technology using techniques well known in the art. Thus, methods for preparing a protein by expressing a polynucleotide containing an antibody or antigen-binding fragment thereof or domain thereof (e.g., light chain or heavy chain) encoding nucleotide sequence are described herein. Methods which are well known to those skilled in the art can be used to construct expression vectors containing antibody or antigen-binding fragment thereof or domain thereof (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody or antigen-binding fragment thereof described herein, a heavy or light chain, a heavy or light chain variable domain, or a heavy or light chain CDR, operably linked to a promoter. Such vectors can, for example, include the nucleotide sequence encoding the constant region of the antibody or antigen-binding fragment thereof (see, e.g., International Publication Nos. WO 86/05807 and WO 89/01036; and U.S. Pat. No. 5,122,464), and variable domains of the antibody or antigen-binding fragment thereof can be cloned into such a vector for expression of the entire heavy, the entire light chain, or both the entire heavy and light chains.

An expression vector can be transferred to a cell (e.g., host cell) by conventional techniques, and the resulting cells can then be cultured by conventional techniques to produce an antibody or antigen-binding fragment thereof described herein, e.g., an antibody or antigen-binding fragment thereof comprising the six CDRs of SEQ ID NO:1-6, the VH of SEQ ID NO:7 or the same amino acid sequence as the VH of the antibody produced by the CGX-c1 hybridoma deposited at the ATCC® as deposit number PTA-125491 on Nov. 14, 2018, the VL of SEQ ID NO:8 or the same amino acid sequence as the VL of the antibody produced by the CGX-c1 hybridoma deposited at the ATCC® as deposit number PTA-125491 on Nov. 14, 2018, the VH of SEQ ID NO:7 and the VL of SEQ ID NO:8 or the same amino acid sequence as the VH of the antibody produced by the CGX-c1 hybridoma deposited at the ATCC® as deposit number PTA-125491 on Nov. 14, 2018, and the same amino acid sequence as the VL of the antibody produced by the CGX-c1 hybridoma deposited at the ATCC® as deposit number PTA-125491 on Nov. 14, 2018, a heavy chain comprising the same amino acid sequence as the heavy chain of the antibody produced by the CGX-c1 hybridoma deposited at the ATCC® as deposit number PTA-125491 on Nov. 14, 2018, a light chain comprising same amino acid sequence as the light chain of the antibody produced by the CGX-c1 hybridoma deposited at the ATCC® as deposit number PTA-125491 on Nov. 14, 2018, or a heavy chain comprising the same amino acid sequence as the heavy chain of the antibody produced by the CGX-c1 hybridoma deposited at the ATCC® as deposit number PTA-125491 on Nov. 14, 2018, and a light chain comprising the same amino acid sequence as the light chain of the antibody produced by the CGX-c1 hybridoma deposited at the ATCC® as deposit number PTA-125491 on Nov. 14, 2018. Thus, provided herein are host cells containing a polynucleotide encoding an antibody or antigen-binding fragment thereof described herein, e.g., an antibody or antigen-binding fragment thereof comprising the six CDRs of SEQ ID NOs:1-6, the VH of SEQ ID NO:7 or the same amino acid sequence as the VH of the antibody produced by the CGX-c1 hybridoma deposited at the ATCC® as deposit number PTA-125491 on Nov. 14, 2018, the VL of SEQ ID NO:8 or the same amino acid sequence as the VL of the antibody produced by the CGX-c1 hybridoma deposited at the ATCC® as deposit number PTA-125491 on Nov. 14, 2018, the VH of SEQ ID NO:7 and the VL of SEQ ID NO:8 or the same amino acid sequence as the VH of the antibody produced by the CGX-c1 hybridoma deposited at the ATCC® as deposit number PTA-125491 on Nov. 14, 2018, and the same amino acid sequence as the VL of the antibody produced by the CGX-c1 hybridoma deposited at the ATCC® as deposit number PTA-125491 on Nov. 14, 2018, a heavy chain comprising same amino acid sequence as the heavy chain of the antibody produced by the CGX-c1 hybridoma deposited at the ATCC® as deposit number PTA-125491 on Nov. 14, 2018, a light chain comprising the same amino acid sequence as the light chain of the antibody produced by the CGX-c1 hybridoma deposited at the ATCC® as deposit number PTA-125491 on Nov. 14, 2018, or a heavy chain comprising the same amino acid sequence as the heavy chain of the antibody produced by the CGX-c1 hybridoma deposited at the ATCC® as deposit number PTA-125491 on Nov. 14, 2018, and a light chain comprising the same amino acid sequence as the light chain of the antibody produced by the CGX-c1 hybridoma deposited at the ATCC® as deposit number PTA-125491 on Nov. 14, 2018, operably linked to a promoter for expression of such sequences in the host cell. In certain aspects, for the expression of double-chained antibodies or antigen-binding fragments thereof, vectors encoding both the heavy and light chains, individually, can be co-expressed in the host cell for expression of the entire immunoglobulin, as detailed below. In certain aspects, a host cell contains a vector comprising a polynucleotide encoding both the heavy chain and light chain of an antibody described herein or a domain thereof. In specific aspects, a host cell contains two different vectors, a first vector comprising a polynucleotide encoding a heavy chain or a heavy chain variable region of an antibody or antigen-binding fragment thereof described herein, and a second vector comprising a polynucleotide encoding a light chain or a light chain variable region of an antibody described herein (e.g., an antibody comprising the six CDRs of SEQ ID NOs:1-6), or a domain thereof. In other aspects, a first host cell comprises a first vector comprising a polynucleotide encoding a heavy chain or a heavy chain variable region of an antibody or antigen-binding fragment thereof described herein, and a second host cell comprises a second vector comprising a polynucleotide encoding a light chain or a light chain variable region of an antibody or antigen-binding fragment thereof described herein (e.g., an antibody or antigen-binding fragment thereof comprising the six CDRs of SEQ ID NOs:1-6). In specific aspects, a heavy chain/heavy chain variable region expressed by a first cell associated with a light chain/light chain variable region of a second cell to form an anti-TREM2 antibody or antigen-binding fragment thereof described herein (e.g., antibody or antigen-binding fragment thereof comprising the six CDRs of SEQ ID NOs:1-6). In certain aspects, provided herein is a population of host cells comprising such first host cell and such second host cell.

In a particular aspect, provided herein is a population of vectors comprising a first vector comprising a polynucleotide encoding a light chain/light chain variable region of an anti-TREM2 antibody or antigen-binding fragment thereof described herein, and a second vector comprising a polynucleotide encoding a heavy chain/heavy chain variable region of an anti-TREM2 antibody or antigen-binding fragment thereof described herein (e.g., antibody or antigen-binding fragment thereof comprising the CDRs of SEQ ID NOs:1-6). Alternatively, a single vector can be used which encodes, and is capable of expressing, both heavy and light chain polypeptides.

A variety of host-expression vector systems can be utilized to express antibodies and antigen-binding fragments thereof described herein (e.g., an antibody or antigen-binding fragment thereof comprising the CDRs of SEQ ID NOs:1-6) (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody or antigen-binding fragment thereof described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific aspect, cells for expressing antibodies and antigen-binding fragments thereof described herein (e.g., an antibody or antigen-binding fragment thereof comprising the CDRs of SEQ ID NOs:1-6) are CHO cells, for example CHO cells from the CHO GS System™ (Lonza). In a particular aspect, cells for expressing antibodies described herein are human cells, e.g., human cell lines. In a specific aspect, a mammalian expression vector is pOptiVEC™ or pcDNA3.3. In a particular aspect, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In certain aspects, antibodies or antigen-binding fragments thereof described herein are produced by CHO cells or NS0 cells.

In addition, a host cell strain can be chosen which modulates the expression of the inserted sequences, or modifies and processes the gene product in the specific fashion desired. Such modifications (e.g., glycosylation) and processing (e.g., cleavage) of protein products can contribute to the function of the protein. To this end, eukaryotic host cells that possess the cellular machinery for proper processing of the primary transcript, glycosylation, and phosphorylation of the gene product can be used. Such mammalian host cells include but are not limited to CHO, VERO, BHK, HeLa, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain aspects, anti-TREM2 antibodies described herein (e.g., an antibody or antigen-binding fragment thereof comprising the CDRs of SEQ ID NOs:1-6) are produced in mammalian cells, such as CHO cells, e.g., CHO-K1 cells. In certain aspects, anti-TREM2 antibodies described herein (e.g., an antibody or antigen-binding fragment thereof comprising the CDRs of SEQ ID NOs:1-6) are produced in mammalian cells, such as HEK-293 cells, e.g., 293F cells.

In some aspects, a signal peptide is used in constructing a vector containing the VH and/or VL or the heavy and/or light chain of an antibody or antigen-binding fragment thereof provided herein.

Once an antibody or antigen-binding fragment thereof described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or antigen-binding fragments thereof described herein can be fused to heterologous polypeptide sequences described herein or otherwise known in the art to facilitate purification.

In specific aspects, an antibody or antigen-binding fragment thereof described herein is isolated or purified. Generally, an isolated antibody or antigen-binding fragment thereof is one that is substantially free of other antibodies or antigen-binding fragments thereof with different antigenic specificities than the isolated antibody or antigen-binding fragment thereof. For example, in a particular aspect, a preparation of an antibody or antigen-binding fragment thereof described herein is substantially free of cellular material and/or chemical precursors.

IV. Pharmaceutical Compositions Comprising Anti-TREM2 Antibodies and Antigen-Binding Fragments Thereof Provided herein are compositions comprising an antibody or antigen-binding fragment thereof described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed.

In various aspects, compositions comprising an anti-TREM2 antibody or antigen-binding fragment thereof are provided in formulations with a pharmaceutically acceptable carrier (see, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)).

Pharmaceutical compositions described herein can be useful in inhibiting neuroinflammation, decreasing amyloid plaques, and/or increasing the uptake of beta amyloid (e.g., by microglia). Pharmaceutical compositions described herein can be useful in improving cognition and/or attenuating cognitive decline. Pharmaceutical compositions described herein can be useful in treating a condition such as a neurodegenerative disease or disorder.

The pharmaceutical compositions described herein are in one aspect for use as a medicament. The pharmaceutical compositions described herein are in one aspect for use as a diagnostic, e.g., to detect the presence of TREM2 in a sample obtained from a patient (e.g., a human patient). The pharmaceutical compositions described herein can also be used as a diagnostic to detect the presence of soluble TREM2 in a sample, e.g., a CSF or serum sample or brain biopsy, obtained from a patient (e.g., a human patient).

The compositions to be used for in vivo administration can be sterile. This is readily accomplished by filtration through, e.g., sterile filtration membranes.

In some aspects, pharmaceutical compositions are provided, wherein the pharmaceutical composition comprises anti-TREM2 antibodies or antigen-binding fragments thereof described herein and a pharmaceutically acceptable carrier.

In some aspects, a pharmaceutical composition comprises (i) an isolated antibody or antigen-binding fragment thereof that specifically binds to human TREM2, comprising (a) the complementarity determining region (CDR) H1, CDR H2, CDR H3 and CDR L1, CDR L2, and CDR L3 sequences of SEQ ID NOs:1-6, respectively, (b) the same amino acid sequence as the VH of the antibody produced by the CGX-c1 hybridoma deposited at the ATCC® as deposit number PTA-125491 on Nov. 14, 2018, and the same amino acid sequence as the VL of the antibody produced by the CGX-c1 hybridoma deposited at the ATCC® as deposit number PTA-125491 on Nov. 14, 2018, or (c) the same amino acid sequence as the heavy chain of the antibody produced by the CGX-c1 hybridoma deposited at the ATCC® as deposit number PTA-125491 on Nov. 14, 2018, and the same amino acid sequence as the light chain of the antibody produced by the CGX-c1 hybridoma deposited at the ATCC® as deposit number PTA-125491 on Nov. 14, 2018, and (ii) a pharmaceutically acceptable excipient.

V. Methods of Using Anti-TREM2 Antibodies and Antigen-Binding Fragments Thereof Va. Therapeutic and Prophylactic Uses In one aspect, presented herein are methods for treating or preventing a neurodegenerative disease or disorder in a subject, comprising administering to a subject in need thereof an anti-TREM2 antibody or antigen-binding fragment thereof described herein, or a pharmaceutical composition thereof as described above and herein.

In another aspect, an anti-TREM2 antibody or antigen-binding fragment thereof, or pharmaceutical composition, is administered to a patient (e.g., a human patient) to decrease amyloid plaques. In another aspect, an anti-TREM2 antibody or antigen-binding fragment thereof, or pharmaceutical composition, is administered to a patient (e.g., a human patient) to increase beta amyloid uptake (e.g., by microglia). In another aspect, an anti-TREM2 antibody or antigen-binding fragment thereof, or pharmaceutical composition, is administered to a patient (e.g., a human patient) to reduce soluble TREM2. In another aspect, an anti-TREM2 antibody or antigen-binding fragment thereof, or pharmaceutical composition, is administered to a patient (e.g., a human patient) to attenuate neuroinflammation.

In another aspect, an anti-TREM2 antibody or antigen-binding fragment thereof, or pharmaceutical composition, is administered to a patient (e.g., a human patient) to improve cognition. In another aspect, an anti-TREM2 antibody or antigen-binding fragment thereof, or pharmaceutical composition, is administered to a patient (e.g., a human patient) to attenuate cognitive decline. Cognition can be assessed, for example, using a Morris Water Maze and/or a Novel Object Recognition assay, as described herein.

Usually, the patient is a human, but non-human mammals including transgenic mammals can also be treated.

In some aspects, the present invention relates to an antibody or antigen-binding fragment thereof or pharmaceutical composition provided herein for use as a medicament. In some aspects, the present invention relates to an antibody or antigen-binding fragment thereof or pharmaceutical composition provided herein, for use in a method for the treatment or prevention of a neurodegenerative disease or disorder. In some aspects, the present invention relates to an antibody or antigen-binding fragment thereof or pharmaceutical composition provided herein, for use in a method for the treatment or prevention of neurodegenerative disease or disorder in a subject, comprising administering to the subject an effective amount of an antibody or antigen-binding fragment thereof or pharmaceutical composition provided herein.

An antibody or antigen-binding fragment thereof or composition described herein can be delivered to a subject by a variety of routes, such as parenteral, subcutaneous, intravenous, intradermal, transdermal, intrathecal, and intranasal. In one aspect, the antibody or antigen-binding fragment thereof or composition is administered by an intraperitoneal route.

The amount of an antibody or antigen-binding fragment thereof or composition which will be effective in the treatment or prevention of a condition will depend on the nature of the disease. The precise dose to be employed in a composition will also depend on the route of administration, and the seriousness of the disease.

In one aspect, an anti-TREM2 antibody or antigen-binding fragment thereof can be used to target a therapeutic (e.g., a therapeutic linked or fused to the anti-TREM2 antibody or antigen-binding fragment thereof) to microglial cells.

Vb. Detection and Diagnostic Uses

An anti-TREM2 antibody or antigen-binding fragment thereof described herein can be used to assay TREM2 protein levels (e.g., soluble TREM2 protein levels) in a biological sample using classical methods known to those of skill in the art, including immunoassays, such as the enzyme linked immunosorbent assay (ELISA), fluorescence-activated cell sorting (FACS), immunohistochemistry (IHC), immunoprecipitation, and Western blotting. Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody or antigen-binding fragment thereof described herein. Alternatively, a second antibody or antigen-binding fragment thereof that recognizes an anti-TREM2 antibody or antigen-binding fragment thereof described herein can be labeled and used in combination with an anti-TREM2 antibody or antigen-binding fragment thereof to detect TREM2 protein levels (e.g., soluble TREM2 protein levels).

Assaying for the expression level of TREM2 protein is intended to include qualitatively or quantitatively measuring or estimating the level of a TREM2 protein in a first biological sample either directly (e.g., by determining or estimating absolute protein level) or relatively (e.g., by comparing to the disease associated protein level in a second biological sample). TREM2 polypeptide expression level in the first biological sample can be measured or estimated and compared to a standard TREM2 protein level, the standard being taken from a second biological sample obtained from an individual not having the disorder or being determined by averaging levels from a population of individuals not having the disorder. As will be appreciated in the art, once the "standard" TREM2 polypeptide level is known, it can be used repeatedly as a standard for comparison.

As used herein, the term "biological sample" refers to any biological sample obtained from a subject, cell line, tissue, or other source of cells potentially expressing TREM2. Methods for obtaining tissue biopsies and body fluids from animals (e.g., humans) are well known in the art. A biological sample may also be a blood sample.

An anti-TREM2 antibody or antigen-binding fragment thereof described herein can be used for prognostic, diagnostic, monitoring, and screening applications, including in vitro and in vivo applications well known and standard to the skilled artisan and based on the present description. Prognostic, diagnostic, monitoring, and screening assays and kits for in vitro assessment and evaluation of TREM2 presence may be utilized to predict, diagnose and monitor to evaluate patient samples including those known to have or suspected of having a neurodegenerative disease or disorder. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses.

Anti-TREMs antibodies and antigen-binding fragments thereof described herein can carry a detectable or functional label.

Examples of detectable moieties that can be used herein include but are not limited to radioactive isotopes, phosphorescent chemicals, chemiluminescent chemicals, fluorescent chemicals, enzymes, fluorescent polypeptides, and epitope tags. The detectable moiety can be a member of a binding pair, which is identifiable via its interaction with an additional member of the binding pair, and a label which is directly visualized.

When fluorescence labels are used, currently available microscopy and fluorescence-activated cell sorter analysis (FACS) or combination of both methods procedures known in the art may be utilized to identify and to quantitate the specific binding members. Anti-TREM2 antibodies or antigen-binding fragments thereof described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-TREM2 antibody can carry a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of anti-TREM antibody or antigen-binding fragment to TREM2 (e.g., human TREM2). In the instance where the label is an enzyme, detection may be accomplished by any of the presently utilized colorimetric, spectrophotometric, fluorospectrophotometric, amperometric, or gasometric techniques as known in the art. This can be achieved by contacting a sample or a control sample with an anti-TREM2 antibody or antigen-binding fragment thereof under conditions that allow for the formation of a complex between the antibody or antigen-binding fragment thereof and TREM2. Any complexes formed between the antibody or antigen-binding fragment thereof and TREM2 are detected and compared in the sample and the control. The antibodies or antigen-binding fragments thereof described herein can also be used to purify TREM2 via immunoaffinity purification.

Also included herein is an assay system which may be prepared in the form of a test kit for the quantitative analysis of the extent of the presence of, for instance, TREM2 (e.g. soluble TREM2). The system or test kit may comprise a labeled component, e.g., a labeled antibody or antigen-binding fragment, and one or more additional immunochemical reagents. See, e.g., Section VI below for more on kits.

In some aspects, methods for in vitro detecting TREM2 in a sample, comprising contacting said sample with an antibody or antigen-binding fragment thereof, are provided herein, and optionally detecting binding of the antibody or antigen-binding fragment thereof to TREM2. In some aspects, provided herein is the use of an antibody or antigen-binding fragment thereof provided herein, for in vitro detecting TREM2 in a sample. In one aspect, provided herein is an antibody or antigen-binding fragment thereof or pharmaceutical composition provided herein for use in the detection of TREM2 (e.g., soluble TREM2) in a subject or a sample obtained from a subject. In one aspect, provided herein is an antibody or antigen-binding fragment thereof or pharmaceutical composition provided herein for use as a diagnostic. In one aspect, the antibody comprises a detectable label.

In one aspect, the subject is a human.

VI. Kits

Provided herein are kits comprising one or more antibodies or antigen-binding fragments thereof described herein or conjugates (e.g., detection conjugates) thereof. As provided herein, kits can be used in diagnostic methods. In one aspect, a kit comprises an antibody or antigen-binding fragment thereof described herein, preferably a purified antibody or antigen-binding fragment thereof, in one or more containers.

In a specific aspect, kits described herein contain a substantially isolated TREM2 antigen (e.g., human TREM2) that can be used as a control. In specific aspects, a kit provided herein can include a recombinantly produced or chemically synthesized TREM2 antigen. The TREM2 antigen provided in the kit can also be attached to a solid support.

In another specific aspect, the kits described herein further comprise a control antibody or antigen-binding fragment thereof which does not react with a TREM2 antigen. In another specific aspect, kits described herein contain one or more elements for detecting the binding of an antibody or antigen-binding fragment thereof to a TREM2 antigen (e.g., the antibody or antigen-binding fragment thereof can be conjugated to a detectable substrate such as a fluorescent compound, an enzyme, an enzymatic substrate, a radioactive compound, or a luminescent compound, or a second antibody or antigen-binding fragment thereof, which recognizes the first antibody or antigen-binding fragment thereof, can be conjugated to a detectable substrate). In a more specific aspect, the detecting means of the above described kit includes a solid support to which a TREM2 antigen is attached. Such a kit can also include a non-attached reporter-labeled anti-mouse/rodent antibody or antigen-binding fragment thereof. In this aspect, binding of the antibody or antigen-binding fragment thereof to the TREM2 antigen can be detected by binding of the said reporter-labeled antibody or antigen-binding fragment thereof.

In another specific aspect, the kits described herein further comprise a therapeutic anti-TREM2 antibody or antigen-binding fragment thereof and/or information that a therapeutic anti-TREM2 antibody or antigen-binding fragment thereof should be administered when TREM2 is detected in a sample using an anti-TREM2 antibody or antigen-binding fragment thereof provided herein.

EXAMPLES

Materials and Methods

Animals

5×FAD and hTau.K257T/P301S animals were bred in house (mutations were analyzed using specific primers for PCR genotyping). All housing, breeding, and procedures were reviewed and approved by "The Israel Board for Animal Experiments" and in compliance with "The Israel Animal Welfare Act." Animals were housed under standard laboratory conditions, air conditioned and filtered (HEPA F6/6) with adequate fresh air supply (minimum 15 air changes/hour). Animals were kept in a climate controlled environment. The temperature range was 20-24° C., and the relative humidity range was 30-70% with a 12 hours light and 12 hours dark cycle.

Transfection of hTREM2, mTREM2, and GFP into HEK293T Cells

Naïve HEK293T cells were transiently transfected with constructs expressing human (HG11084-ACG, Sino Biological) and mouse (MG50149-ACG, Sino Biological) TREM2 (fused at the C-terminus with GFP) using JetPrime mediated transfection (JetPrime, Polyplus-transfection) following manufacturer protocol. Cells transfected with pCDNA-GFP (without an insert gene) were used as sham control.

Lysate Preparation

Cell supernatants, brain, and cell lysates were prepared in hypotonic buffer (0.01 M Tris, pH 7, 1 mM EDTA, 1 mM EGTA) freshly supplemented in a protease inhibitor cocktail (P8340, Sigma)), incubated on ice for 30 minutes, snap frozen, and thawed. The pellets were then resuspended in STE lysis buffer (150 mM NaCl, 50 mM Tris-HCl, pH 7.6, 2 mM EDTA, 1% Triton-X 100) and incubated on ice for 20 minutes before clarifying and supplemented with Laemmli sample buffer for SDS-PAGE protein separation.

Western Blotting 25-30 µg of supernatants/lysates/CSF was loaded in each well for SDS-PAGE protein separation (reduced conditions) on Nuphage 4-12% gels (ThermoFisher Scientific, Cat No. NP0322BOX). Samples were transferred to 0.2 µm nitrocellulose membranes (WhatmanProtan BA83, Cat No. 10401380) and incubated at 4° C. for 12 hours with CGX101 (5 µg/ml) or mouse IgG (5 µg/ml control) as primary antibodies diluted in 1% BSA/TBST followed by goat anti-mouse antibody conjugated to HRP (Jackson, 1:10,000) for an additional 1 hour incubation at room temperature. Membranes were developed using Fusion Solo 7S imager system (Vilber, France).

Human Subjects and Tissue Sampling

Human studies were performed at Kaplan Medical Centre in Rehovot, Israel, under appropriate Institutional Review Board approval. Blood samples were obtained from the Israel National Blood Services (MDA) except for CSF and brain specimens included in the study which were collected at the Cambridge Brain Bank supported by the NIHR Cambridge Biomedical Research Centre.

Novel Object Recognition (NOR)

24 hours before testing, all animals were habituated to the testing apparatus for 10 minutes (50 cm box, 40 cm high). The day after, animals were introduced to objects: first, two identical objects were placed in the box, and mice were allowed to explore the objects for 5 minutes. The same procedure continued until 5 mice were done. The entire phase for 5 mice lasted 30 minutes. Immediately after, these 5 mice were tested in the same order as before. Animals were introduced to two different objects, one familiar object and one novel object that the mice never encountered. Mice were allowed to explore the objects for 5 minutes and then removed from the box. At all phases, after each mouse was removed from the box, the box was sterilized with alcohol. Sample and novel objects and their locations were counter-balanced across animals. Each trial was videotaped, and the time and frequency spent with each object was measured using NoldusEthoVision XT 11.5 (Noldus information Technology, The Netherlands). Memory was operationally defined by the discrimination index for the novel object (DI) as the proportion of time animals spent investigating the novel object minus the proportion spent investigating the familiar one in the testing period [Discrimination Index, DI=(Novel Object Exploration Time–Familiar Object Exploration Time)/(Novel Exploration Time+Familiar Object Exploration)].

Morris Water Maze (MWM)

The Morris Water Maze task requires mice to find a submerged platform in a large circular pool of water. This version of the task is a reference memory task where mice solve the task by learning the spatial relationships between the platform location and the extra-maze landmarks in the testing environment. The experimental apparatus consisted of a circular water tank (diameter=100 cm; height=40 cm) containing water at 22° C. to a depth of 32 cm. A platform (10×10 cm) was submerged 1 cm below the water surface and placed at the midpoint of one quadrant. The pool was placed in a test room homogenously brightened and containing various prominent cues. Mice were transferred from the housing facility to the behavior room at least 30 minutes before testing to adjust to the new environment. The swimming paths of the animals were recorded using a video tracking system. On day 1, navigation to a visible platform (clear water in the tank and a flag on the platform to increase visibility) was carried out to evaluate visual and motor abilities of animals, and both the platform and starting direction change in each trial (pool was divided to 4 quadrants). Mice were gently placed into the water, facing the edge of the pool. If they failed to find the platform after 60 seconds, they were guided to its location and allowed to stay there for 20 seconds before returning them to their home cage. Mice that managed to find the platform were allowed to stay 5 seconds before their return. Mice were submitted to 5 trials per day with an inter-trial interval of at least 45 minutes.

On days 2-5, the flag was removed from the platform, and aqueous acrylic emulsion paint was added to the water so that the submerged platform was not visible from the surface of the water. Memory-acquisition trials (training) were performed five times daily with a 45-minute inter-trial interval to reach a steady state of escape latency. The platform position remained constant while the starting direction changed. Mice failing to find the platform within 60 seconds were placed on the platform for 20 seconds at the end of the trial. On day 6, the platform was removed from the pool, and the starting direction for the single trial was at the farthest (North) point from the platform quadrant used on day 2-5 (Southwest) so that the mice would travel some distance before entering the previously learned platform quadrant. One probe trial (60 seconds long) was performed for each animal. NoldusEthoVision XT 11.5 (Noldus information Technology, The Netherlands) software was used so that the camera can create physical distance information from pixel-based information after calibrating and defining parameters (dividing pool into 4 quadrants) in order to track path length, escape latency, and time spent in each quadrant.

Statistical Analysis

Values shown in the Figures are presented as mean+/−SEM. P values for determination of the statistical significance of differences were calculated by means of paired, two-tailed Student's t test, one-way ANOVA with a post hoc Dunnet's or one-way ANOVA with Tukey's post test.

Example 1: Generation of Monoclonal Antibodies and Assessment of their Binding to TREM2

Figure 1:
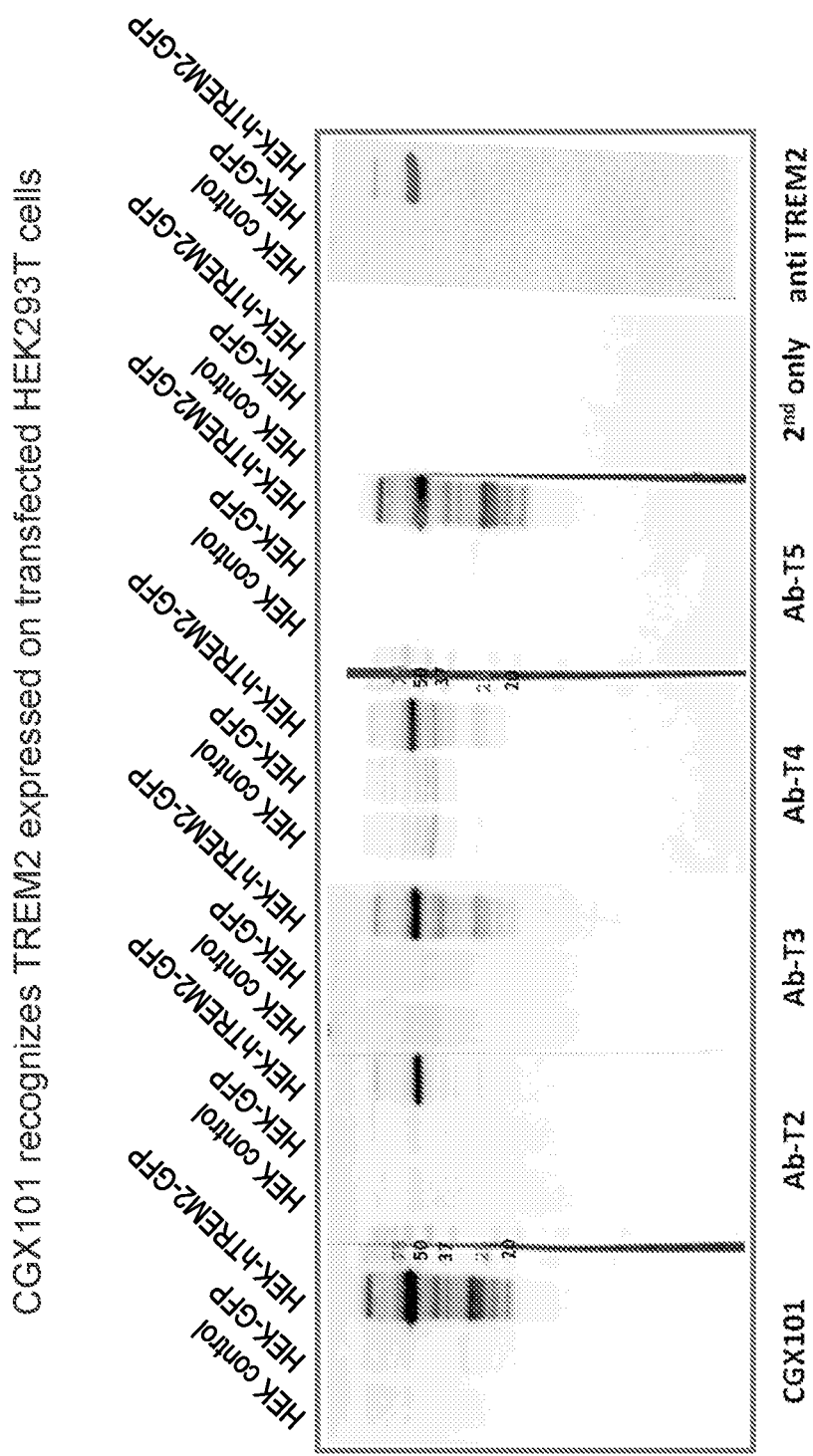

Several clones of monoclonal antibodies (mAbs) were produced according to standard protocols by Balb/C mice immunization with 50 µg of human TREM2 protein (GenScript, USA) followed by three additional boosts. After confirming the presence of polyclonal anti-TREM2 antibodies (Abs) in the sera, mice were sacrificed. Cells were isolated from their spleens and hybridized with an SP2/0 myeloma line, followed by clonal screening for binding to human TREM2. The hybridomas were then grown in serum-free media for 2-3 weeks, and media were collected and concentrated by 30 kDa centricons (Biological Industries, Israel). The cross-reactivity of mAbs with human TREM2 was confirmed by Western blot. A standard Western blot assay was performed evaluating the binding characteristics and affinity of 5 identified clones (CGX101, Ab-T2, Ab-T3, Ab-T4, Ab-T5) and a control anti-TREM2 Ab (Cat #MAB2056, clone 2B5, Abnova) to HEK293T cells expressing human TREM2. The binding is shown in FIG. 1.

Figure 2A:
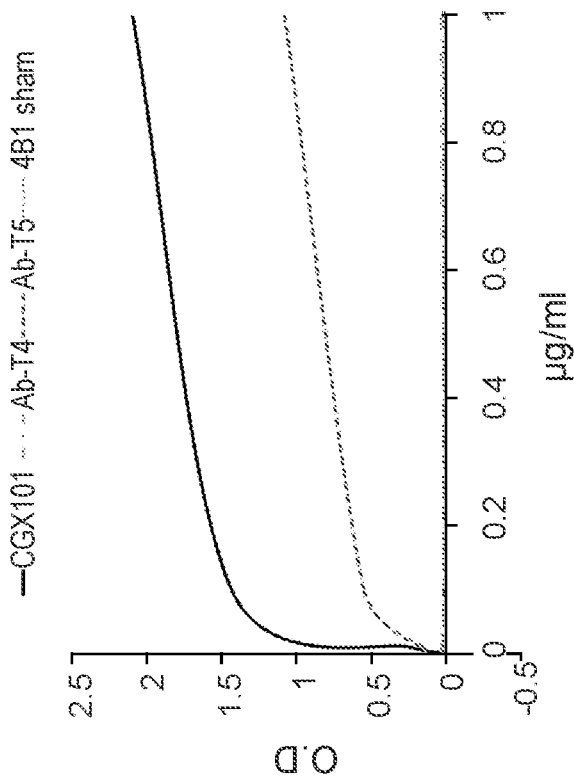
FIG. 2A is a graph showing the binding of CGX101, Ab-T4, Ab-T5, and a negative control ("4B1 sham") to the extracellular domain (ECD) of human TREM2 by ELISA assay. (See Example 1.)
Figure 2B:
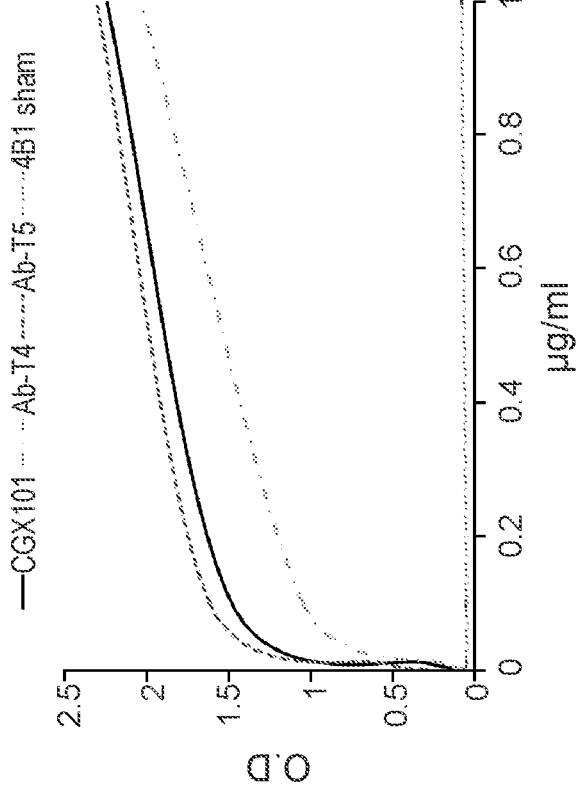
FIG. 2B is a graph showing the binding of CGX101, Ab-T4, Ab-T5, and a negative control ("4B1 sham") to mouse TREM2 by ELISA assay. (See Example 1.)
Figure 2C:
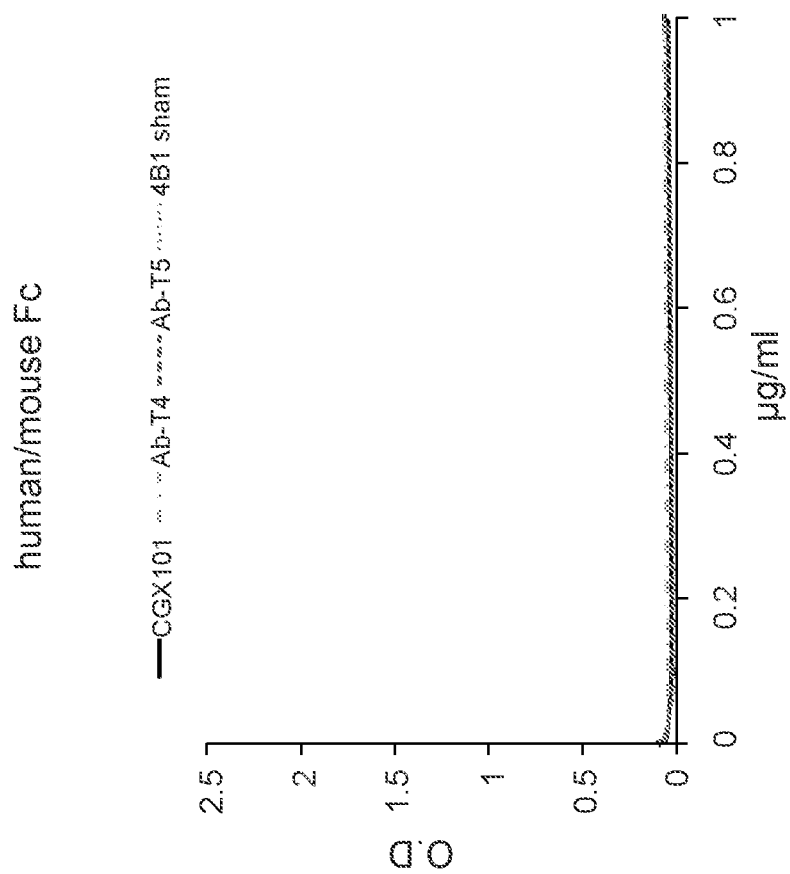
FIG. 2C is a graph showing the binding of CGX101, Ab-T4, Ab-T5, and a negative control ("4B1 sham") to a combination of human and mouse Fc proteins by ELISA assay. (See Example 1.)

In order to further analyze binding to TREM2, a standard ELISA assay was performed using different species of TREM2 as the coating protein. CGX101 binds both the extracellular domain of human TREM2 (FIG. 2A) and mouse TREM2 (FIG. 2B) in a concentration-dependent manner, while it does not bind to mouse and human Fc (FIG. 2C). Ab-T5 binds to human TREM2 with higher affinity than mouse TREM2 (FIGS. 2A and 2B). Ab-T4 only binds to human TREM2 and has a lower affinity for human TREM2 than CGX101 and Ab-T5 (FIG. 2A). Sham did not show binding at all (FIGS. 2A-C).

Figure 3:
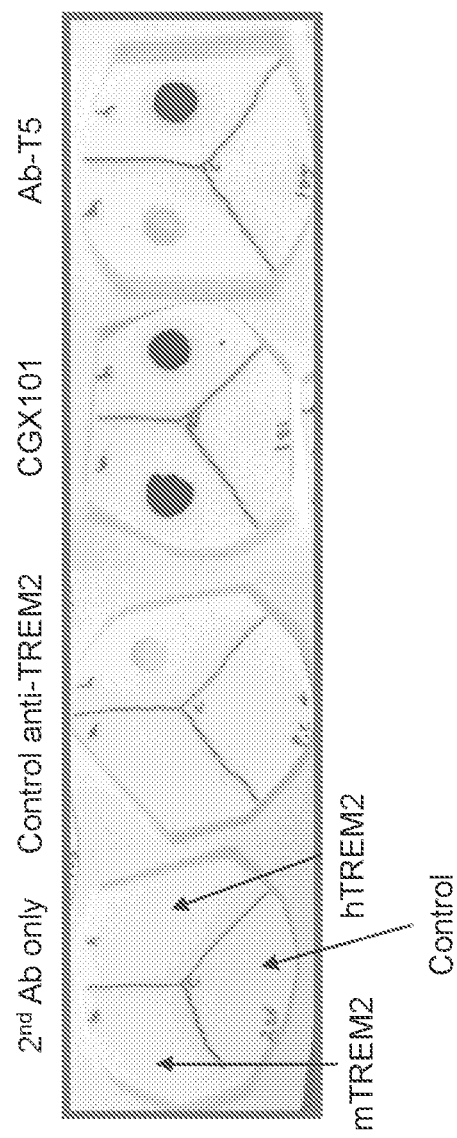
FIG. 3 is a dot-blot assay showing the binding of CGX101, Ab-5, and a control anti-TREM2 antibody to mouse TREM2 ("mTREM2") and human TREM2 ("hTREM2") in HEK293T cells or to HEK293T cells that were not transfected with TREM2-encoding sequences ("control"). (See Example 1.)

The two antibodies with the most desirable TREM2-binding activities (i.e., CGX101 and Ab-T5) were further analyzed using dot blot assays. The dot blot assays assessed binding of the antibodies to transfected HEK293T cells expressing human or mouse TREM2 (FIG. 3). CGX101 binds with high affinity both human and mouse TREM2, but does not bind to control HEK293T cells (FIG. 3). Ab-T5 binds to transfected HEK293T cells expressing mouse TREM2 with lower affinity than human TREM2 (FIG. 3).

The ability of CGX101 to bind cellular TREM2 was also assessed by immunostaining non-permeabilised HEK293T cells transfected with a wild-type human TREM2-GFP fusion protein. In these assays, transfected HEK293T cells (HEK293T-hTREM2-GFP/HEK293T) were seeded (0.2× $10^6$/well in a 12 well plate) on cover slips coated with 0.1 mg/ml Poly-L-Lysine (Sigma) and blocked in 20 mM HBSS (Gibco) supplemented with 10% FBS for 45 minutes at room temperature. The cells were incubated with 0.5 and 1 µg/ml mouse CGX101 conjugated to Cy5 (mCGX101-Cy5) as primary antibody (diluted in above blocking buffer) for 1 hour at room temperature followed by additional 1 hour at 4° C. Control experiment used mouse IgG as the primary antibody. Cells were rinsed twice with ice-cold PBS and fixed in 4% v/v paraformaldehyde for 12 min at room temperature. Cells on cover slips were washed 3 times in ice cold PBS and laid down on a slide with a drop of mounting buffer (DAPI Fluoromount-G, SouthernBiotech) before being visualized on a confocal laser scanning microscope (TCS SP8, Leica). The results showed that CGX101 bound to transfected, but not to non-transfected, cells.

Example 2: Humanized CGX101 Exhibits High Affinity to Human and Mouse TREM2 Extracellular Domain by Biacore A Surface Plasmon Resonance (Biacore) assay was used to assess the binding of humanized CGX101 (hCGX101), an IgG4 antibody, to the extracellular domain of human TREM2 and to a protein containing the extracellular domain of mouse TREM2 fused to Fc. The results, which are reported in Table 5 below, demonstrate that hCGX101 has a high binding affinity for both proteins.

TABLE 5

Surface Plasmon Resonance (Biacore) Analysis of CGX101 Binding

| TREM2 | $Ka^1$ (1/Ms) | $Kd^2$ (1/s) | $KD^3$ (M) | $KD^3$ (nM) |
|---|---|---|---|---|
| Human TREM2-ECD | 1.246E+5 | 7.148E−4 | 5.739E−9 | 5.73 |
| Mouse TREM2-Fc | 5.699E+4 | 0.001061 | 1.862E−8 | 18.62 |

[1]Ka = association rate constant
[2]Kd = dissociation rate constant
[3]KD = affinity constant

Example 3: Humanized CGX101 does not Trigger Inflammation by PBMCs

The effect of hCGX101 on peripheral blood mononuclear cells (PBMCs) was examined.

To isolate and culture PBMCs, whole blood was diluted at a 1:1 ratio with PBS (Ca/Mg free), gently laid in ficoll (ratio 1:2), and centrifuged for 30 minutes at 1500 rotations per minute (rpm; with slow acceleration and de-acceleration (0)). Buffy coat was collected into a new tube, washed with PBS, and centrifuged for 15 minutes at 1200 rpm. An additional wash with PBS was performed, and blood was centrifuged for 15 minutes at 1200 rpm before cells were resuspended in 10 ml PBS for counting.

The PBMCs were incubated with hCGX101, a control antibody (human IgG), or LPS (positive control). Then, after 18 hours, TNF-alpha (TNFa) protein levels in cells were detected using DuoSet Elisa assay (R&D System) following the manufacturer's protocol.

Figure 4:
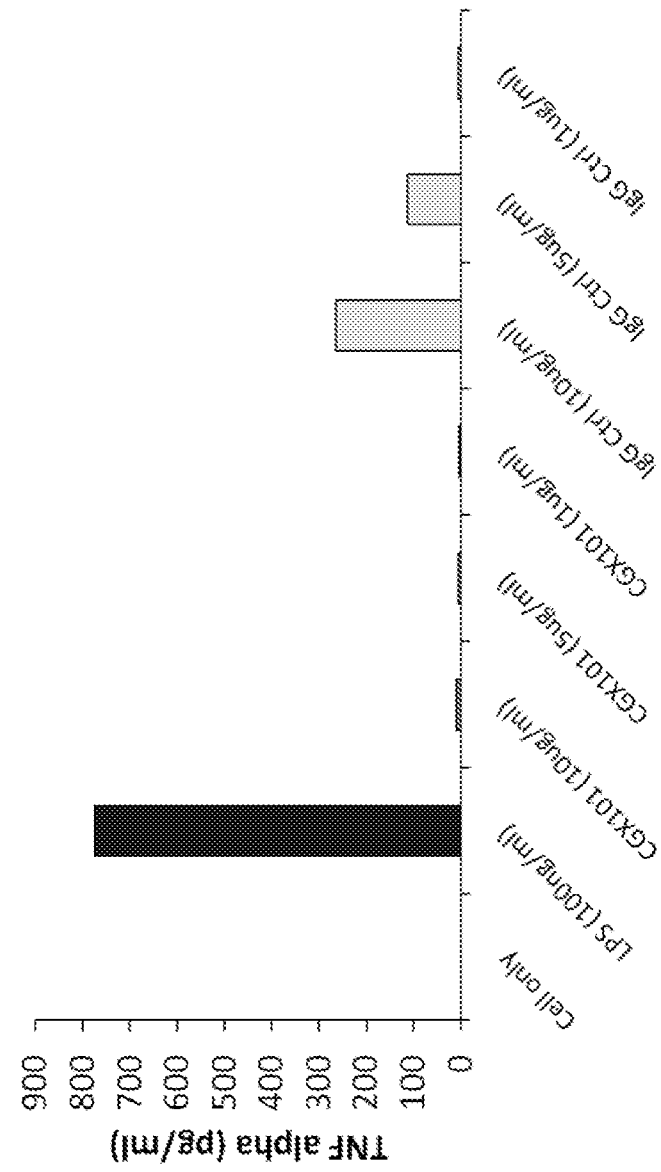
FIG. 4 is a graph showing TNF-alpha protein levels (pg/ml) measured in an ELISA assay 18 hours after incubation of peripheral blood mononuclear cells (PBMCs) with humanized CGX101 (hCGX101), human IgG ("IgG Ctrl), or LPS began. (See Example 3.)

The results, shown in FIG. 4, demonstrate that hCGX101 does not trigger inflammation by PBMCs.

Figure 5:
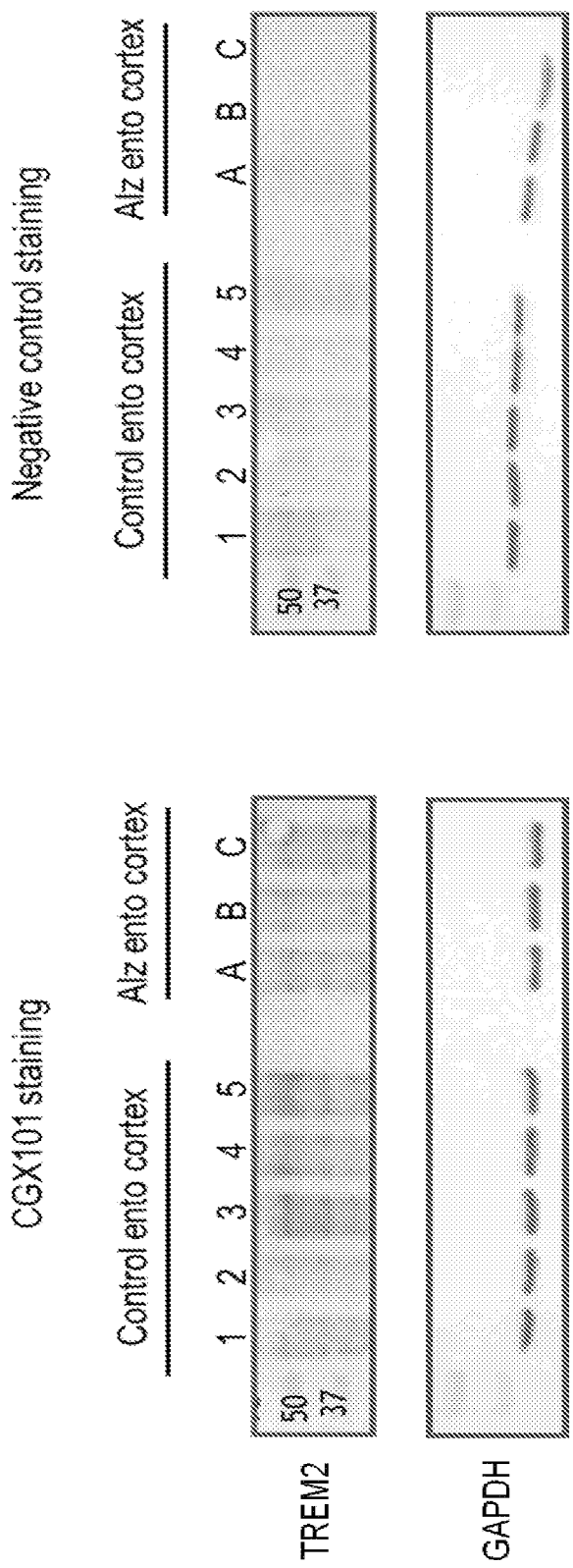
FIG. 5 is a Western Blot showing CGX101 (left panels) and mouse IgG (right panels) binding to human entorhinal cortex extracts from Alzheimer and control group patients' brains. Binding to GAPDH, a housekeeping protein used as a loading control, is shown in lower panels. (See Example 4.)

Example 4: CGX101 Recognizes TREM2 in the Brains of Alzheimer's Disease Patients The ability of CGX101 to bind TREM2 in a human brain (entorhinal cortex) from an AD patient and in control extracts was assessed by Western blot staining. The results, shown in FIG. 5 (left panel), demonstrate that CGX101 binds to TREM2 in human brain. FIG. 5 shows higher binding to AD brain extracts (Alz ento cortex) than to control brain extracts (Control ento cortex). A control murine IgG antibody showed no binding to TREM2 in human entorhinal cortex extracts from either AD patients or control group patients (FIG. 5, right panel).

Example 5: CGX101 Recognizes TREM2 in Brains and Co-Localizes with Microglia and Plaques The ability of CGX101 to bind TREM2 in brains from human AD patients and mouse models of AD was assessed using immunohistochemistry. In these assays, human brain tissue from AD patients and mice brain tissue from 5×FAD mice (which are a murine model for AD) was post-fixed in 4% formalin for 48 hours, dehydrated in ethanol, and embedded in paraffin.

For histological studies of mouse brain, the brain was removed, and the left hemisphere underwent overnight post-fixation with neutral buffered formalin (Thermo Fisher Scientific), before being processed and embedded in O.C.T compound (Ref 4583, Tissue-Tek) for cryosectioning and immunostaining. Immunohistochemical staining was then performed on 4 μm sections using the Leica Bond III system (Leica Biosystems Newcastle Ltd, UK). Tissues were pre-treated with epitope-retrieval solutions (ER, Leica Biosystems Newcastle Ltd, UK) followed by 30 minutes incubation with primary antibodies CGX101 (2.85 μg/ml), anti-Iba-1 (a marker for microglia; 1:1500), anti-beta amyloid (1:600) and mouse IgG4 (1 μg/ml). The Leica Refine-HRP kit (Leica Biosystems Newcastle Ltd, UK) was used for detection followed by counter-stain with hematoxylin.

The staining in brains from human AD patients demonstrate that CGX101 robustly recognizes TREM2 in AD brains and co-localizes with resident microglia (FIG. 6). The staining in brains from 5×FAD mice demonstrate that CGX101 also robustly recognizes TREM2 in brains from 5×FAD mice and co-localizes with both resident microglia and with amyloid-beta plaques (FIG. 7).

Example 6: CGX101 Binds Soluble TREM2 in Supernatants of TREM2-Transfected Cells and in CSF of Human Alzheimer's Disease Patients To determine if CGX101 can bind to soluble TREM2, Western blot assays were performed in supernatants of HEK293T cells transfected with human TREM2 (HEK293T-hTREM2) and in cerebrospinal fluid (CSF) of human AD patients.

CGX101 detected soluble TREM2 in supernatants of HEK293T cells transfected with human TREM2 (HEK293T-hTREM2) and not in naïve HEK293T cells (control) or sham control as shown in FIG. 8A (left panel). Mouse IgG antibody (Control Ab) did not detect any soluble TREM2 in transfected HEK293T cells (FIG. 8A; right panel).

Human CSF derived from AD patients were blotted with CGX101 to determine its ability to bind endogenous soluble human TREM2. CGX101 was able to detect soluble TREM2 from AD patients CSF (FIG. 8B; right panel (Alz 93 and Alz 48)). Control mouse IgG did not detect soluble TREM2 from AD patients CSF (FIG. 8B; left panel (Alz 93 and Alz 48)).

Example 7: Humanized CGX101 Enhances Acute Microglial Activation and Promotes Uptake of Beta Amyloid The effect of hCGX101 on microglial activation and beta amyloid was assessed.

In these experiments, flow cytometry was used to measure the cellular uptake (calculated by relative geomean fluorescent intensity (gMFI)) of beta amyloid oligomers conjugated to Alexa fluor 488 (oABeta(1-42)).

To perform these assays, primary human macrophages were differentiated from peripheral blood monocytes cells (PBMC). After isolation of PBMCs in a ficoll gradient, cells were split into 12-well culture plates (Greiner CELLSTAR multiwell culture plates, $0.4 \times 10^6$ cells/well) and incubated at 37° C., 5% v/v $CO_2$ and 95% v/v $O_2$ for 1 hour in a serum-free medium (RPMI 1640, 2 mM L-Glutamine, 1% Pen/Strep, Biological Industries). Non-adherent, contaminated cells were removed, and the remaining monocytes were differentiated for 10 days with recombinant human Granulocyte-macrophage colony-stimulating factor (GM-CSF, 10 ng/ml; R&D systems) in a full RPMI medium (RPMI 1640, 10% FBS, 2 mM L-Glutamine, 1% Pen/Strep) incubated at 37° C., 5% v/v $CO_2$ and 95% v/v $O_2$.

To prepare beta amyloid oligomers, 1 mg of lyophilized ultra-pure beta amyloid (1-42) monomers (A-1167-2, rPeptide, USA) was thawed at room temperature for 10 minutes, followed by addition of sterile DMSO to a final concentration of 5 mM Aβ and was transferred to a new low-binding, sterile 1.5 ml microcentrifuge tube (Protein LoBind Tube 1.5, Eppendorf tubes, Cat no.: 022431081), followed by addition of cold phenol-free F12 cell culture media (supplemented with 146 mg/L L-Glutamine; BioSource), and diluted to a final concentration of 100 μM Aβ. After 15 seconds of vortex, the tube was placed in 4° C. incubation for 24 hours.

To measure the uptake of the beta amyloid oligomers, different concentrations of hCGX101 (2, 15, and 30 μg/ml) were added to cells with a total of 1 ml/well new culture media (RPMI 1640, 10% FBS, 2 mM L-Glutamine, 1% Pen/Strep) and incubated at 37° C. for 8 hours. Conditioned medium with PBS (without hCGX101) was added to the cells as control. 0.3 μM beta amyloid oligomers (1-42) conjugated with Alexa 488 (oABeta-488) was added directly to cells in the culture plates, and then cells were incubated at 37° C. for an additional 2 hours before harvest (a number of wells were incubated without beta amyloid and hCGX101 treatment as an additional control). Medium was removed, centrifuged, and saved for further analysis in ELISA assay. Extracellular and cell surface oABeta-488 in cell pellet was quenched by incubation of 0.4% trypan blue in PBS (pH 4.4) for 1 minute (adding directly to the cells in the plates). Cells were washed and removed from the culture plate by adding ice cold-PBS containing 2.5 mM EDTA, followed by incubation on ice for 30 minutes. Flow cytometry (FL1—blue laser (488 nm)) was used to measure beta amyloid oligomers (conjugated to ALEXA fluor 488) and uptake was indicated as relative geomean fluorescence intensity (gMFI).

The flow cytometry analysis shows that hCGX101 increases human macrophages cellular uptake of oABeta(1-42) conjugated to Alexa fluor 488 (relative gMFI~170) compared to cells treated with PBS (relative gMFI~100) (FIG. 9A). FIG. 9B shows that hCGX101 increases cellular secretion of TNFa (~180%) relative to sham treatment (PBS).

Example 8: Humanized CGX101 Attenuates Neuroinflammation Induced by Soluble TREM2

To assess the effect of hCGX101 on chronic microglial activation, mice were injected with human TREM2-extracellular domain (ECD) with or without hCGX101 or control antibody (hIgG).

In these experiments, 24 female (n=3, 7, 7, 7) 5×FAD mice (12-14 weeks old) were anesthetized by Isoflurane and stereotaxically injected with human TREM2-ECD (3.6 μg of TREM-ECD per brain) in PBS with and without treatment (7.5 μg of hCGX101 or hIgG4). Control sham C57BL/6JRccHsd 5×FAD animals received sterile PBS (n=3). A single needle insertion (coordinates: −2.2 mm relative to bregma, 2.0 mm from midline) into the right hemisphere was used to target the inoculum to the hippocampus located at a depth of 2 mm below the dura. Material was injected via a 10 μl Hamilton syringe at a rate of 0.4 μl per min (5 μl total volume) with the needle in place (33G) for ≥10 min at each target. Animals were inoculated at the right hemisphere unless otherwise indicated. 24 hours post-intrahippocampal injections, animals were sacrificed, and brains were dissected and homogenized.

To examine neuroinflammation, relative quantitation of gene expression was conducted by real time PCR carried out using TaqMan® Gene Expression Assay (Applied Biosystems). RNA was isolated from homogenized brains using SV total RNA isolation system kit (Promega) following the manufacturer's protocol. Complementary DNA (cDNA) synthesis was carried out with qScript cDNA Synthesis Kit (Quanta bio) using 2 μg of total RNA as template. Fluorescent (FAM)-labeled IL-6, TNFa, INFγ, and IL-1b were normalized to an internal control, GAPDH. All comparisons refer to sham. Analysis was done using the Comparative Ct Method (ΔΔCT).

The expression of a panel of pro-inflammatory cytokines (TNF-alpha, IL-6, and INF-gamma) was assessed, and hCGX101 down-regulated all three pro-inflammatory cytokines (FIG. 10).

Example 9: Humanized CGX101 Enhances Plaque Clearance

To determine the effect of hCGX101 on plaques in 5×FAD mice, analysis of beta amyloid plaques was performed in mice treated with hCGX101 or with sham.

In these experiments, 8 male (two groups of n=4) 5×FAD mice (7 months old) were anesthetized by Isoflurane and stereotaxically injected with hCGX101 (4 μg of hCGX101 in each hemisphere) in PBS. Control sham 5×FAD animals received sterile PBS. A single needle insertion (coordinates: −3.52 mm relative to bregma, 2.5 mm from midline) into the right and left hemisphere was used to target the inoculum to the subiculum located at a depth of 1.35 mm below the dura. Material was injected via a 10 μl Hamilton syringe at a rate of 0.4 μl per min (4 μl total volume) with the needle in place (33G) for ≥10 min at each target. Animals were inoculated at both hemispheres. 8 days post-intrasubiculum injections, animals were sacrificed by overdose with ketamine/xylazine. Transcardial perfusion with PBS and 4% formalin was done in all animals. For histological studies (Plaque staining) the brain was removed and underwent overnight post-fixation with neutral buffered formalin (Thermo Fisher Scientific), before being processed and embedded in O.C.T compound (Ref 4583, Tissue-Tek).

Beta amyloid plaques in sections were confirmed using thioflavin S (ThS) fluorescent staining and visualized and scanned using fluorescent microscropy at 4× magnification. Brains from the mice were extracted and post-fixed in 4% PFA for 48 hours and sunk in 30% sucrose. Brains were frozen on a microtome platform and cut to generate 16 and 40 μm thick sections. Sections were mounted on a glass slide and allowed to completely air dry prior to staining. Slides were washed with 70% ethanol (1 minute) and 80% ethanol (1 minute) followed by incubation with filtered thioflavin S (T1892, Sigma) for 15 minutes in the dark. Thioflavin S stained slides were washed with 70% ethanol (1 minute), 80% ethanol (1 minute), and twice with distilled water before mounting in an aqueous mounting media. The green fluorescence stained plaques were visualized with fluorescent microscropy (EVOS FL Auto Cell Imaging System, ThermoFisher Scientific).

The percentage of plaques in the total brains of the mice were analyzed using ImageJ software. Mice treated with hCGX101 had less plaques than mice treated with sham (FIG. 11) demonstrating that intracerebral delivery of hCGX101 enhances amyloid plaque clearance in 5×FAD mice.

Example 10: Humanized CGX101 Improves Cognition and Reduces Amyloid Plaques

To determine the effect of hCGX101 on cognition and plaques in aged 5×FAD mice, behavioral tests and an assay for plaques were performed in aged mice treated with hCGX101 or with a control antibody.

In these experiments, 8 male (2 groups of n=4) 5×FAD mice (8 months of age) were anesthetized by Isoflurane, intraperitoneal (IP) and injected with anti-CD4 (clone GK1.5, InVivoMAb, BE0003-1) for CD4-cell depletion 6 days pre-treatment. Then, mice were treated IP with hCGX101 (10 mg/kg) or PBS as sham control once a week for 2 months. Behavior tests (NOR and MWM) were conducted at various predetermined time points before the mice were sacrificed at 8 weeks from the beginning of experiment. The mice were sacrificed by overdose with ketamine/xylazine, followed by transcardial perfusion with PBS.

For histological studies, the brain was removed, and the right hemisphere underwent overnight post-fixation with neutral buffered formalin (Thermo Fisher Scientific), before being processed and embedded in O.C.T compound (Ref 4583, Tissue-Tek) for sectioning and Thioflavin S (T1892, Sigma) staining, performed as discussed above in Example 9.

The results shown in FIG. 12A demonstrate that in hidden platform tests, hCGX101-treated 5×FAD mice showed a shorter latency to escape onto the hidden platform on the $3^{rd}$ and $4^{th}$ days. In addition, the results shown in FIG. 12B demonstrate that hCGX101-treated 5×FAD mice had fewer beta amyloid plaques. Thus, weekly IP treatment with hCGX101 improves cognition and reduces the number of amyloid plaques in aged male 5×FAD mice.

Example 11: Humanized CGX101 Attenuates Development of Cognition Dysfunction To determine the effect of hCGX101 on the development of cognitive dysfunction, behavioral tests were performed in young mice treated with hCGX101 or with sham.

In these experiments, 21 female (3 groups of n=7) 5×FAD mice (1.5-2 months of age) were anesthetized by Isoflurane, IP injected with anti-CD4 (clone GK1.5, InVivoMAb, BE0003-1) for CD4-cell depletion 6 days pre-treatment. Then, mice were treated IP with hCGX101 (0.5 mg/kg and 5 mg/kg) or PBS as sham control once a week for 2 months. Behavior tests (NOR and MWM) were conducted at various predetermined time points before the mice were sacrificed at 8 weeks from the beginning of experiment. The mice were sacrificed by overdose with ketamine/xylazine, followed by transcardial perfusion with PBS.

As shown in FIG. 13, sham-treated mice exhibited significantly impaired novel object recognition compared to hCGX101-treated animals. This is evidenced by the similar amounts of time that sham-treated mice spent exploring a familiar object and a new object. In these mice, there was no net preference between novel and familiar objects as shown in the reduced discrimination index [Discrimination Index, DI=(Novel Object Exploration Time−Familiar Object Exploration Time)/(Novel Exploration Time+Familiar Object Exploration)]. However, IP treatment with hCGX101 (hCGX101 (0.5 mg/kg); ~0.34) significantly improved cognitive decline compared to the sham-treated animals (Sham; ~−0.05) (FIG. 13).

Example 12: Humanized CGX101 Attenuates Cognitive Decline in Tauopathy AD

To determine the effect of hCGX101 on cognitive decline in a tauopathy AD model, behavioral tests were performed in hTau.K257T/P301A mice treated with hCGX101 or with sham.

In these experiments, 9 male hTau.K257T/P301S mice (6-7 months of age) were anesthetized by Isoflurane, IP injected with anti-CD4 (clone GK1.5, InVivoMAb, BE0003-1) for CD4-cell depletion 5 days pre-treatment. The mice were treated i.p with hCGX101 (10 mg/kg, n=54) or PBS as sham control (n=4) once a week for 5 weeks. Behavior tests (NOR and MWM) were conducted at various predetermined time points before the mice were sacrificed at 5 weeks post-injections by overdose with ketamine/xylazine.

As shown in FIG. 14A, sham-treated hTau.K257T/P301S mice showed cognitive impairment as indicated by the increase in latency to reach the platform in the MWM probe test as compared to hCGX101-treated mice. This is also demonstrated by the heat map in FIG. 14B showing average amounts of time group of mice spent in different areas of the MWM pool. Thus, hCGX101 treatment attenuates cognitive decline in hTau.K257T/P301S mice.

Example 13: Humanized CGX101 Attenuates Neuroinflammation and Cognitive Decline in Female 5×FAD Mice To determine the effect of hCGX101 on neuroinflammation and cognitive decline in female 5×FAD mice, behavioral tests and mRNA-expression level assays were performed in mice treated with hCGX101 or with sham.

In these experiments, 37 female (4 groups of n=9, 9, 10, 9) 5×FAD mice (4-5 months of age) were anesthetized by Isoflurane, IP injected with anti-CD4 (clone GK1.5, InVivoMAb, BE0003-1) for CD4-cell depletion 6 days pre-treatment. Mice were treated i.p with hCGX101 (1 mg/kg and 10 mg/kg, n=9, 10), human IgG (10 mg/kg, n=9), or PBS as sham control (n=9) once every two weeks for 3 months. Behavior tests (NOR and MWM) were conducted at various predetermined time points before the mice were sacrificed at 12 weeks post-injections by overdose with ketamine/xylazine.

In order to examine neuroinflammation, relative quantitation of gene expression was conducted by real time PCR carried out using TaqMan® Gene Expression Assay (Applied Biosystems).

Mice treated with sham (PBS) or human IgG (10 mg/kg) showed cognitive impairment compared to hCGX101 (10 mg/kg)-treated mice as evidenced by increase in latency to reach the platform in the MWM probe test (FIG. 15A) and by the Discrimination Index (DI) for the object recognition testing session (NOR) (FIG. 15B). HCGX101-treatment also resulted in decreased TNFa, IL-1b, and IL-6 expression levels as compared to no treatment (sham) (FIG. 15C). These data demonstrate that twice-monthly dosing of hCGX101 attenuates neuroinflammation and cognitive decline in female 5×FAD mice.

Human beta amyloid (1-42) levels in brain tissue from 5×FAD mice were evaluated using ultrasensitive ELISA assay (Invitrogen, Catalog #: KHB3544) after twice-monthly treatment for three months with sham, an IgG antibody, or hCGX101. The hCGX101-treated mice had 50% reduction in beta amyloid in brain tissue compared to sham-treated animals (FIG. 19).

Example 14: Humanized CGX101 Reduces Soluble TREM2 in CSF and Serum

To determine the effect of hCGX101 soluble TREM2 levels, TREM2 mRNA levels were measured in the CSF and serum of mice treated with hCGX101 or a control (IgG) antibody.

In these experiments, mice were treated with two different concentrations of hCGX101: 1 and 10 mg/kg, and IgG was administered as a control. PBS was injected into animals for sham control. For the biochemical studies, right hemisphere brain tissues were immediately frozen after removal and stored at −80° C. until used. CSF and blood was taken from 20 animals (5 from each group). Blood was examined for hematological and biochemical parameters and TREM2 protein levels in CSF and serum were detected using mouse TREM2 sandwich ELISA kit (Catalog No. LS-F7884, LifeSpanBioSciences Inc) following manufacturer protocol.

As shown in FIG. 16, hCGX101 results in a dose-dependent reduction of soluble TREM2 in both the CSF and serum of mice.

Example 15: Humanized CGX101 does not Influence Hematological or Biochemical Parameters To determine the effect of hCGX101 on hematological and biological parameters, mice were treated twice a month for 12 weeks with hCGX101, a control antibody (hIgG) or PBS (sham). As shown in FIG. 17, none of the parameters tested were affected by hCGX101, even at the highest dose tested (10 mg/ml).

Example 16: Pharmacokinetics of Humanized CGX101

The pharmacokinetics hCGX101 were examined in 5×FAD mice over three months. In these experiments, the mice received IP injections of 1 mg/kg (n=9) or 10 mg/kg (n=10) hCGX101 twice a month. Then, after three months, the concentration of hCGX101, an huIgG4 antibody, was measured in the serum and the brain tissue of the mice. The results are shown in FIGS. 18A and 18B. No huIgG4 was detected in mice treated with PBS. However, huIgG4 was detected in both the serum and brain tissue of mice treated with either 1 mg/kg or 10 mg/kg hCGX101. The presence of hCGX101 in brain tissue after IP injection is advantageous for the treatment of neurodegenerative diseases.

What is claimed is:

1. An antibody or antigen-binding fragment thereof capable of binding human Triggering Receptor Expressed on Myeloid Cells 2 (TREM2), wherein the antibody or antigen-binding fragment thereof comprises a complementary determining region (CDR) H1 comprising the amino acid sequence set forth in SEQ ID NO:1, a CDR H2 comprising the amino acid sequence set forth in SEQ ID NO:2, a CDR H3 comprising the amino acid sequence set forth in SEQ ID NO:3, a CDR L1 comprising the amino acid sequence set forth in SEQ ID NO:4, a CDR L2 comprising the amino acid sequence set forth in SEQ ID NO:5, and a CDR3 L3 comprising the amino acid sequence set forth in SEQ ID NO:6.

2. The antibody or antigen-binding fragment thereof of claim 1, wherein the antibody or antigen-binding fragment thereof comprises a VH comprising the amino acid sequence of SEQ ID NO: 7 and a VL comprising the amino acid sequence of SEQ ID NO:8.

3. The antibody or antigen-binding fragment thereof of claim 1, wherein the antibody or antigen-binding fragment further comprises a heavy chain constant region.

4. The antibody or antigen-binding fragment thereof of claim 3, wherein the heavy chain constant region is a human IgG heavy chain constant region, wherein the heavy chain constant region is a human IgG1 heavy chain constant region or a human IgG4 heavy chain constant region.

5. The antibody or antigen-binding fragment thereof of claim 1, wherein the antibody or antigen-binding fragment further comprises a light chain constant region, wherein the light chain constant region is a human IgGκ light chain constant region.

6. The antibody or antigen-binding fragment thereof of claim 1, wherein the antibody or antigen-binding fragment thereof comprises a heavy chain comprising the same amino acid sequence as the heavy chain of the antibody produced by the CGX-c1 hybridoma deposited at the American Type Culture Collection (ATCC) as deposit number PTA-125491 on Nov. 14, 2018 and a light chain comprising the same amino acid sequence as the light chain of the antibody produced by the CGX-cl hybridoma deposited at the ATCC as deposit number PTA-125491 on Nov. 14, 2018.

7. The antibody or antigen-binding fragment there of claim 1, wherein the antibody or antigen-binding fragment thereof is capable of binding to the extracellular domain of TREM2.

8. The antibody or antigen-binding fragment thereof of claim 1, wherein the antibody or antigen-binding fragment thereof is a bispecific antibody or antigen-binding fragment thereof.

9. The antibody or antigen-binding fragment thereof of claim 2, wherein the antibody or antigen-binding fragment thereof is a bispecific antibody or antigen-binding fragment thereof.

10. A pharmaceutical composition comprising the antibody or antigen-binding fragment thereof of claim 1 and a pharmaceutically acceptable excipient.

11. A kit comprising the antibody or antigen-binding fragment thereof of claim 1 and a) a detection reagent, b) TREM2 antigen, c) a notice that reflects approval for use or sale for human administration, or d) a combination thereof.

12. An isolated polynucleotide comprising a nucleic acid molecule encoding the heavy chain variable region, light chain variable region, heavy chain, or light chain of the antibody or antigen-binding fragment thereof of claim 1.

13. An isolated vector comprising the polynucleotide of claim 12.

14. A host cell comprising the polynucleotide of claim 12.

15. A method of producing an antibody or antigen-binding fragment thereof that binds to human TREM2 comprising culturing the host cell of claim 14 so that the nucleic acid molecule is expressed and the antibody or antigen-binding fragment thereof is produced.

16. A method for detecting TREM2 in a sample comprising contacting the sample with the antibody or antigen-binding fragment thereof of claim 1.

17. A method for increasing the uptake of beta amyloid by an immune cell exposed to beta amyloid comprising contacting the immune cell with the antibody or antigen-binding fragment of claim 1.

18. A method of attenuating neuroinflammation or treating a neurodegenerative disease or disorder in a subject comprising administering to the subject the antibody or antigen-binding fragment of claim 1.

19. A method of reducing the number of amyloid plaques or reducing soluble TREM2 in a subject comprising administering to the subject the antibody or antigen-binding fragment of claim 1.

20. A method of improving cognition or attenuating cognitive dysfunction in a subject comprising administering to the subject the antibody or antigen-binding fragment of claim 1.

21. A method of attenuating neuroinflammation or treating a neurodegenerative disease or disorder in a subject comprising administering to the subject the antibody or antigen-binding fragment of claim 2.

22. A method of reducing the number of amyloid plaques or reducing soluble TREM2 in a subject comprising administering to the subject the antibody or antigen-binding fragment of claim 2.

* * * * *